US011833369B2

(12) United States Patent
Silver

(10) Patent No.: US 11,833,369 B2
(45) Date of Patent: *Dec. 5, 2023

(54) MONOCHROMATIC X-RAY IMAGING SYSTEMS AND METHODS

(71) Applicant: Imagine Scientific, Inc., Norwood, MA (US)

(72) Inventor: Eric H. Silver, Needham, MA (US)

(73) Assignee: Imagine Scientific, Inc., Norwood, MA (US)

( * ) Notice: Subject to any disclaimer, the term of this patent is extended or adjusted under 35 U.S.C. 154(b) by 3 days.

This patent is subject to a terminal disclaimer.

(21) Appl. No.: 17/528,439

(22) Filed: Nov. 17, 2021

(65) Prior Publication Data

US 2022/0323788 A1 Oct. 13, 2022

Related U.S. Application Data

(63) Continuation of application No. 16/577,485, filed on Sep. 20, 2019, now Pat. No. 11,185,714, which is a
(Continued)

(51) Int. Cl.
*A61B 6/00* (2006.01)
*A61N 5/10* (2006.01)
(Continued)

(52) U.S. Cl.
CPC ............ *A61N 5/1007* (2013.01); *A61B 6/025* (2013.01); *A61B 6/405* (2013.01); *A61B 6/4241* (2013.01);
(Continued)

(58) Field of Classification Search
CPC .. A61B 6/00; A61B 6/02; A61B 6/025; A61B 6/4035; A61B 6/405; A61B 6/4241;
(Continued)

(56) References Cited

U.S. PATENT DOCUMENTS 3,801,785 A  4/1974 Barrett
3,867,637 A  2/1975 Braun et al.
(Continued)

FOREIGN PATENT DOCUMENTS

CN  1791960 A  6/2006
DE  19639241 A1  4/1998
(Continued)

OTHER PUBLICATIONS

International Search Report and Written Opinion for International Application No. PCT/US2010/001142 dated Dec. 7, 2010.
(Continued)

*Primary Examiner* — Jurie Yun
(74) *Attorney, Agent, or Firm* — Wolf, Greenfield & Sacks, P.C.

(57) ABSTRACT

According to some aspects, a carrier configured for use with a broadband x-ray source comprising an electron source and a primary target arranged to receive electrons from the electron source to produce broadband x-ray radiation in response to electrons impinging on the primary target is provided. The carrier comprising a housing configured to be removeably coupled to the broadband x-ray source and configured to accommodate a secondary target capable of producing monochromatic x-ray radiation in response to incident broadband x-ray radiation, the housing comprising a transmissive portion configured to allow broadband x-ray radiation to be transmitted to the secondary target when present, and a blocking portion configured to absorb broadband x-ray radiation.

19 Claims, 45 Drawing Sheets

Related U.S. Application Data continuation of application No. 15/984,174, filed on May 18, 2018, now Pat. No. 10,532,223.

(60) Provisional application No. 62/508,996, filed on May 19, 2017.

(51) Int. Cl.
    H05G 2/00    (2006.01)
    A61B 6/02    (2006.01)
    H01J 35/08   (2006.01)
    H01J 35/18   (2006.01)

(52) U.S. Cl.
    CPC .............. *A61B 6/482* (2013.01); *A61B 6/502* (2013.01); *A61B 6/542* (2013.01); *A61B 6/583* (2013.01); *A61N 5/10* (2013.01); *H01J 35/112* (2019.05); *H05G 2/00* (2013.01); *A61N 2005/1087* (2013.01); *H01J 35/186* (2019.05); *H01J 2235/086* (2013.01); *H01J 2235/16* (2013.01)

(58) Field of Classification Search
    CPC ......... A61B 6/482; A61B 6/502; A61B 6/542; A61B 6/583; A61N 5/10; A61N 5/1007; A61N 2005/1087; H01J 35/08; H01J 35/112; H01J 35/186; H01J 2235/086; H01J 2235/16; H05G 2/00
    See application file for complete search history.

(56) References Cited

U.S. PATENT DOCUMENTS

| | | | |
|---|---|---|---|
| 3,920,999 | A | 11/1975 | Drexler et al. |
| 4,048,486 | A | 9/1977 | Kriege |
| 4,048,496 | A | 9/1977 | Albert |
| 4,174,481 | A | 11/1979 | Liebetruth |
| 4,382,181 | A | 5/1983 | Wang |
| 4,821,301 | A | 4/1989 | Cocks et al. |
| 4,894,852 | A | 1/1990 | Das Gupta |
| 4,903,287 | A | 2/1990 | Harding |
| 4,945,552 | A | 7/1990 | Ueda et al. |
| 5,073,915 | A | 12/1991 | Zhang et al. |
| 5,081,658 | A | 1/1992 | Imai et al. |
| 5,157,704 | A | 10/1992 | Harding |
| 5,159,621 | A | 10/1992 | Watanabe et al. |
| 5,257,303 | A | 10/1993 | Das Gupta |
| 5,742,658 | A | 4/1998 | Tiffin et al. |
| 5,787,146 | A | 7/1998 | Giebeler |
| 5,940,469 | A | 8/1999 | Hell et al. |
| 6,023,496 | A | 2/2000 | Kuwabara |
| 6,141,400 | A | 10/2000 | Schardt et al. |
| 6,298,113 | B1 | 10/2001 | Duclos et al. |
| 6,560,313 | B1 | 5/2003 | Harding et al. |
| 7,123,680 | B2 | 10/2006 | Katada et al. |
| 7,336,764 | B2 | 2/2008 | Reynolds |
| 7,394,890 | B1 | 7/2008 | Wang et al. |
| 7,486,984 | B2 | 2/2009 | Carroll |
| 7,567,650 | B2 | 7/2009 | Harding et al. |
| 7,809,113 | B2 | 10/2010 | Aoki et al. |
| 8,331,534 | B2 | 12/2012 | Silver |
| 9,066,702 | B2 | 6/2015 | Silver |
| 9,326,744 | B2 | 5/2016 | Silver |
| 9,425,021 | B2 | 8/2016 | Tamura et al. |
| 10,299,743 | B2 | 5/2019 | Silver |
| 10,398,909 | B2 | 9/2019 | Silver |
| 10,398,910 | B2 | 9/2019 | Silver |
| 10,532,223 | B2 | 1/2020 | Silver |
| 10,806,946 | B2 | 10/2020 | Silver |
| 10,818,467 | B2 | 10/2020 | Silver |
| 10,857,383 | B2 | 12/2020 | Silver |
| 11,158,435 | B2 | 10/2021 | Silver |
| 11,185,714 | B2 | 11/2021 | Silver |
| 11,213,265 | B2 | 1/2022 | Silver |
| 2003/0227996 | A1 | 12/2003 | Francke et al. |
| 2004/0046956 | A1 | 3/2004 | Gould et al. |
| 2004/0264644 | A1 | 12/2004 | Goebel et al. |
| 2005/0226378 | A1 | 10/2005 | Cocks et al. |
| 2006/0115051 | A1 | 6/2006 | Harding |
| 2006/0153332 | A1 | 7/2006 | Kohno et al. |
| 2006/0176997 | A1 | 8/2006 | Dilmanian et al. |
| 2006/0182223 | A1 | 8/2006 | Heuscher |
| 2007/0014392 | A1 | 1/2007 | Madey et al. |
| 2007/0138409 | A1 | 6/2007 | Daniel |
| 2007/0147584 | A1 | 6/2007 | Hofman |
| 2008/0069305 | A1 | 3/2008 | Harding et al. |
| 2008/0084966 | A1 | 4/2008 | Aoki et al. |
| 2011/0038455 | A1 | 2/2011 | Silver et al. |
| 2011/0170666 | A1 | 7/2011 | Chen et al. |
| 2012/0327963 | A1 | 12/2012 | Hubbard et al. |
| 2013/0125963 | A1 | 5/2013 | Binderbauer et al. |
| 2013/0188773 | A1 | 7/2013 | Silver |
| 2013/0294576 | A1 | 11/2013 | Pradhan et al. |
| 2014/0177801 | A1 | 6/2014 | Lee et al. |
| 2014/0362973 | A1 | 12/2014 | Ogura et al. |
| 2015/0003581 | A1 | 1/2015 | Silver |
| 2015/0170868 | A1 | 6/2015 | Heid et al. |
| 2015/0248942 | A1 | 9/2015 | Bar-Davidson et al. |
| 2015/0357069 | A1 | 12/2015 | Yun et al. |
| 2015/0366526 | A1 | 12/2015 | Silver |
| 2015/0369758 | A1 | 12/2015 | Silver |
| 2016/0120012 | A1 | 4/2016 | Heid |
| 2016/0242713 | A1 | 8/2016 | Silver |
| 2016/0249442 | A1 | 8/2016 | Kuritsyn et al. |
| 2017/0027531 | A1 | 2/2017 | Shiozawa et al. |
| 2017/0209575 | A1 | 7/2017 | Xie et al. |
| 2017/0251545 | A1 | 8/2017 | Klinkowstein et al. |
| 2018/0078229 | A1 | 3/2018 | Wang |
| 2018/0284036 | A1 | 10/2018 | Silver |
| 2018/0333591 | A1 | 11/2018 | Silver |
| 2019/0009106 | A1 | 1/2019 | Silver |
| 2019/0030362 | A1 | 1/2019 | Silver |
| 2019/0083811 | A1 | 3/2019 | Silver |
| 2019/0252149 | A1 | 8/2019 | Silver |
| 2019/0298289 | A1 | 10/2019 | Silver |
| 2020/0009402 | A1 | 1/2020 | Silver |
| 2020/0090827 | A1 | 3/2020 | Silver |
| 2020/0098537 | A1 | 3/2020 | Yun et al. |
| 2020/0138388 | A1 | 5/2020 | Silver |
| 2021/0123873 | A1 | 4/2021 | Silver |
| 2021/0251585 | A1 | 8/2021 | Silver |
| 2022/0265235 | A1 | 8/2022 | Silver |

FOREIGN PATENT DOCUMENTS

| | | |
|---|---|---|
| DE | 19639243 A1 | 4/1998 |
| EP | 2 420 112 B1 | 3/2017 |
| GB | 1443048 A | 7/1976 |
| JP | S49-97584 A | 9/1974 |
| JP | 50-056887 A | 5/1975 |
| JP | S50-120792 A | 9/1975 |
| JP | S60-249040 A | 12/1985 |
| JP | S63-304557 A | 12/1988 |
| JP | H01-190337 A | 7/1989 |
| JP | H03-266399 A | 11/1991 |
| JP | H04-019998 A | 1/1992 |
| JP | H04-337295 A | 11/1992 |
| JP | H04-363700 A | 12/1992 |
| JP | H05-346500 A | 12/1993 |
| JP | 06-109898 A | 4/1994 |
| JP | H06-103941 A | 4/1994 |
| JP | 06-277205 A | 10/1994 |
| JP | 07-095044 A | 4/1995 |
| JP | 2001-008924 A | 1/2001 |
| JP | 2001-224582 A | 8/2001 |
| JP | 2001-305079 A | 10/2001 |
| JP | 2002-208367 A | 7/2002 |
| JP | 2002-521676 A | 7/2002 |
| JP | 2005-091107 A | 4/2005 |
| JP | 2005-237730 A | 9/2005 |
| JP | 2006-038822 A | 2/2006 |
| JP | 2007-503703 A | 2/2007 |
| JP | 2007-531204 A | 11/2007 |

(56) References Cited

FOREIGN PATENT DOCUMENTS

| JP | 2008-082766 A | 4/2008 |
|---|---|---|
| JP | 2008-122101 A | 5/2008 |
| JP | 2012-524374 A | 10/2012 |
| JP | 2015-104460 A | 6/2015 |
| JP | 2016-000313 A2 | 1/2016 |
| KR | 10-2015-0026730 A | 3/2015 |
| KR | 10-2015-0114347 A | 10/2015 |
| WO | WO 00/05727 A1 | 2/2000 |
| WO | WO 03/103495 A1 | 12/2003 |
| WO | WO 2003/103495 A | 12/2003 |
| WO | WO 2004/102609 A1 | 11/2004 |
| WO | WO 2005/008716 A2 | 1/2005 |
| WO | 2007-207548 A | 8/2007 |
| WO | 2008-016339 A | 1/2008 |
| WO | WO 2008/052002 A2 | 5/2008 |

OTHER PUBLICATIONS

Extended European Search Report dated Nov. 19, 2013 for Application No. 10764778.6.
Japanese Office Action for Japanese Application No. 2015-168321 dated Aug. 9, 2016 and English translation thereof.
International Search Report and Written Opinion for International Application No. PCT/US2015/037537 dated Sep. 18, 2015.
International Preliminary Report on Patentability for International Application No. PCT/US2015/037537 dated Jan. 5, 2017.
Invitation to Pay Additional Fees for International Application No. PCT/US2018/33526 mailed Jul. 26, 2018.
International Search Report and Written Opinion for International Application No. PCT/US2018/33526 dated Sep. 14, 2018.
International Preliminary Report on Patentability for International Application No. PCT/US2018/033526 dated Nov. 28, 2019.
Extended European Search Report for European Application No. EP 18801379.1 dated Mar. 9, 2021.
International Search Report and Written Opinion for International Application No. PCT/US2019/051042 dated Dec. 4, 2019.
International Preliminary Report on Patentability for International Application No. PCT/US2019/051042 dated Mar. 25, 2021.
International Search Report and Written Opinion for International Application No. PCT/US19/17362 dated Apr. 23, 2019.
International Preliminary Report on Patentability for International Application No. PCT/US2019/017362 dated Aug. 20, 2020.
Extended European Search Report dated Oct. 4, 2021 in connection with European Application No. 19750535.7.
Gilbert et al., The organic-mineral interface in biominerals. Reviews in Mineralogy and Geochemistry. Jan. 1, 2005;59(1):157-85.
Kuramoto et al., Sharpening of an energy band of diagnostic x-ray spectrum with metal filters. World Congress Medical Physics and Biomedical Engineering. 2006;3(3):1533-1536.
Seidler et al., A laboratory-based hard x-ray monochromator for high-resolution x-ray emission spectroscopy and x-ray absorption near edge structure measurements. Review of scientific instruments. Nov. 20, 2014;85(11):113906-1-12.
Silver et al., The x-ray: reloaded. RT-IMAGE. Dec. 1, 2008;21(48):4 pages.
Marfeld et al., Fluor'X: a near monochromatic x-ray source. Proc. SPIE, Advances in Laboratory-based X-Ray Sources and Optics II. Dec. 6, 2001;(4502):117-25.

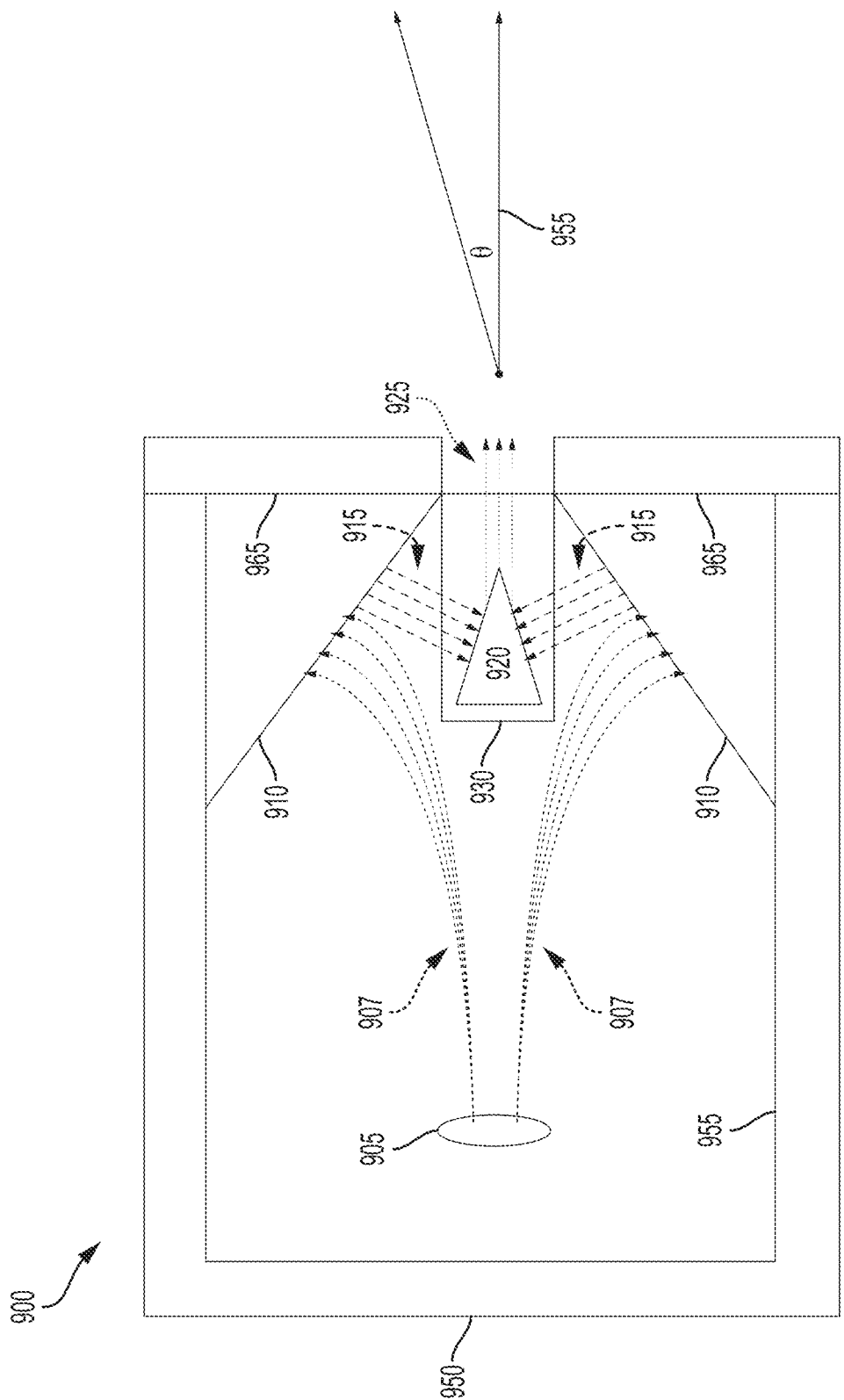

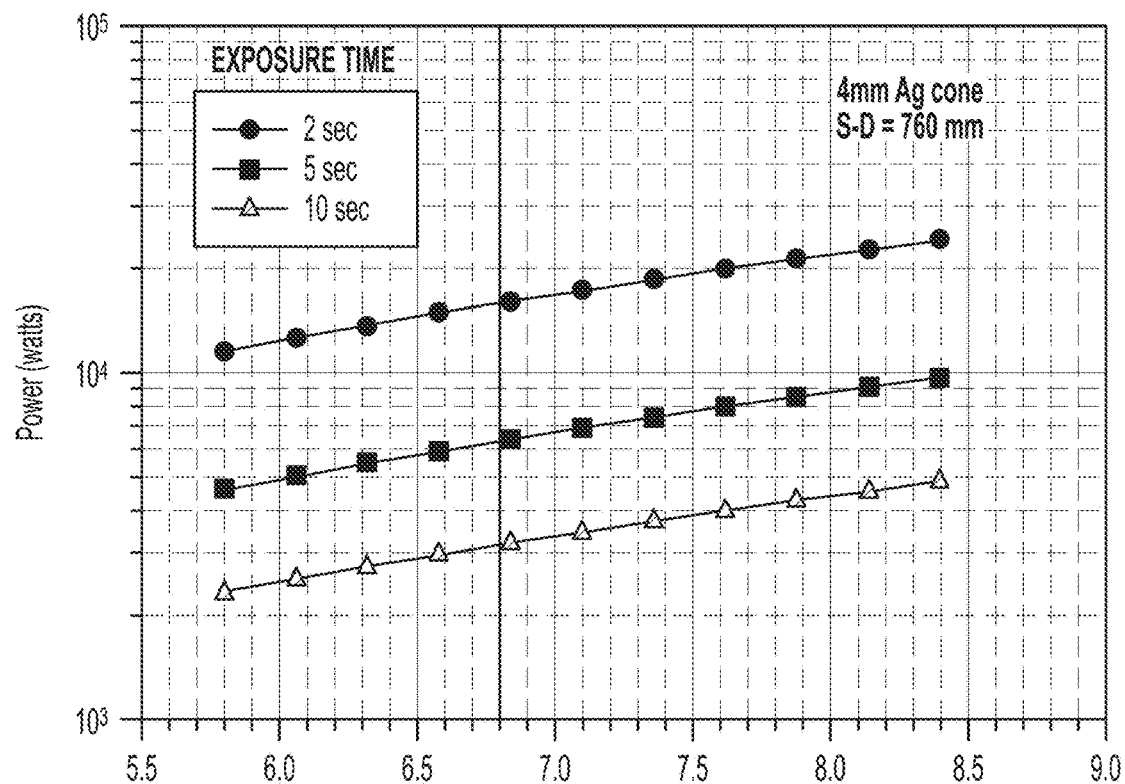
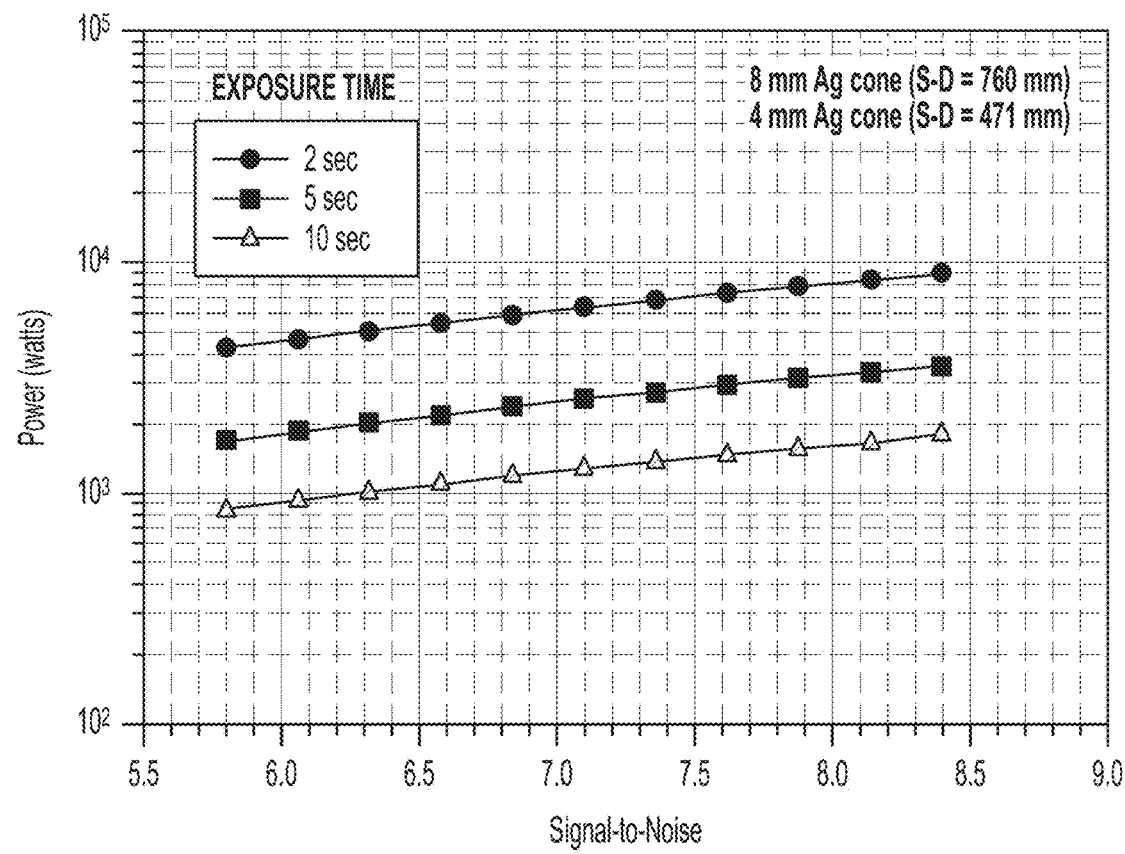
FIG. 39

MONOCHROMATIC X-RAY IMAGING SYSTEMS AND METHODS

CROSS REFERENCE TO RELATED APPLICATIONS

This application claims the benefit under 35 U.S.C. § 120 and is a continuation of U.S. application Ser. No. 16/577,485, filed Sep. 20, 2019, entitled "MONOCHROMATIC X-RAY IMAGING SYSTEMS AND METHODS", which claims the benefit under 35 U.S.C. § 120 and is a continuation of U.S. application Ser. No. 15/984,174, filed May 18, 2018, entitled MONOCHROMATIC X-RAY IMAGING SYSTEMS AND METHODS, which claims priority under 35 U.S.C. § 119 to U.S. Provisional Application Ser. No. 62/508,996 filed May 19, 2017, and titled MONOCHROMATIC X-RAY SYSTEMS AND APPARATUS, each application of which is herein incorporated by reference in its entirety.

BACKGROUND

Traditional diagnostic radiography uses x-ray generators that emit X-rays over a broad energy band. A large fraction of this band contains x-rays which are not useful for medical imaging because their energy is either too high to interact in the tissue being examined or too low to reach the X-ray detector or film used to record them. The x-rays with too low an energy to reach the detector are especially problematic because they unnecessarily expose normal tissue and raise the radiation dose received by the patient. It has long been realized that the use of monochromatic x-rays, if available at the appropriate energy, would provide optimal diagnostic images while minimizing the radiation dose. To date, no such monochromatic X-ray source has been available for routine clinical diagnostic use.

Monochromatic radiation has been used in specialized settings. However, conventional systems for generating monochromatic radiation have been unsuitable for clinical or routine commercial use due to their prohibitive size, cost and/or complexity. For example, monochromatic X-rays can be copiously produced in synchrotron sources utilizing an inefficient Bragg crystal as a filter or using a solid, flat target x-ray fluorescer but these are very large and not practical for routine use in hospitals and clinics.

Monochromatic x-rays may be generated by providing in series a target (also referred to as the anode) that produces broad spectrum radiation in response to an incident electron beam, followed by a fluorescing target that produces monochromatic x-rays in response to incident broad spectrum radiation. The term "broad spectrum radiation" is used herein to describe Bremsstrahlung radiation with or without characteristic emission lines of the anode material. Briefly, the principles of producing monochromatic x-rays via x-ray fluorescence are as follows.

Thick Target Bremsstrahlung

In an x-ray tube electrons are liberated from a heated filament called the cathode and accelerated by a high voltage (e.g., —50 kV) toward a metal target called the anode as illustrated schematically in FIG. 1. The high energy electrons interact with the atoms in the anode. Often an electron with energy $E_1$ comes close to a nucleus in the target and its trajectory is altered by the electromagnetic interaction. In this deflection process, it decelerates toward the nucleus. As it slows to an energy $E_2$, it emits an X-ray photon with energy $E_2-E_1$. This radiation is called Bremsstrahlung radiation (braking radiation) and the kinematics are shown in FIG. 2.

The energy of the emitted photon can take any value up to the maximum energy of the incident electron, $E_{max}$. As the electron is not destroyed it can undergo multiple interactions until it loses all of its energy or combines with an atom in the anode. Initial interactions will vary from minor to major energy changes depending on the actual angle and proximity to the nucleus. As a result, Bremsstrahlung radiation will have a generally continuous spectrum, as shown in FIG. 3. The probability of Bremsstrahlung production is proportional to $Z^2$, where Z is the atomic number of the target material, and the efficiency of production is proportional to Z and the x-ray tube voltage. Note that low energy Bremsstrahlung X-rays are absorbed by the thick target anode as they try to escape from deep inside causing the intensity curve to bend over at the lowest energies, as discussed in further detail below.

Characteristic Line Emission

While most of the electrons slow down and have their trajectories changed, some will collide with electrons that are bound by an energy, BE, in their respective orbitals or shells that surround the nucleus in the target atom. As shown in FIG. 4, these shells are denoted by K, L, M, N, etc. In the collision between the incoming electron and the bound electron, the bound electron will be ejected from the atom if the energy of the incoming electron is greater than BE of the orbiting electron. For example, the impacting electron with energy $E>BE_K$, shown in FIG. 4, will eject the K-shell electron leaving a vacancy in the K shell. The resulting excited and ionized atom will de-excite as an electron in an outer orbit will fill the vacancy. During the de-excitation, an X-ray is emitted with an energy equal to the difference between the initial and final energy levels of the electron involved with the de-excitation. Since the energy levels of the orbital shells are unique to each element on the Periodic Chart, the energy of the X-ray identifies the element. The energy will be monoenergetic and the spectrum appears monochromatic rather than a broad continuous band. Here, monochromatic means that the width in energy of the emission line is equal to the natural line width associated with the atomic transition involved. For copper Kα x-rays, the natural line width is about 4 eV. For Zr Kα, Mo Kα and Pt Kα, the line widths are approximately, 5.7 eV, 6.8 eV and 60 eV, respectively. The complete spectrum from an X-ray tube with a molybdenum target as the anode is shown in FIG. 5. The characteristic emission lines unique to the atomic energy levels of molybdenum are shown superimposed on the thick target Bremsstrahlung.

X-Ray Absorption and X-Ray Fluorescence

When an x-ray from any type of x-ray source strikes a sample, the x-ray can either be absorbed by an atom or scattered through the material. The process in which an x-ray is absorbed by an atom by transferring all of its energy to an innermost electron is called the photoelectric effect, as illustrated in FIG. 6A. This occurs when the incident x-ray has more energy than the binding energy of the orbital electron it encounters in a collision. In the interaction the photon ceases to exist imparting all of its energy to the orbital electron. Most of the x-ray energy is required to overcome the binding energy of the orbital electron and the remainder is imparted to the electron upon its ejection leaving a vacancy in the shell. The ejected free electron is called a photoelectron. A photoelectric interaction is most likely to occur when the energy of the incident photon exceeds but is relatively close to the binding energy of the electron it strikes.

As an example, a photoelectric interaction is more likely to occur for a K-shell electron with a binding energy of 23.2 keV when the incident photon is 25 keV than if it were 50 keV. This is because the photoelectric effect is inversely proportional to approximately the third power of the X-ray energy. This fall-off is interrupted by a sharp rise when the x-ray energy is equal to the binding energy of an electron shell (K, L, M, etc.) in the absorber. The lowest energy at which a vacancy can be created in the particular shell and is referred to as the edge. FIG. 7 shows the absorption of tin (Sn) as a function of x-ray energy. The absorption is defined on the ordinate axis by its mass attenuation coefficient. The absorption edges corresponding to the binding energies of the L orbitals and the K orbitals are shown by the discontinuous jumps at approximately 43.4 keV and 29 keV, respectively. Every element on the Periodic Chart has a similar curve describing its absorption as a function of x-ray energy.

The vacancies in the inner shell of the atom present an unstable condition for the atom. As the atom returns to its stable condition, electrons from the outer shells are transferred to the inner shells and in the process emit a characteristic x-ray whose energy is the difference between the two binding energies of the corresponding shells as described above in the section on Characteristic Line Emission. This photon-induced process of x-ray emission is called X-ray Fluorescence, or XRF. FIG. 6B shows schematically X-ray fluorescence from the K shell and a typical x-ray fluorescence spectrum from a sample of aluminum is shown in FIG. 8. The spectrum is measured with a solid state, photon counting detector whose energy resolution dominates the natural line width of the L-K transition. It is important to note that these monoenergetic emission lines do not sit on top of a background of broad band continuous radiation; rather, the spectrum is Bremsstrahlung free.

SUMMARY

According to some embodiments, a carrier configured for use with a broadband x-ray source comprising an electron source and a primary target arranged to receive electrons from the electron source to produce broadband x-ray radiation in response to electrons impinging on the primary target is provided. The carrier comprising a housing configured to be removeably coupled to the broadband x-ray source and configured to accommodate a secondary target capable of producing monochromatic x-ray radiation in response to incident broadband x-ray radiation, the housing comprising a transmissive portion configured to allow broadband x-ray radiation to be transmitted to the secondary target when present, and a blocking portion configured to absorb broadband x-ray radiation.

Some embodiments include a carrier configured for use with a broadband x-ray source comprising an electron source and a primary target arranged to receive electrons from the electron source to produce broadband x-ray radiation in response to electrons impinging on the primary target, the carrier comprising a housing configured to accommodate a secondary target that produces monochromatic x-ray radiation in response to impinging broadband x-ray radiation, the housing further configured to be removably coupled to the broadband x-ray source so that, when the housing is coupled to the broadband x-ray source and is accommodating the secondary target, the secondary target is positioned so that at least some broadband x-ray radiation from the primary target impinges on the secondary target to produce monochromatic x-ray radiation, the housing comprising a first portion comprising a first material substantially transparent to the broadband x-ray radiation, and a second portion comprising a second material substantially opaque to broadband x-ray radiation.

Some embodiments include a monochromatic x-ray device comprising an electron source configured to emit electrons, a primary target configured to produce broadband x-ray radiation in response to incident electrons from the electron source, a secondary target configured to generate monochromatic x-ray radiation via fluorescence in response to incident broadband x-ray radiation, and a housing for the secondary target comprising an aperture through which monochromatic x-ray radiation from the secondary target is emitted, the housing configured to position the secondary target so that at least some of the broadband x-ray radiation emitted by the primary target is incident on the secondary target so that, when the monochromatic x-ray device is operated, monochromatic x-ray radiation is emitted via the aperture having a monochromaticity of greater than or equal to 0.7 across a field of view of at least approximately 15 degrees. According to some embodiments, monochromatic x-ray radiation emitted via the aperture has a monochromaticity of greater than or equal to 0.8 across a field of view of at least approximately 15 degrees. According to some embodiments, monochromatic x-ray radiation emitted via the aperture has a monochromaticity of greater than or equal to 0.9 across a field of view of at least approximately 15 degrees. According to some embodiments, monochromatic x-ray radiation emitted via the aperture has a monochromaticity of greater than or equal to 0.95 across a field of view of at least approximately 15 degrees.

Some embodiments include a monochromatic x-ray device comprising an electron source configured to emit electrons, a primary target configured to produce broadband x-ray radiation in response to incident electrons from the electron source, and a secondary target configured to generate monochromatic x-ray radiation via fluorescence in response to incident broadband x-ray radiation, wherein the device is operated using a voltage potential between the electron source and the primary target that is greater than twice the energy of an absorption edge of the secondary target. According to some embodiments, the device is operated using a voltage potential between the electron source and the primary target that is greater than three times the energy of an absorption edge of the secondary target. According to some embodiments, the device is operated using a voltage potential between the electron source and the primary target that is greater than four times the energy of an absorption edge of the secondary target. According to some embodiments, the device is operated using a voltage potential between the electron source and the primary target that is greater than five times the energy of an absorption edge of the secondary target.

Some embodiments include a monochromatic x-ray device comprising an electron source comprising a toroidal cathode, the electron source configured to emit electrons, a primary target configured to produce broadband x-ray radiation in response to incident electrons from the electron source, at least one guide arranged concentrically to the toroidal cathode to guide electrons toward the primary target, and a secondary target configured to generate monochromatic x-ray radiation via fluorescence in response to incident broadband x-ray radiation. According to some embodiments, the at least one guide comprises at least one first inner guide arranged concentrically within the toroidal cathode. According to some embodiments, the at least one guide comprises at least one first outer guide arranged concentrically outside the toroidal cathode.

BRIEF DESCRIPTION OF THE DRAWINGS

Various aspects and embodiments of the disclosed technology will be described with reference to the following figures. It should be appreciated that the figures are not necessarily drawn to scale.

FIG. 9 illustrates an x-ray apparatus for generating monochromatic x-rays;

FIG. 39 illustrates power requirements needed for desired signal to noise ratios for different exposure times and cone geometries;

DETAILED DESCRIPTION

Figure 1:
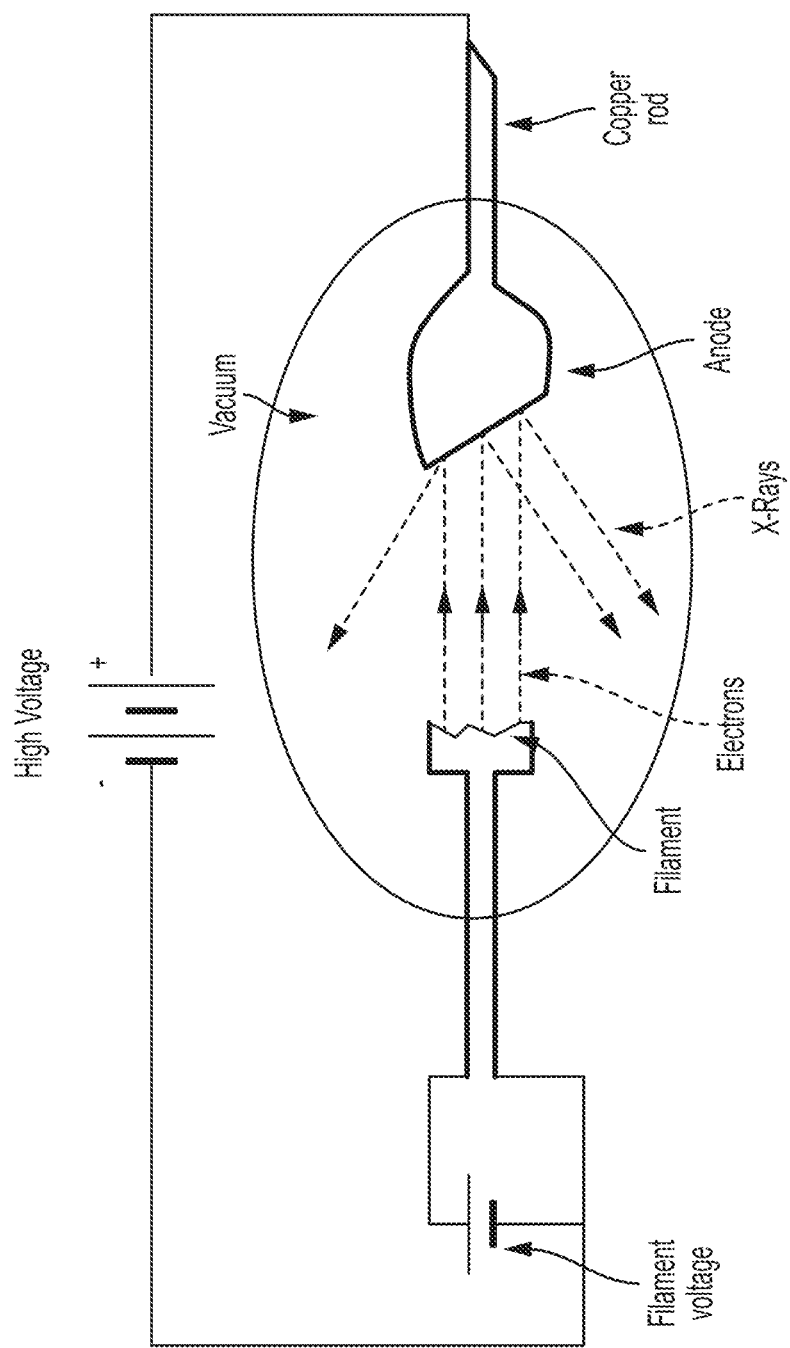
FIG. 1 illustrates a schematic of a broadband x-ray source.
Figure 2:
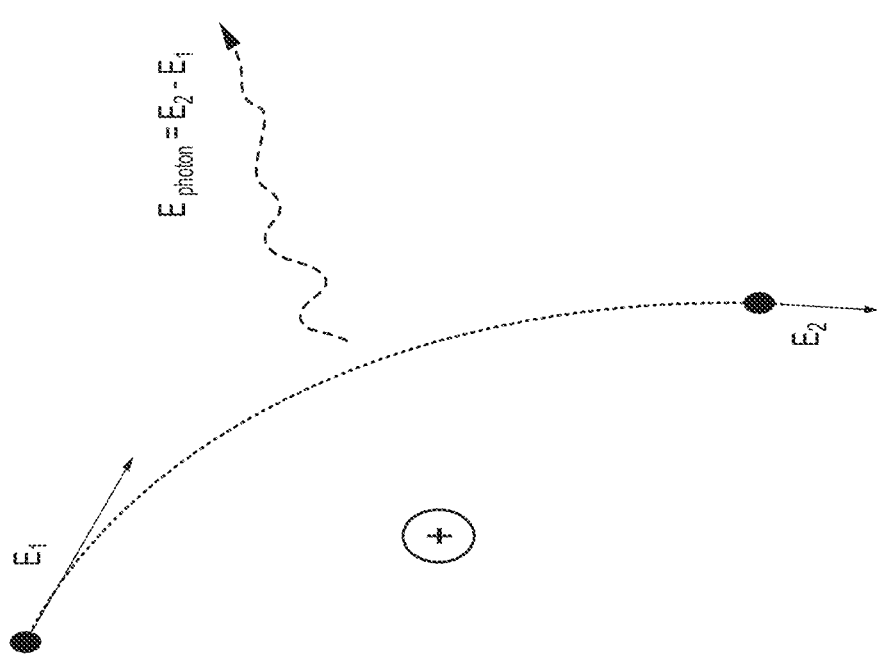
FIG. 2. illustrates the scenario in which an electron (much lighter than the nucleus) comes very close to the nucleus and the electromagnetic interaction causes a deviation of the trajectory where the electron loses energy and an X-ray photon is emitted and describes Bremsstralung in its simplest form.

As discussed above, conventional x-ray systems capable of generating monochromatic radiation to produce diagnostic images are typically not suitable for clinical and/or commercial use due to the prohibitively high costs of manufacturing, operating and maintaining such systems and/or because the system footprints are much too large for clinic and hospital use. As a result, research with these systems are limited in application to investigations at and by the relatively few research institutions that have invested in large, complex and expensive equipment.

Cost effective monochromatic x-ray imaging in a clinical setting has been the goal of many physicists and medical professionals for decades, but medical facilities such as hospitals and clinics remain without a viable option for monochromatic x-ray equipment that can be adopted in a clinic for routine diagnostic use.

The inventor has developed methods and apparatus for producing selectable, monochromatic x-radiation over a relatively large field-of-view (FOV). Numerous applications can benefit from such a monochromatic x-ray source, in both the medical and non-medical disciplines. Medical applications include, but are not limited to, imaging of breast tissue, the heart, prostate, thyroid, lung, brain, torso and limbs. Non-medical disciplines include, but are not limited to, non-destructive materials analysis via x-ray absorption, x-ray diffraction and x-ray fluorescence. The inventor has recognized that 2D and 3D X-ray mammography for routine breast cancer screening could immediately benefit from the existence of such a monochromatic source.

According to some embodiments, selectable energies (e.g., up to 100 key) are provided to optimally image different anatomical features. Some embodiments facilitate providing monochromatic x-ray radiation having an intensity that allows for relatively short exposure times, reducing the radiation dose delivered to a patient undergoing imaging. According to some embodiments, relatively high levels of intensity can be maintained using relatively small compact regions from which monochromatic x-ray radiation is emitted, facilitating x-ray imaging at spatial resolutions suitable for high quality imaging (e.g., breast imaging). The ability to generate relatively high intensity monochromatic x-ray radiation from relatively small compact regions facilitates short, low dose imaging at relatively high spatial resolution that, among other benefits, addresses one or more problems of conventional x-ray imaging systems (e.g., by overcoming difficulties in detecting cancerous lesions in thick breast tissue while still maintaining radiation dose levels below the limit set by regulatory authorities, according to some embodiments).

With conventional mammography systems, large (thick) and dense breasts are difficult, if not impossible, to examine at the same level of confidence as smaller, normal density breast tissue. This seriously limits the value of mammography for women with large and/or dense breasts (30-50% of the population), a population of women who have a six-fold higher incidence of breast cancer. The detection sensitivity falls from 85% to 64% for women with dense breasts and to 45% for women with extremely dense breasts. Additionally, using conventional x-ray imaging systems (i.e., broadband x-ray imaging systems) false positives and unnecessary biopsies occur at unsatisfactory levels. Techniques described herein facilitate monochromatic x-ray imaging capable of providing a better diagnostic solution for women with large and/or dense breasts who have been chronically undiagnosed, over-screened and are most at risk for breast cancer. Though benefits associated with some embodiments have specific advantages for thick and/or dense breasts, it should be appreciated that techniques provided herein for monochromatic x-ray imaging also provide advantages for screening of breasts of any size and density, as well as providing benefits for other clinical diagnostic applications. For example, techniques described herein facilitate reducing patient radiation dose by a factor of 6-26 depending on tissue density for all patients over conventional x-ray imaging systems currently deployed in clinical settings, allowing for annual and repeat exams while significantly reducing the lifetime radiation exposure of the patient. Additionally, according to some embodiments, screening may be performed without painful compression of the breast in certain circumstances. Moreover, the technology described herein facilitates the manufacture of monochromatic x-ray systems that are relatively low cost, keeping within current cost constraints of broadband x-ray systems currently in use for clinical mammography.

Monochromatic x-ray imaging may be performed with approved contrast agents to further enhance detection of tissue anomalies at a reduced dose. Techniques described herein may be used with three dimensional 3D tomosynthesis at similarly low doses. Monochromatic radiation using techniques described herein may also be used to perform in-situ chemical analysis (e.g., in-situ analysis of the chemical composition of tumors), for example, to improve the chemical analysis techniques described in U.S. patent application Ser. No. 15/825,787, filed Nov. 28, 2017 and titled "Methods and Apparatus for Determining Information Regarding Chemical Composition Using X-ray Radiation," which application is incorporated herein in its entirety.

Conventional monochromatic x-ray sources have previously been developed for purposes other than medical imaging and, as a result, are generally unsuitable for clinical purposes. Specifically, the monochromaticity, intensity, spatial resolution and/or power levels may be insufficient for medical imaging purposes. The inventor has developed techniques for producing monochromatic x-ray radiation suitable for numerous applications, including for clinical purposes such as breast and other tissue imaging, aspects of which are described in further detail below. The inventor recognized that conventional monochromatic x-ray sources emit significant amounts of broadband x-ray radiation in addition to the emitted monochromatic x-ray radiation. As a result, the x-ray radiation emitted from such monochromatic x-ray sources have poor monochromaticity due to the significant amounts of broadband radiation that is also emitted by the source, contaminating the x-ray spectrum.

The inventor has developed techniques for producing x-ray radiation with high degrees of monochromaticity (e.g., as measured by the ratio of monochromatic x-ray radiation to broadband radiation as discussed in further detail below), both in the on-axis direction and off-axis directions over a relatively large field of view. Techniques described herein enable the ability to increase the power of the broadband x-ray source without significantly increasing broadband x-ray radiation contamination (i.e., without substantially reducing monochromaticity). As a result, higher intensity monochromatic x-ray radiation may be produced using increased power levels while maintaining high degrees of monochromaticity.

According to some embodiments, a monochromatic x-ray device is provided that is capable of producing monochromatic x-ray radiation having characteristics (e.g., monochromaticity, intensity, etc.) that enable exposure times of less than 20 seconds and, according to some embodiments, exposure times of less than 10 seconds for mammography.

According to some embodiments, a monochromatic x-ray device is provided that emits monochromatic x-rays having a high degree of monochromaticity (e.g., at 90% purity or better) over a field of view sufficient to image a target organ (e.g., a breast) in a single exposure to produce an image at a spatial resolution suitable for diagnostics (e.g., a spatial resolution of a 100 microns or better).

Following below are more detailed descriptions of various concepts related to, and embodiments of, monochromatic x-ray systems and techniques regarding same. It should be appreciated that the embodiments described herein may be implemented in any of numerous ways. Examples of specific implementations are provided below for illustrative purposes only. It should be appreciated that the embodiments and the features/capabilities provided may be used individually, all together, or in any combination of two or more, as aspects of the technology described herein are not limited in this respect.

FIG. 9 illustrates a two dimensional (2D) schematic cut of a conventional x-ray apparatus for generating monochromatic x-rays via x-ray fluorescence. The x-ray apparatus illustrated in FIG. 9 is similar in geometry to the x-ray apparatus illustrated and described in U.S. Pat. No. 4,903,287, titled "Radiation Source for Generating Essentially Monochromatic X-rays," as well as the monochromatic x-ray source illustrated and described in Marfeld, et al., Proc. SPIE Vol. 4502, p. 117-125, Advances in Laboratory-based X-ray Sources and Optics II, Ali M. Khounsayr; Carolyn A. MacDonald; Eds. Referring to FIG. 9, x-ray apparatus 900 comprises a vacuum tube 950 that contains a toroidal filament 905 that operates as a cathode and primary target 910 that operates as an anode of the circuit for generating broadband x-ray radiation. Vacuum tube 950 includes a vacuum sealed enclosure formed generally by housing 955, front portion 965 (e.g., a copper faceplate) and a window 930 (e.g., a beryllium window).

Figure 3:
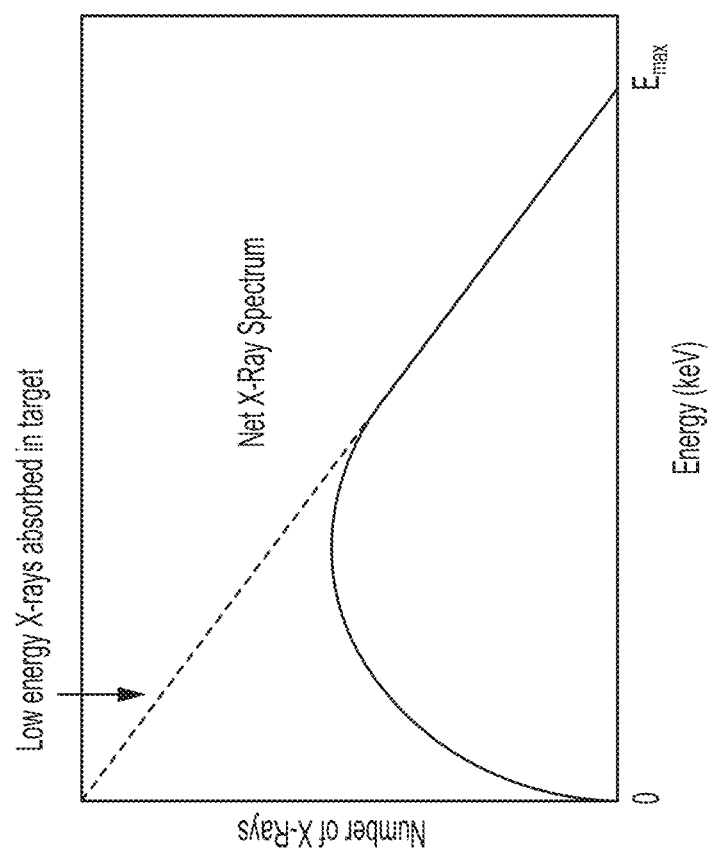
FIG. 3 illustrates the Bremsstrahlung spectrum produced by a typical X-ray tube, wherein the lower energy x-rays trying to escape the target are absorbed causing the characteristic roll over of the spectrum at low energies.
Figure 4:
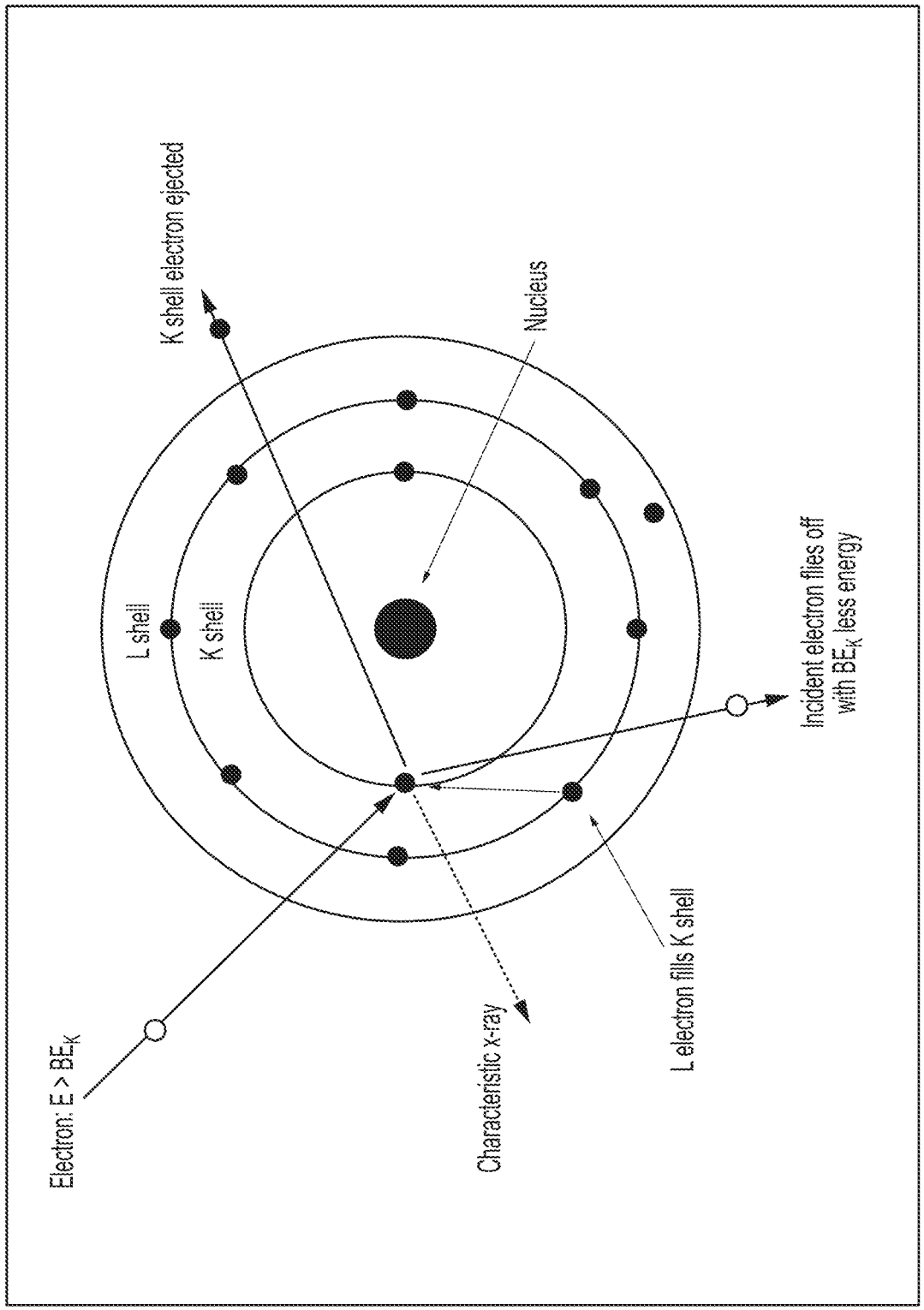
FIG. 4 illustrates the physical phenomenon that generates characteristic line emissions.
Figure 5:
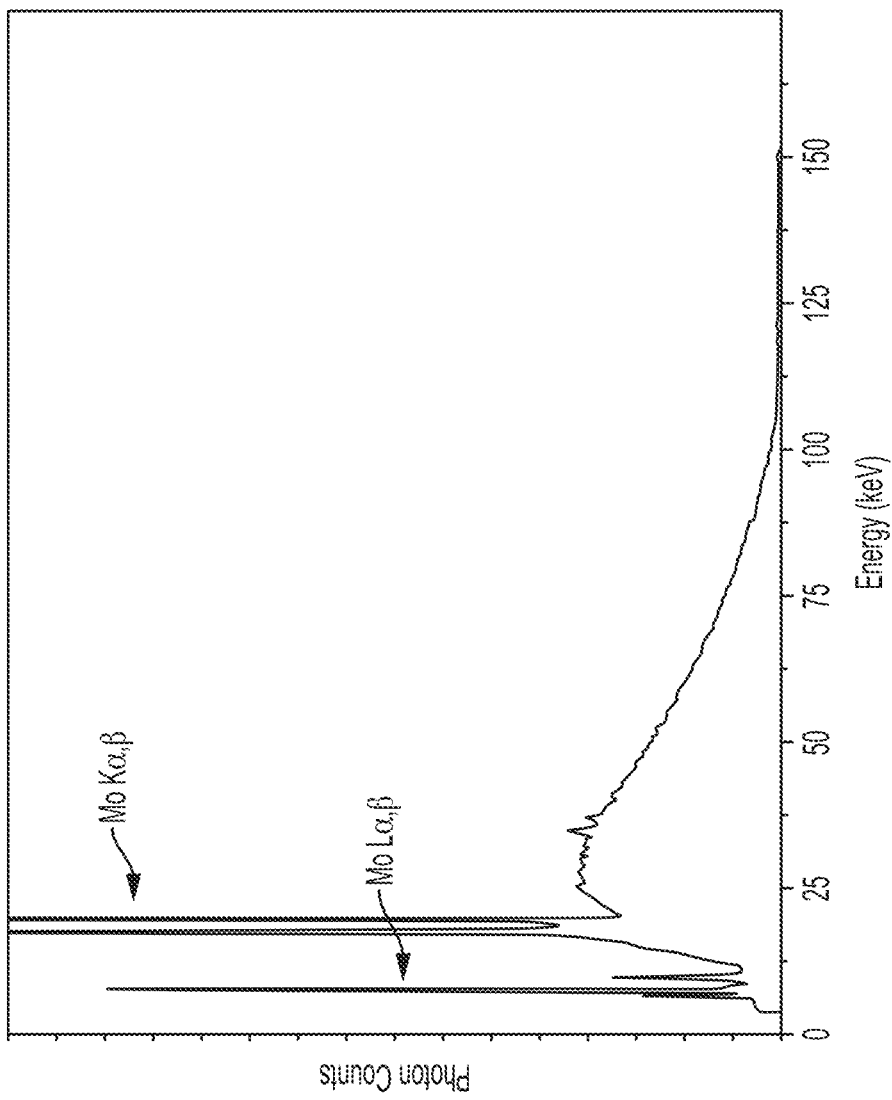
FIG. 5 illustrates the combined spectrum from an X-ray tube with a molybdenum anode showing the thick target Bremsstrahlung and the characteristic molybdenum line emission.
Figure 6A:
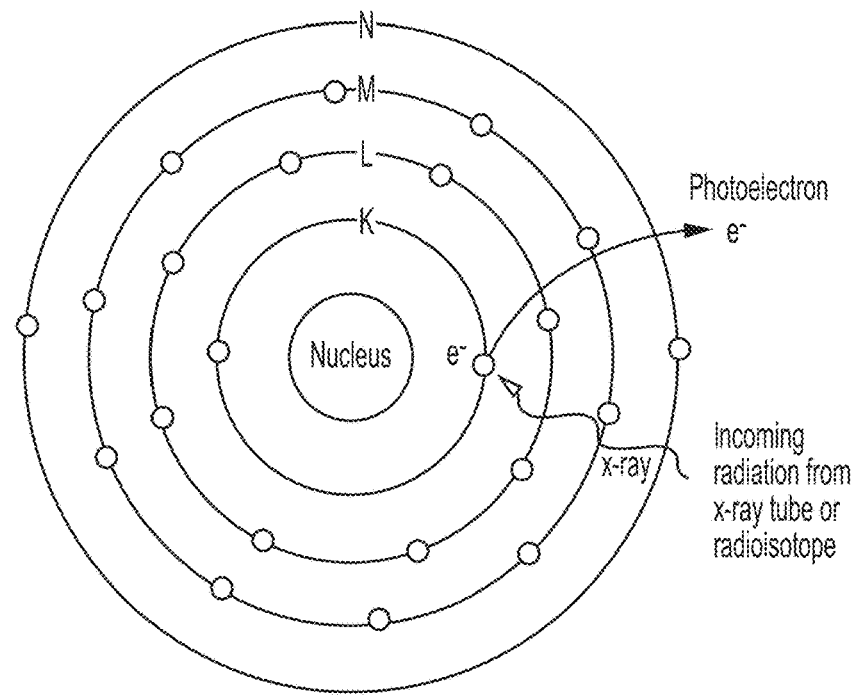
FIG. 6A illustrates the photoelectric effect.
Figure 6B:
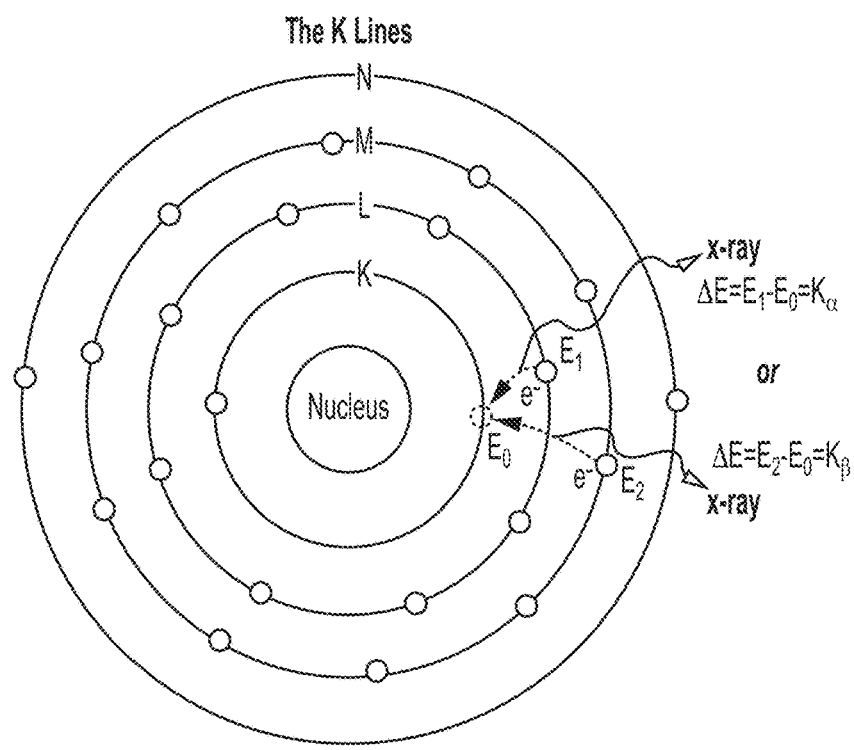
FIG. 6B illustrates the principle of X-Ray fluorescence from the K shell.

In operation, electrons (e.g., exemplary electrons 907) from filament 905 (cathode) are accelerated toward primary target 910 (anode) due to the electric field established by a high voltage bias between the cathode and the anode. As the electrons are decelerated by the primary target 910, broadband x-ray radiation 915 (i.e., Bremsstrahlung radiation as shown in FIG. 3) is produced. Characteristic emission lines unique to the primary target material may also be produced by the electron bombardment of the anode material provided the voltage is large enough to produce photoelectrons. Thus, broadband x-ray radiation (or alternatively broad spectrum radiation) refers to Bremsstrahlung radiation with or without characteristic emission lines of the primary target. The broadband radiation 915 emitted from primary target 910 is transmitted through window 930 of the vacuum enclosure to irradiate secondary target 920. Window 930 provides a transmissive portion of the vacuum enclosure made of a material (e.g., beryllium) that generally transmits broadband x-ray radiation generated by primary target 910 and blocks electrons from impinging on the secondary target 920 (e.g., electrons that scatter off of the primary target) to prevent unwanted Bremststralung radiation from being produced. Window 930 may be cup-shaped to accommodate secondary target 920 outside the vacuum enclosure, allowing the secondary target to be removed and replaced without breaking the vacuum seal of x-ray tube 950.

In response to incident broadband x-ray radiation from primary target 910, secondary target 920 generates, via fluorescence, monochromatic x-ray radiation 925 characteristic of the element(s) in the second target. Secondary target 920 is conical in shape and made from a material selected so as to produce fluorescent monochromatic x-ray radiation at a desired energy, as discuss in further detail below. Broadband x-ray radiation 915 and monochromatic x-ray radiation 925 are illustrated schematically in FIG. 9 to illustrate the general principle of using a primary target and a secondary target to generate monochromatic x-ray radiation via fluorescence. It should be appreciated that broadband and monochromatic x-ray radiation will be emitted in the $4\pi$ directions by the primary and secondary targets, respectively. Accordingly, x-ray radiation will be emitted from x-ray tube 950 at different angles $\theta$ relative to axis 955 corresponding to the longitudinal axis through the center of the aperture of x-ray tube 950.

As discussed above, the inventor has recognized that conventional x-ray apparatus for generating monochromatic x-ray radiation (also referred to herein as monochromatic x-ray sources) emit significant amounts of broadband x-ray radiation. That is, though conventional monochromatic sources report the ability to produce monochromatic x-ray radiation, in practice, the monochromaticity of the x-ray radiation emitted by these conventional apparatus is poor (i.e., conventional monochromatic sources exhibit low degrees of monochromaticity. For example, the conventional monochromatic source described in Marfeld, using a source operated at 165 kV with a secondary target of tungsten (W), emits monochromatic x-ray radiation that is approximately 50% pure (i.e., the x-ray emission is approximately 50% broadband x-ray radiation). As another example, a conventional monochromatic x-ray source of the general geometry illustrated in FIG. 9, operating with a cathode at a negative voltage of −50 kV, a primary target made of gold (Au; Z=79) at ground potential, and a secondary target made of tin (Sn; Z=50), emits the x-ray spectra illustrated in FIG. 10A (on-axis) and FIG. 10B (off-axis). As discussed above, x-ray radiation will be emitted from the x-ray tube at different angles $\theta$ relative to the longitudinal axis of the x-ray tube (axis 955 illustrated in FIG. 9).

Figure 10A:
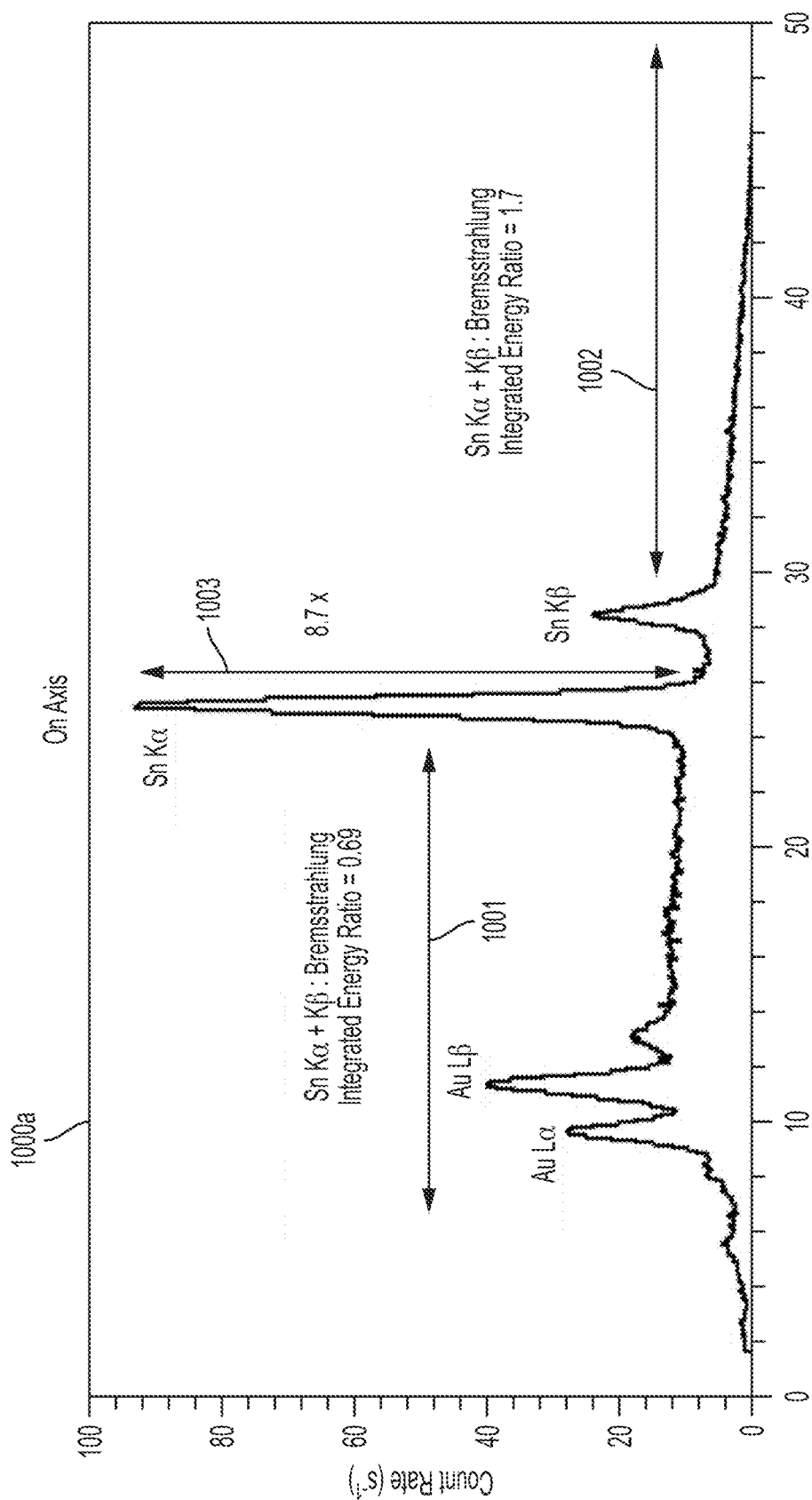
FIGS. 10A and 10B illustrate on-axis and off-axis x-ray spectra of x-ray radiation emitted from a conventional monochromatic x-ray apparatus.
Figure 10B:
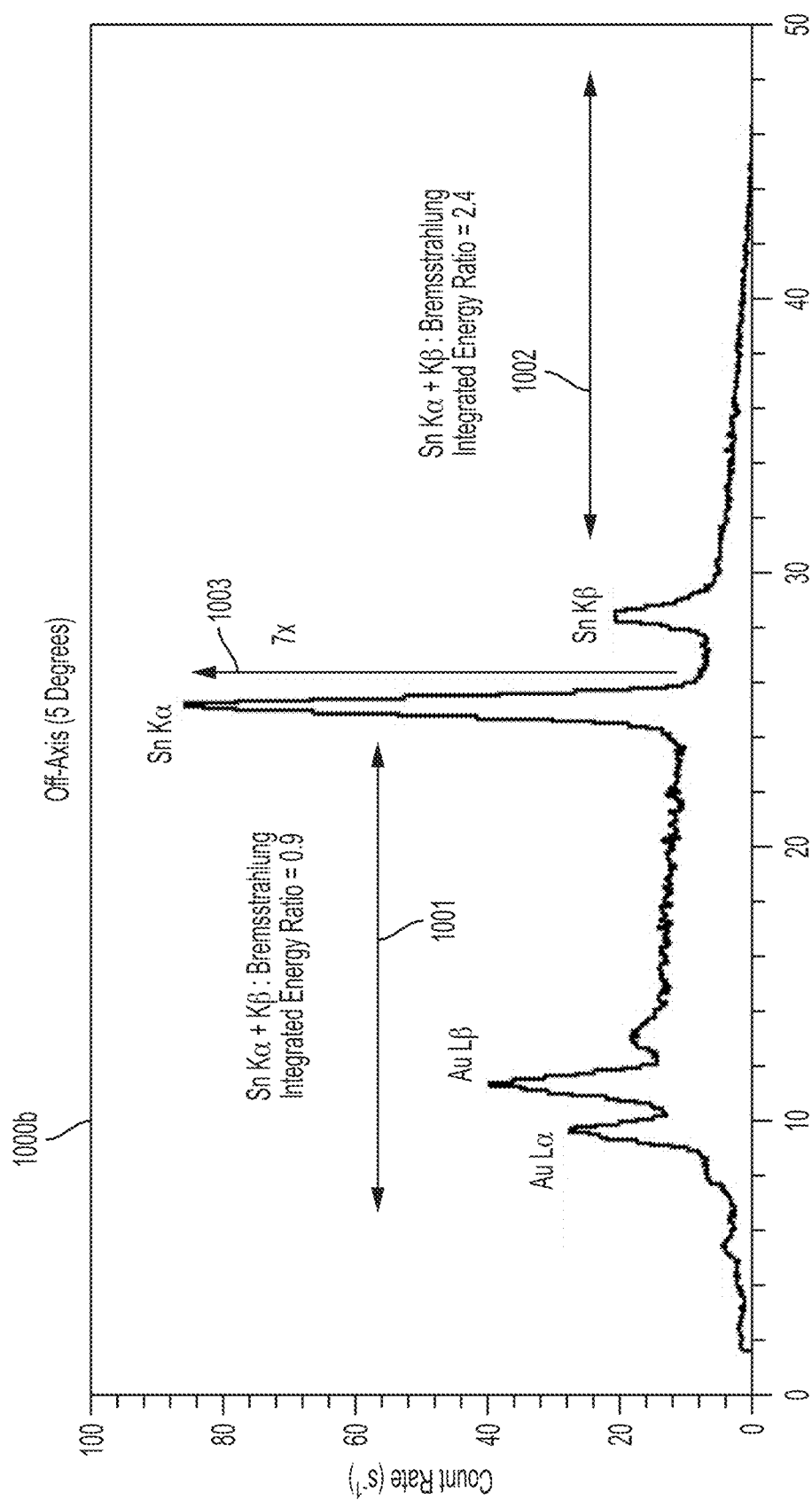

Because the on-axis spectrum and the off-axis spectrum play a role in the efficacy of a monochromatic source, both on-axis and off-axis x-ray spectra are shown. In particular, variation in the monochromaticity of x-ray radiation as a function of the viewing angle $\theta$ results in non-uniformity in the resulting images. In addition, for medical imaging applications, decreases in monochromaticity (i.e., increases in the relative amount of broadband x-ray radiation) of the x-ray spectra at off-axis angles increases the dose delivered to the patient. Thus, the degree of monochromaticity of both on-axis and off-axis spectra may be an important property of the x-ray emission of an x-ray apparatus. In FIG. 10A, on-axis refers to a narrow range of angles about the axis of the x-ray tube (less than approximately 0.5 degrees), and off-axis refers to approximately 5 degrees off the axis of the x-ray tube. As shown in FIGS. 10A and 10B, the x-ray spectrum emitted from the conventional monochromatic x-ray source is not in fact monochromatic and is contaminated with significant amounts of broadband x-ray radiation.

In particular, in addition to the characteristic emission lines of the secondary target (i.e., the monochromatic x-rays emitted via K-shell fluorescence from the tin (Sn) secondary target resulting from transitions from the L and M-shells, labeled as Sn $K_\alpha$ and Sn $K_\beta$ in FIGS. 10A and 10B, respectively), x-ray spectra 1000a and 1000b shown in FIGS. 10A and 10B also include significant amounts of broadband x-ray radiation. Specifically, x-ray spectra 1000a and 1000b include significant peaks at the characteristic emission lines of the primary target (i.e., x-ray radiation at the energies corresponding to K-shell emissions of the gold primary target, labeled as Au Kα and Au Kβ in FIGS. 10A and 10B), as well as significant amounts of Bremsstrahlung background. As indicated by arrows 1003 in FIGS. 10A and 10B, the Sn $K_\alpha$ peak is only (approximately) 8.7 times greater than the Bremsstrahlung background in the on-axis direction and approximately 7 times greater than the Bremsstrahlung background in the off-axis direction. Thus, it is clear from inspection alone that this conventional monochromatic x-ray source emits x-ray radiation exhibiting strikingly poor monochromaticity, both on and off-axis, as quantified below.

Monochromaticity may be computed based on the ratio of the integrated energy in the characteristic fluorescent emission lines of the secondary target to the total integrated energy of the broadband x-ray radiation. For example, the integrated energy of the low energy broadband x-ray radiation (e.g., the integrated energy of the x-ray spectrum below the Sn $K_\alpha$ peak indicated generally by arrows 1001 in FIGS. 10A and 10B), referred to herein as $P_{low}$, and the integrated energy of the high energy broadband x-ray radiation (e.g., the integrated energy of the x-ray spectrum above the Sn $K_\beta$ peak indicated generally by arrows 1002 in FIGS. 10A and 10B), referred to herein as $P_{high}$, may be computed. The ratio of the integrated energy of the characteristic K-shell emission lines (referred to herein as $P_k$, which corresponds to the integrated energy in the Sn $K_\alpha$ and the Sn $K_\beta$ emissions in FIGS. 10A and 10B) to $P_{low}$ and $P_{high}$ provides a measure of the amount of broadband x-ray radiation relative to the amount of monochromatic x-ray radiation emitted by the x-ray source. In the example of FIG. 10A, the ratio $P_k/P_{low}$ is 0.69 and the ratio $P_k/P_{high}$ is 1.7. In the example of FIG. 10B, the ratio $P_k/P_{low}$ is 0.9 and the ratio $P_k/P_{high}$ is 2.4. Increasing the ratios $P_{low}$ and $P_{high}$ increases the degree to which the spectral output of the source is monochromatic. As used herein, the monochromaticity, M, of an x-ray spectrum is computed as $M=1/(1+1/a+1/b)$, where $a=P_k/P_{low}$, $b=P_k/P_{high}$. For the on-axis x-ray spectrum in FIG. 10A produced by the conventional x-ray apparatus, M=0.33, and for the off-axis x-ray spectrum in FIG. 10B produced by the conventional x-ray apparatus, M=0.4. As such, the majority of the energy of the x-ray spectrum is broadband x-ray radiation and not monochromatic x-ray radiation.

Figure 11A:
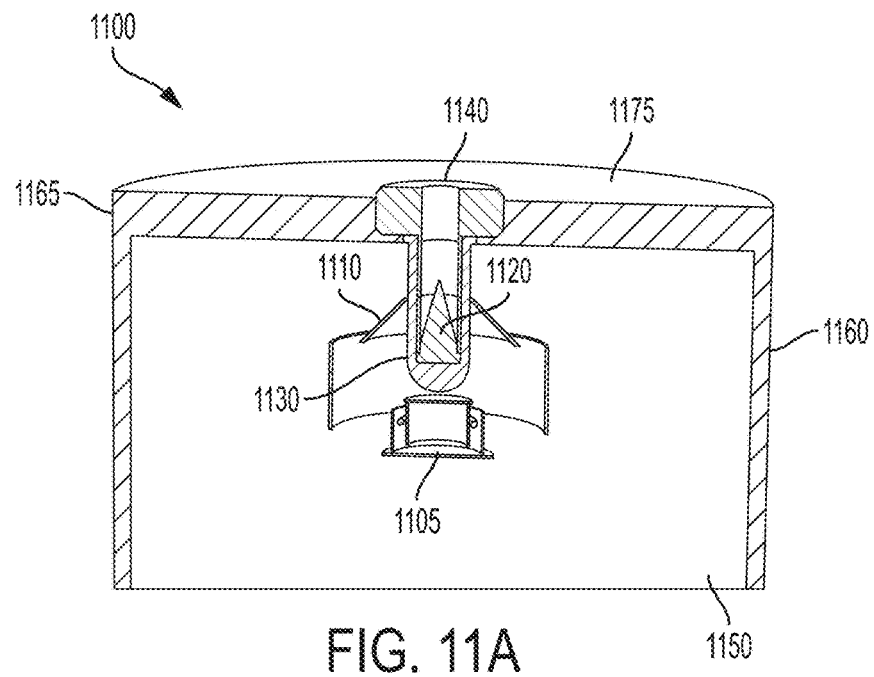
FIG. 11A illustrates a monochromatic x-ray device, in accordance with some embodiments.
Figure 11B:
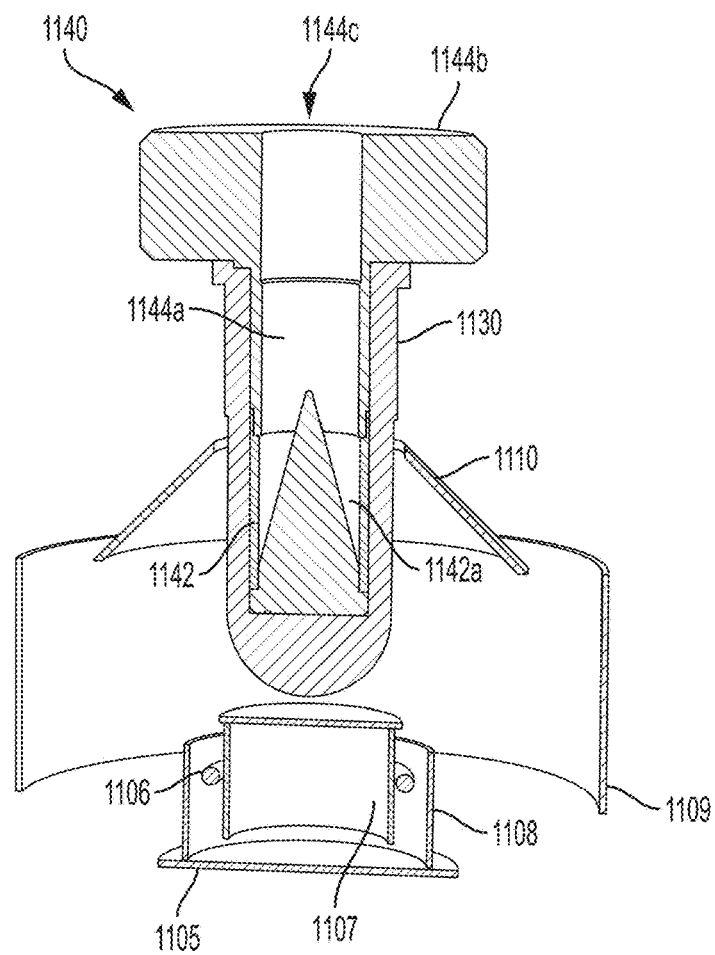
FIG. 11B illustrates a zoomed in view of components of the monochromatic x-ray device illustrated in FIG. 11A.

The inventor has developed techniques that facilitate generating an x-ray radiation having significantly higher monochromaticity, thus improving characteristics of the x-ray emission from an x-ray device and facilitating improved x-ray imaging. FIG. 11A illustrates an x-ray device 1100 incorporating techniques developed by the inventor to improve properties of the x-ray radiation emitted from the device, and FIG. 11B illustrates a zoomed in view of components of the x-ray device 1100, in accordance with some embodiments. X-ray device 1100 comprises a vacuum tube 1150 providing a vacuum sealed enclosure for electron optics 1105 and primary target 1110 of the x-ray device. The vacuum sealed enclosure is formed substantially by a housing 1160 (which includes a front portion 1165) and an interface or window portion 1130. Faceplate 1175 may be provided to form an outside surface of front portion 1165. Faceplate 1175 may be comprised of material that is generally opaque to broadband x-ray radiation, for example, a high Z material such as lead, tungsten, thick stainless steel, tantalum, rhenium, etc. that prevents at least some broadband x-ray radiation from being emitted from x-ray device 1100.

Interface portion 1130 may be comprised of a generally x-ray transmissive material (e.g., beryllium) to allow broadband x-ray radiation from primary target 1110 to pass outside the vacuum enclosure to irradiate secondary target 1120. In this manner, interface portion 1130 provides a "window" between the inside and outside the vacuum enclosure through which broadband x-ray radiation may be transmitted and, as result, is also referred to herein as the window or window portion 1130. Window portion 1130 may comprise an inner surface facing the inside of the vacuum enclosure and an outer surface facing the outside of the vacuum enclosure of vacuum tube 1150 (e.g., inner surface 1232 and outer surface 1234 illustrated in FIG. 12). Window portion 1130 may be shaped to form a receptacle (see receptacle 1235 labeled in FIG. 12) configured to hold secondary target carrier 1140 so that the secondary target (e.g., secondary target 1120) is positioned outside the vacuum enclosure at a location where at least some broadband x-ray radiation emitted from primary target 1110 will impinge on the secondary target. According to some embodiments, carrier 1140 is removable. By utilizing a removable carrier 1140, different secondary targets can be used with x-ray system 1100 without needing to break the vacuum seal, as discussed in further detail below. However, according to some embodiments, carrier 1140 is not removable.

Figure 11C:
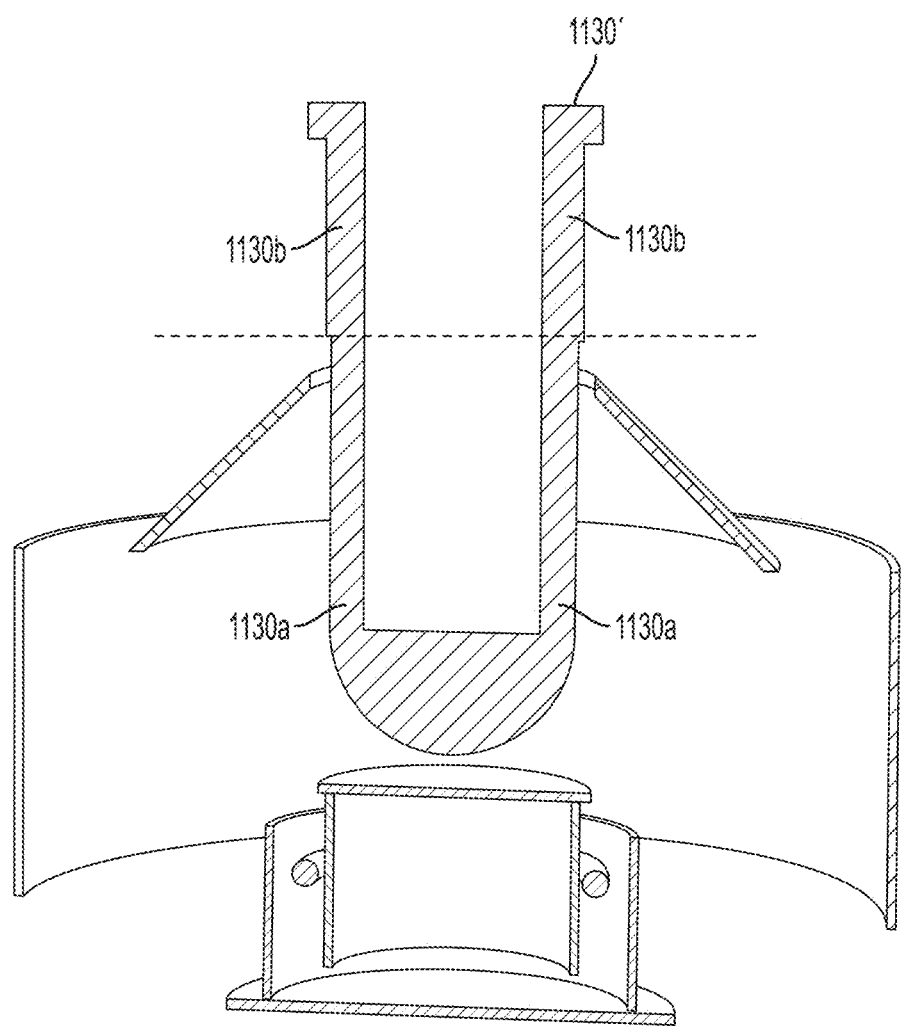
FIG. 11C illustrates a zoomed in view of components of the monochromatic x-ray device illustrate in FIG. 11A using a hybrid material interface portion, in accordance with some embodiments.

The inventor recognized that providing a hybrid interface portion comprising a transmissive portion and a blocking portion facilitates further reducing the amount of broadband x-ray radiation emitted from the x-ray device. For example, FIG. 11C illustrates an interface portion 1130' comprising a transmissive portion 1130a (e.g., a beryllium portion) and a blocking portion 1130b (e.g., a tungsten portion), in accordance with some embodiments. Thus, according to some embodiments, interface portion 1130' may comprise a first material below the dashed line in FIG. 11C and comprise a second material different from the first material above the dashed line. Transmissive portion 1130a and blocking portion 1130b may comprise any respective material suitable for performing intended transmission and absorption function sufficiently, as the aspect are not limited for use with any particular materials.

According to some embodiments, the location of the interface between the transmissive portion and the blocking portion (e.g., the location of the dashed line in FIG. 11C) approximately corresponds to the location of the interface between the transmissive portion and the blocking portion of the carrier when the carrier is inserted into the receptacle formed by the interface portion. According to some embodiments, the location of the interface between the transmissive portion and the blocking portion (e.g., the location of the dashed line in FIG. 11C) does not correspond to the location of the interface between the transmissive portion and the blocking portion of the carrier when the carrier is inserted into the receptacle formed by the interface portion. A hybrid interface component is also illustrated in FIG. 28A, discussed in further detail below.

Figure 19:
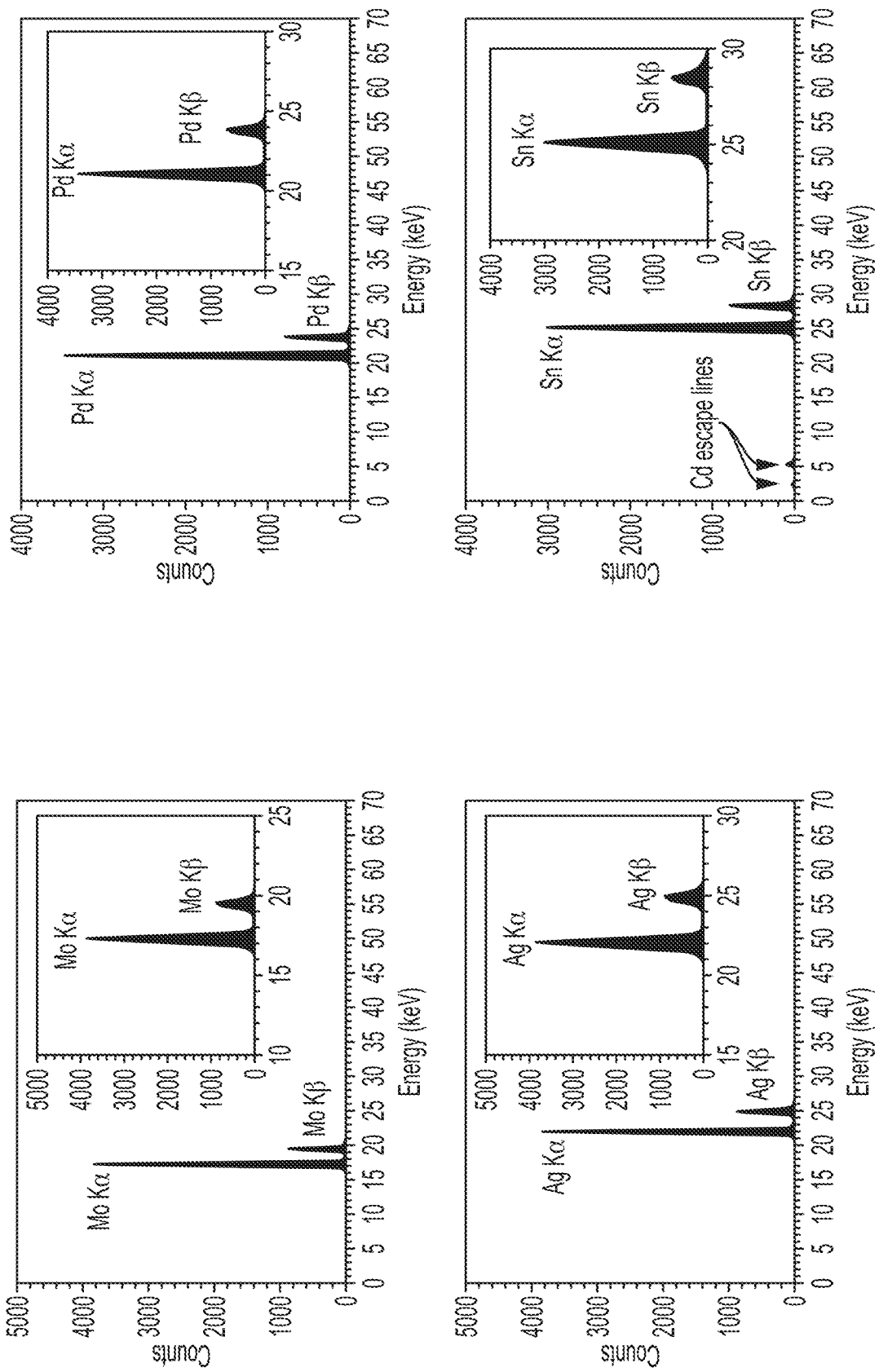
FIG. 19 illustrate fluorescent x-ray spectra of secondary targets of four exemplary materials.

In the embodiment illustrated in FIGS. 11A and 11B, secondary target 1120 has a conical geometry and is made of a material that fluoresces x-rays at desired energies in response to incident broadband x-ray radiation. Secondary target may be made of any suitable material, examples of which include, but are not limited to tin (Sn), silver (Ag), molybdenum (Mo), palladium (Pd), or any other suitable material or combination of materials. FIG. 19 illustrates the x-ray spectra resulting from irradiating secondary target cones of the four exemplary materials listed above. Secondary target 1120 provides a small compact region from which monochromatic x-ray radiation can be emitted via fluorescent to provide good spatial resolution, as discussed in further detail below.

The inventor has appreciated that removable carrier 1140 can be designed to improve characteristics of the x-ray radiation emitted from vacuum tube 1150 (e.g., to improve the monochromaticity of the x-ray radiation emission). Techniques that improve the monochromaticity also facilitate the ability to generate higher intensity monochromatic x-ray radiation, as discussed in further detail below. In the embodiment illustrated in FIGS. 11A and 11B, removable carrier 1140 comprises a transmissive portion 1142 that includes material that is generally transmissive to x-ray radiation so that at least some broadband x-ray radiation emitted by primary target 1110 that passes through window portion 1130 also passes through transmissive portion 1142 to irradiate secondary target 1120. Transmissive portion 1142 may include a cylindrical portion 1142a configured to accommodate secondary target 1120 and may be configured to allow the secondary target to be removed and replaced so that secondary targets of different materials can be used to generate monochromatic x-rays at the different characteristic energies of the respective material, though the aspects are not limited for use with a carrier that allows secondary targets to be interchanged (i.e., removed and replaced). Exemplary materials suitable for transmissive portion 1142 include, but are not limited to, aluminum, carbon, carbon fiber, boron, boron nitride, beryllium oxide, silicon, silicon nitride, etc.

Carrier 1140 further comprises a blocking portion 1144 that includes material that is generally opaque to x-ray radiation (i.e., material that substantially absorbs incident x-ray radiation). Blocking portion 1144 is configured to absorb at least some of the broadband x-ray radiation that passes through window 1130 that is not converted by and/or is not incident on the secondary target and/or is configured to absorb at least some of the broadband x-ray radiation that might otherwise escape the vacuum enclosure. In conventional x-rays sources (e.g., conventional x-ray apparatus 900 illustrated in FIG. 9), significant amounts of broadband x-ray radiation is allowed to be emitted from the apparatus, corrupting the fluorescent x-ray radiation emitted by the secondary target and substantially reducing the monochromaticity of the emitted x-ray radiation. In the embodiments illustrated in FIGS. 11A, 11B, 12, 13A-C and 17A-C, the transmissive portion and the blocking portion form a housing configured to accommodate the secondary target.

Figure 13A:
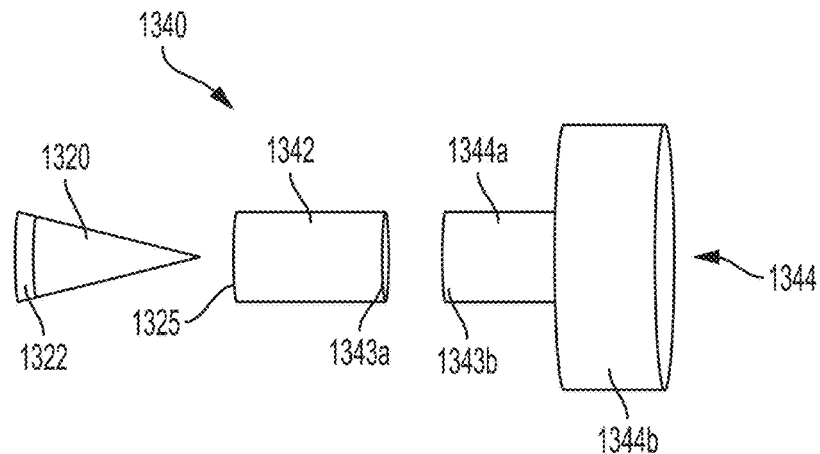
FIGS. 13A, 13B and 13C illustrate views of a secondary target carrier, in accordance with some embodiments.
Figure 13B:
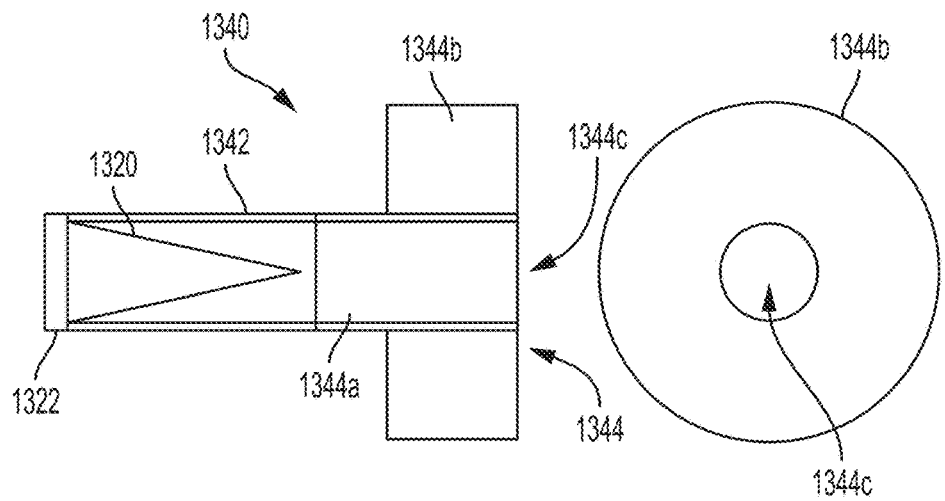
Figure 17A:
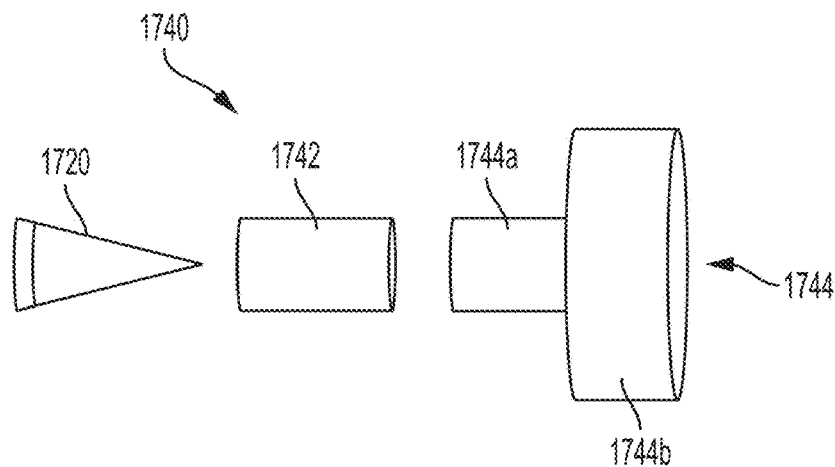
FIGS. 17A, 17B and 17C illustrate views of a secondary target carrier, in accordance with some embodiments.
Figure 17B:
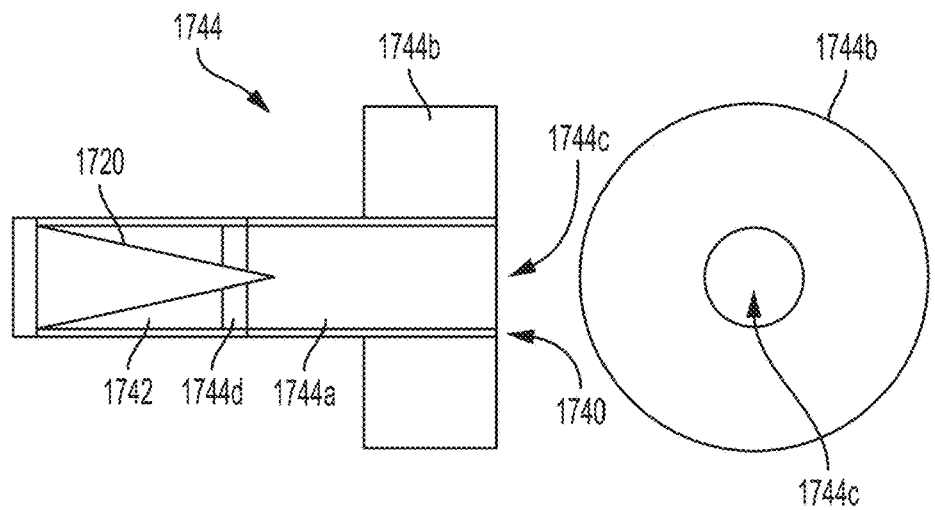

According to some embodiments, blocking portion 1144 includes a cylindrical portion 1144a and an annular portion 1144b. Cylindrical portion 1144a allows x-ray radiation fluoresced by the secondary target 1120 in response to incident broadband x-ray radiation from primary target 1110 to be transmitted, while absorbing at least some broadband x-ray radiation as discussed above. Annular portion 1144b provides a portion providing increased surface area to absorb additional broadband x-ray radiation that would otherwise be emitted by the x-ray device 1100. In the embodiment illustrated in FIGS. 11A and 11B, annular portion 1144b is configured to fit snugly within a recess in the front portion of the x-ray tube to generally maximize the amount of broadband x-ray radiation that is absorbed to the extent possible. Annular portion 1144b includes an aperture portion 1144c that corresponds to the aperture through cylindrical portions 1144b and 1142a to allow monochromatic x-ray radiation fluoresced from secondary target 1120 to be emitted from x-ray device 1100, as also shown in FIGS. 13B and 17B discussed below. Exemplary materials suitable for blocking portion 1144 include, but are not limited to, lead, tungsten, tantalum, rhenium, platinum, gold, etc.

In the embodiment illustrated FIGS. 11A and 11B, carrier 1140 is configured so that a portion of the secondary target is contained within blocking portion 1144. Specifically, as illustrated in the embodiment shown in FIGS. 11A and 11B, the tip of conical secondary target 1120 extends into cylindrical portion 1144b when the secondary target is inserted into transmissive portion 1142 of carrier 1140. The inventor has appreciated that having a portion of the secondary target contained within blocking portion 1144 improves characteristics of the monochromatic x-ray radiation emitted from the x-ray device, as discussed in further below. However, according to some embodiments, a secondary target carrier may be configured so that no portion of the secondary target is contained with the blocking portion of the carrier, examples of which are illustrated FIGS. 13A-C discussed in further detail below. Both configurations of carrier 1140 (e.g., with and without blocking overlap of the secondary target carrier) provide significant improvements to characteristics of the emitted x-ray radiation (e.g., improved monochromaticity), as discussed in further detail below.

Figure 12:
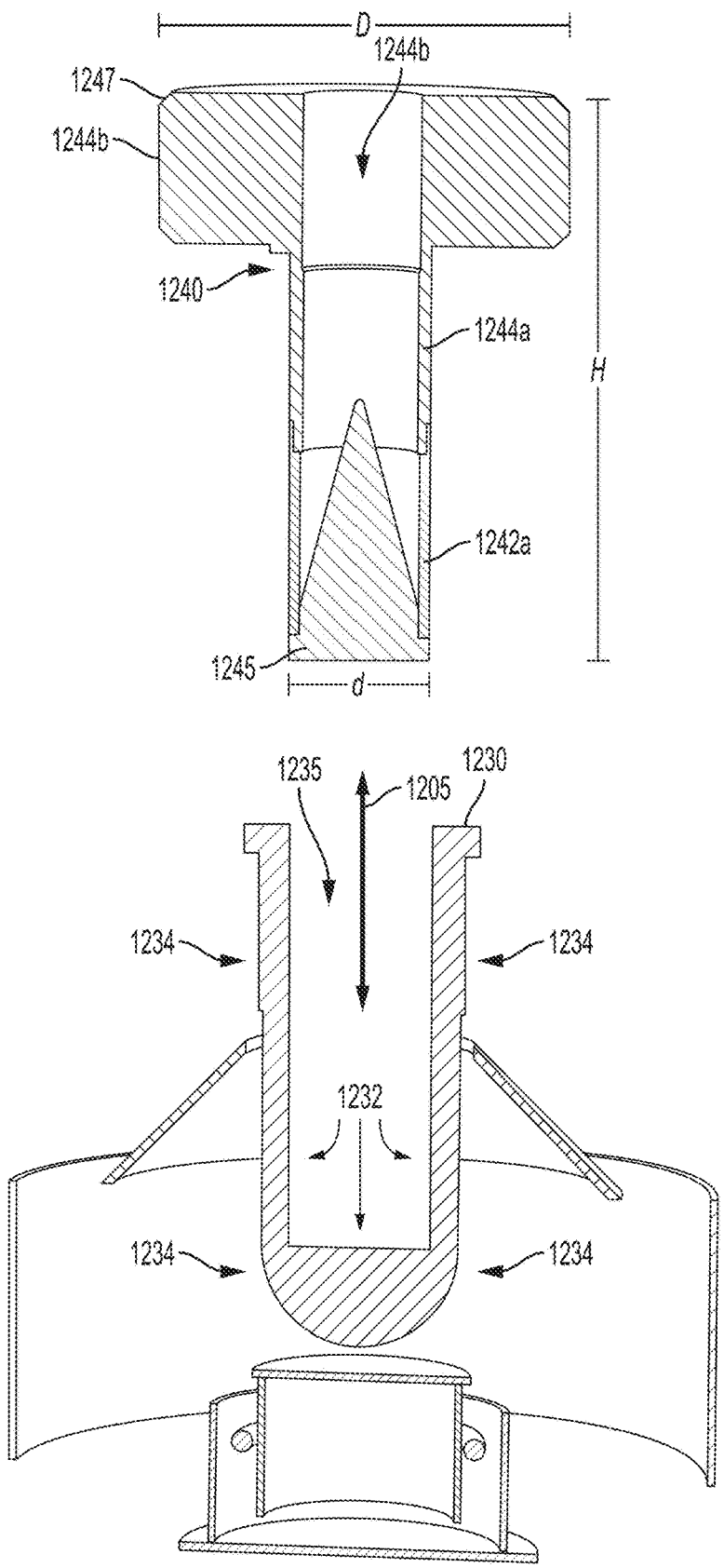
FIG. 12 illustrates a removeable carrier configured to be inserted and capable of being removed from a receptacle of a monochromatic x-ray device.

As illustrated in FIG. 12, carrier 1240 (which may be similar or the same as carrier 1140 illustrated in FIGS. 11A and 11B) is configured to be removeable. For example, carrier 1240 may be removeably inserted into receptacle 1235 formed by interface component 1230 (e.g., an interface comprising a transmissive window), for example, by inserting and removing the carrier, respectively, in the directions generally indicated by arrow 1205. That is, according to some embodiments, carrier 1240 is configured as a separate component that can be inserted into and removed from the x-ray device (e.g., by inserting removeable carrier 1240 into and/or removing the carrier from receptacle 1235).

As shown in FIG. 12, carrier 1240 has a proximal end 1245 configured to be inserted into the x-ray device and a distal end 1247 from which monochromatic x-ray radiation is emitted via aperture 1244d through the center of carrier 1240. In the embodiment illustrated in FIG. 12, cylindrical blocking portion 1244a is positioned adjacent to and distally from cylindrical transmissive portion 1242a. Annular blocking portion 1244b is positioned adjacent to and distally from block portion 1244a. As shown, annular blocking portion 1244b has a diameter D that is larger than a diameter d of the cylindrical blocking portion 1244a (and cylindrical transmissive portion 1242a for embodiments in which the two cylindrical portions have approximately the same diameter). The distance from the extremes of the proximal end and the distal end is labeled as height H in FIG. 12. The dimensions of carrier 1240 may depend on the dimensions of the secondary target that the carrier is configured to accommodate. For example, for an exemplary carrier 1240 configured to accommodate a secondary target having a 4 mm base, diameter d may be approximately 4-5 mm, diameter D may be approximately 13-16 mm, and height H may be approximately 18-22 mm. As another example, for an exemplary carrier 1240 configured to accommodate a secondary target having a 8 mm base, diameter d may be approximately 8-9 mm, diameter D may be approximately 18-22 mm, and height H may be approximately 28-32 mm. It should be appreciated that the dimensions for the carrier and the secondary target provided are merely exemplary, and can be any suitable value as the aspect are not limited for use with any particular dimension or set of dimensions.

According to some embodiments, carrier 1240 may be configured to screw into receptacle 1235, for example, by providing threads on carrier 1240 capable of being hand screwed into cooperating threads within receptacle 1235. Alternatively, a releasable mechanical catch may be provided to allow the carrier 1240 to be held in place and allows the carrier 1240 to be removed by applying force outward from the receptacle. As another alternative, the closeness of the fit of carrier 1240 and receptacle 1235 may be sufficient to hold the carrier in place during operation. For example, friction between the sides of carrier 1240 and the walls of receptacle 1235 may be sufficient to hold carrier 1240 in position so that no additional fastening mechanism is needed. It should be appreciated that any means sufficient to hold carrier 1240 in position when the carrier is inserted into the receptacle may be used, as the aspects are not limited in this respect.

As discussed above, the inventor has developed a number of carrier configuration that facilitate improved monochromatic x-ray radiation emission. FIGS. 13A and 13B illustrate a three-dimensional and a two-dimensional view of a carrier 1340, in accordance with some embodiments. The three-dimensional view in FIG. 13A illustrates carrier 1340 separated into exemplary constituent parts. In particular, FIG. 13A illustrates a transmissive portion 1342 separated from a blocking portion 1344. As discussed above, transmissive portion 1342 may include material that generally transmits broadband x-ray radiation at least at the relevant energies of interest (i.e., material that allows broadband x-ray radiation to pass through the material without substantial absorption at least at the relevant energies of interest, such as aluminum, carbon, carbon fiber, boron, boron nitride, beryllium oxide, silicon, silicon nitride, etc. Blocking portion 1344, on the other hand, may include material that is generally opaque to broadband x-ray radiation at least at the relevant energies of interest (i.e., material that substantially absorbs broadband x-ray radiation at least at the relevant energies of interest, such as lead, tungsten, tantalum, rhenium, platinum, gold, etc.

In this way, at least some broadband x-ray radiation emitted by the primary target is allowed to pass through transmissive portion 1342 to irradiate the secondary target, while at least some broadband x-ray radiation emitted from the primary target (and/or emitted from or scattered by other surfaces of the x-ray tube) is absorbed by blocking portion 1344 to prevent unwanted broadband x-ray radiation from being emitted from the x-ray device. As a result, carrier 1340 facilitates providing monochromatic x-ray radiation with reduced contamination by broadband x-ray radiation, significantly improving monochromaticity of the x-ray emission of the x-ray device. In the embodiments illustrated in FIGS. 13A-C, blocking portion 1344 includes a cylindrical portion 1344a and annular portion 1344b having a diameter greater than cylindrical portion 1344a to absorb broadband x-ray radiation emitted over a wider range of angles and/or originating from a wider range of locations to improve the monochromaticity of the x-ray radiation emission of the x-ray device.

According to some embodiments, transmissive portion 1342 and blocking portion 1344 may be configured to couple together or mate using any of a variety of techniques. For example, the transmissive portion 1342, illustrated in the embodiment of FIG. 13A as a cylindrical segment, may include a mating portion 1343a at one end of the cylindrical segment configured to mate with mating portion 1342b at a corresponding end of cylindrical portion 1344a of blocking portion 1344. Mating portion 1343a and 1343b may be sized appropriately and, for example, provided with threads to allow the transmissive portion 1342 and the blocking portion 1344 to be mated by screwing the two portion together. Alternatively, mating portion 1343a and 1343b may be sized so that mating portion 1343a slides over mating portion 1343b, or vice versa, to couple the two portions together. It should be appreciated that any mechanism may be used to allow transmissive portion 1342 and blocking portion 1344 to be separated and coupled together. According to some embodiments, transmissive portion 1342 and blocking portion 1344 are not separable. For example, according to some embodiments, carrier 1340 may be manufactured as a single component having transmissive portion 1342 fixedly coupled to blocking portion 1344 so that the portions are not generally separable from one another as a general matter of course.

Transmissive portion 1342 may also include portion 1325 configured to accommodate secondary target 1320. For example, one end of transmissive portion 1342 may be open and sized appropriately so that secondary target 1320 can be positioned within transmissive portion 1342 so that, when carrier 1340 is coupled to the x-ray device (e.g., inserted into a receptacle formed by an interface portion of the vacuum tube, such as a transmissive window or the like), secondary target 1320 is positioned so that at least some broadband x-ray radiation emitted from the primary target irradiates secondary target 1320 to cause secondary target to fluoresce monochromatic x-rays at the characteristic energies of the selected material. In this way, different secondary targets 1320 can be positioned within and/or held by carrier 1340 so that the energy of the monochromatic x-ray radiation is selectable. According to some embodiments, secondary target 1320 may include a portion 1322 that facilitates mating or otherwise coupling secondary target 1320 to the carrier 1340. For example, portions 1322 and 1325 may be provide with cooperating threads that allow the secondary target to be screwed into place within the transmissive portion 1342 of carrier 1340. Alternatively, portions 1322 and 1325 may be sized so that the secondary target fits snuggly within transmissive portion and is held by the closeness of the fit (e.g., by the friction between the two components) and/or portion 1322 and/or portion 1325 may include a mechanical feature that allows the secondary target to held into place. According to some embodiments, a separate cap piece may be included to fit over transmissive portion 1342 after the secondary target has been inserted into the carrier and/or any other suitable technique may be used to allow secondary target 1320 to be inserted within and sufficiently held by carrier 1340, as the aspects are not limited in this respect.

In the embodiment illustrated in FIG. 13B, secondary target 1320 is contained within transmissive portion 1342, without overlap with blocking portion 1344. That is, the furthest extent of secondary target 1320 (e.g., the tip of the conical target in the embodiment illustrated in FIG. 13B) does not extend into cylindrical portion 1344a of the blocking portion (or any other part of the blocking portion). By containing secondary target 1320 exclusively within the transmissive portion of the carrier, the volume of secondary target 1320 exposed to broadband x-ray radiation and thus capable of fluorescing monochromatic x-ray radiation may be generally maximized, providing the opportunity to generally optimize the intensity of the monochromatic x-ray radiation produced for a given secondary target and a given set of operating parameters of the x-ray device (e.g., power levels of the x-ray tube, etc.). That is, by increasing the exposed volume of the secondary target, increased monochromatic x-ray intensity may be achieved.

The front view of annular portion 1344b of blocking portion 1334 illustrated in FIG. 13B illustrates that annular portion 1344b includes aperture 1344c corresponding to the aperture of cylindrical portion 1344a (and cylindrical portion 1342) that allows monochromatic x-rays fluoresced from secondary target 1320 to be emitted from the x-ray device. Because blocking portion 1344 is made from a generally opaque material, blocking portion 1344 will also absorb some monochromatic x-rays fluoresced from the secondary target emitted at off-axis angles greater than some threshold angle, which threshold angle depends on where in the volume of the secondary target the monochromatic x-rays originated. As such, blocking portion 1344 also operates as a collimator to limit the monochromatic x-rays emitted to a range of angles relative to the axis of the x-ray tube, which in the embodiments in FIGS. 13A-C, corresponds to the longitudinal axis through the center of carrier 1340.

Figure 13C:
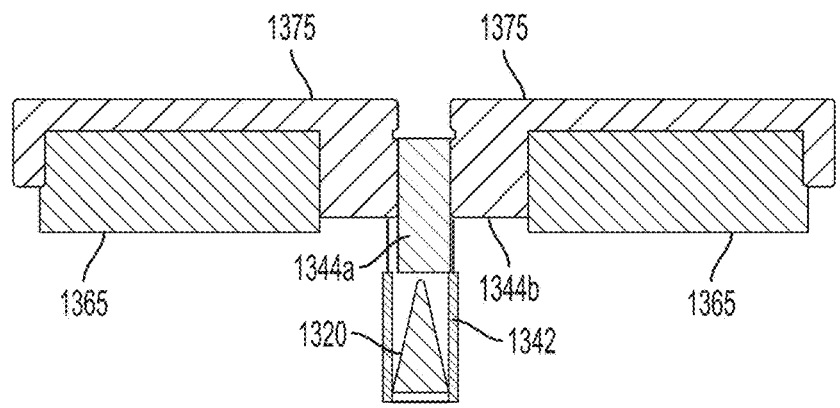

FIG. 13C illustrates a schematic of carrier 1340 positioned within an x-ray device (e.g., inserted into a receptacle formed by an interface portion of the vacuum tube, such as exemplary window portions 1130 and 1230 illustrated in FIGS. 11A, 11B and 12). Portions 1365 correspond to the front portion of the vacuum tube, conventionally constructed of a material such as copper. In addition, a cover or faceplate 1375 made of a generally opaque material (e.g., lead, tungsten, tantalum, rhenium, platinum, gold, etc.) is provided having an aperture corresponding to the aperture of carrier 1340. Faceplate 1375 may be optionally included to provide further absorption of broadband x-ray to prevent spurious broadband x-ray radiation from contaminating the x-ray radiation emitted from the x-ray device.

Figure 14A:
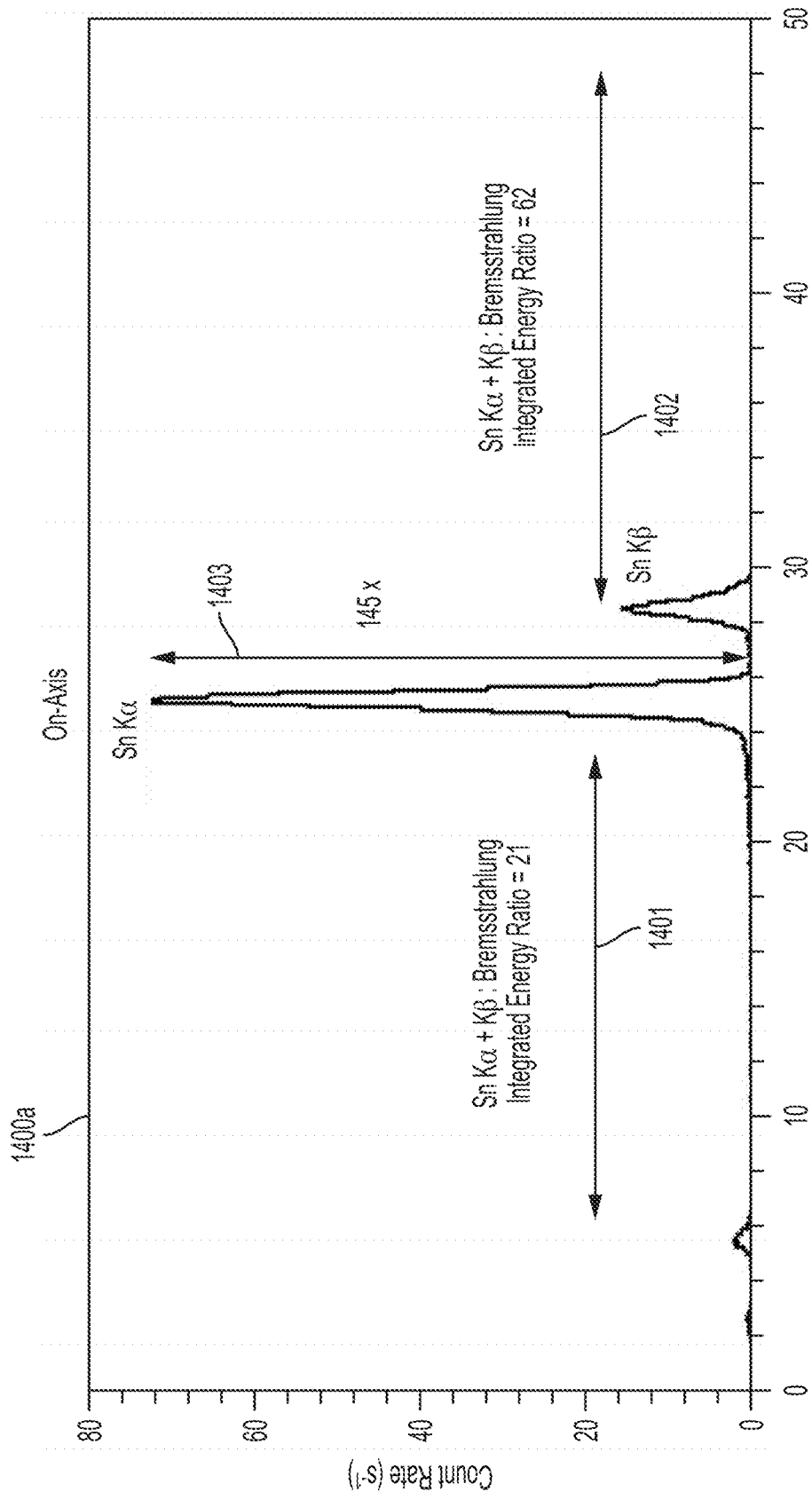
FIGS. 14A and 14B illustrate on-axis and off-axis x-ray spectra of x-ray radiation emitted from a monochromatic x-ray apparatus using the exemplary carrier illustrated in FIGS. 13A, 13B and 13C.
Figure 14B:
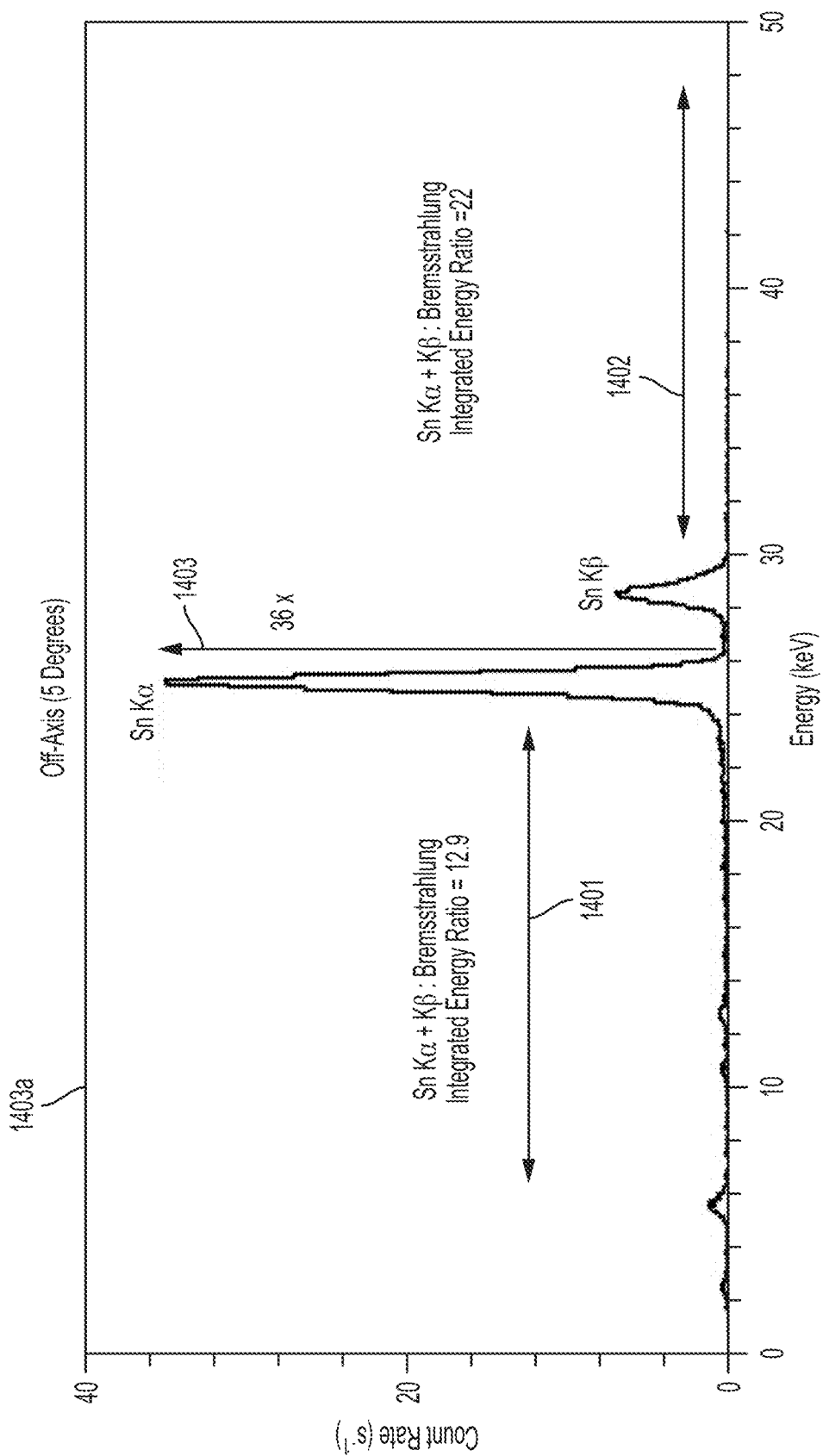

According to some embodiments, exemplary carrier 1340 may be used to improve monochromatic x-ray emission characteristics. For example, FIGS. 14A and 14B illustrate the on-axis x-ray spectrum 1400a and off-axis x-ray spectrum 1400b resulting from the use of carrier 1340 illustrated in FIGS. 13A, 13B and/or 13C. As shown, the resulting x-ray spectrum is significantly improved relative to the on-axis and off-axis x-ray spectra shown in FIGS. 10A and 10B that was produced by a conventional x-ray apparatus configured to produce monochromatic x-ray radiation (e.g., conventional x-ray apparatus 900 illustrated in FIG. 9). As indicated by arrow 1403 in FIG. 14A, the on-axis Sn $K_\alpha$ peak is approximately 145 times greater than the Bremsstrahlung background, up from approximately 8.7 in the on-axis spectrum illustrated in FIG. 10A. The off-axis Sn $K_\alpha$ peak is approximately 36 times greater than the Bremsstrahlung background as indicated by arrow 1403 in FIG. 14B, up from approximately 7.0 in the off-axis spectrum illustrated in FIG. 14B. In addition, the ratios of $P_k$ (the integrated energy of the characteristic K-shell emission lines, labeled as Sn $K_\alpha$ and Sn $K_\beta$ in FIGS. 14A and 14B) to $P_{low}$ (the integrated energy of the low energy x-ray spectrum below the Sn $K_\alpha$ peak, indicated generally by arrows 1401 in FIGS. 14A and 14B) and $P_{high}$ (the integrated energy of the high energy spectrum above the Sn $K_\beta$ peak, indicated generally by arrows 1402) are 21 and 62, respectively, for the on-axis spectrum illustrated in FIG. 14A, up from 0.69 and 1.7 for the on-axis spectrum of FIG. 10A. The ratios $P_k/P_{low}$ and $P_k/P_{high}$ are 12.9 and 22, respectively, for the off-axis spectrum illustrated in FIG. 14B, up from 0.9 and 2.4 for the off-axis spectrum of FIG. 10B. These increased ratios translate to an on-axis monochromaticity of 0.94 (M=0.94) and an off-axis monochromaticity of 0.89 (M=0.89), up from an on-axis monochromaticity of 0.33 and an off-axis monochromaticity of 0.4 for the x-ray spectrum of FIGS. 10A and 10B, respectively.

Figure 14C:
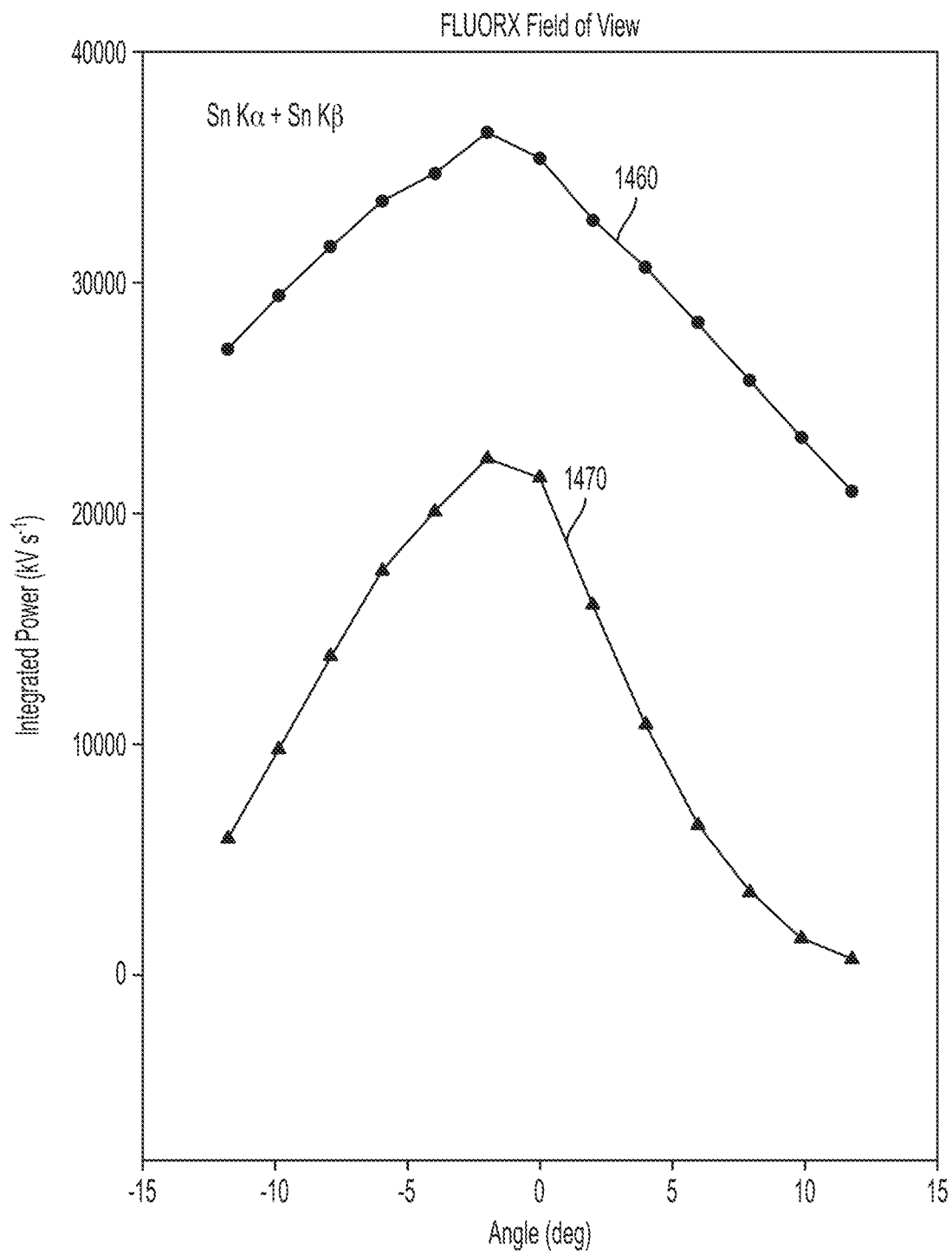
FIG. 14C illustrates field of view characteristic of the x-ray spectra illustrated in FIGS. 10A-B and FIGS. 14A-14B.
Figure 15:
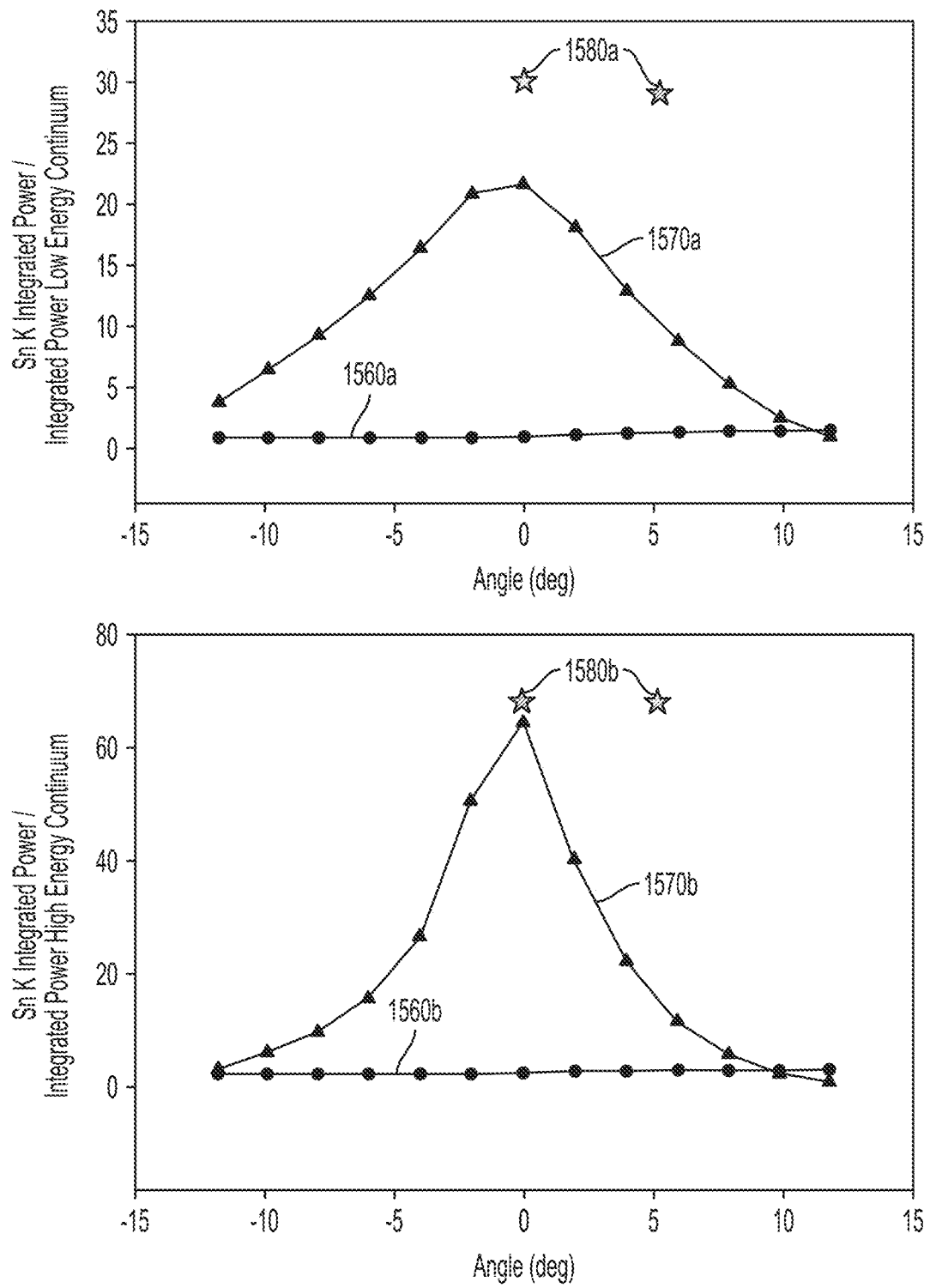
FIG. 15 illustrates integrated power ratios in the low and high energy spectra as a function of viewing angle.
Figure 16:
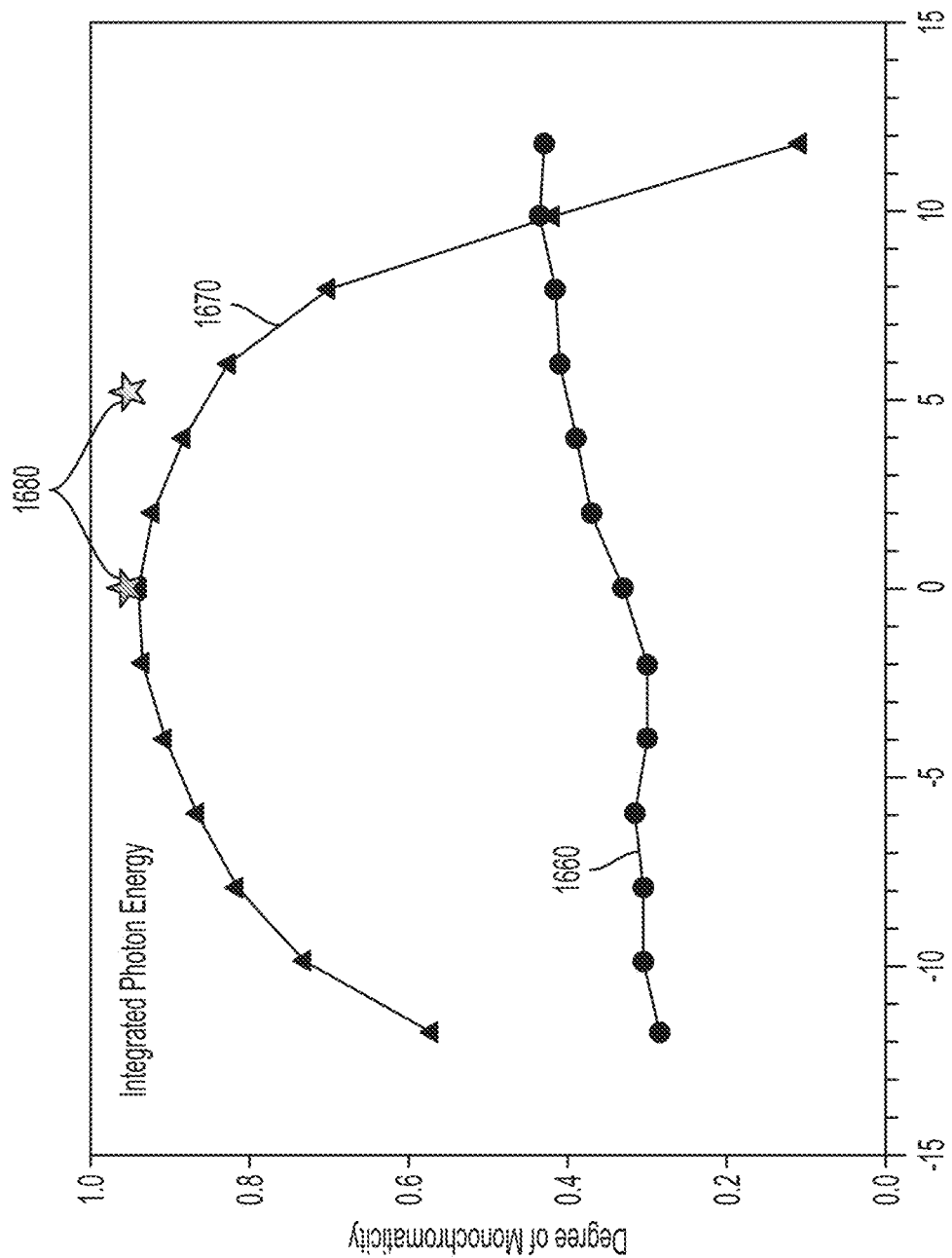
FIG. 16 illustrates monochromaticity as a function of viewing angle.

This significant improvement in monochromaticity facilitates acquiring x-ray images that are more uniform, have better spatial resolution and that deliver significantly less x-ray radiation dose to the patient in medical imaging applications. For example, in the case of mammography, the x-ray radiation spectrum illustrated in FIGS. 10A and 10B would deliver four times the mean glandular dose to normal thickness and density breast tissue than would be delivered by the x-ray radiation spectrum illustrated in FIGS. 14A and 14B. FIG. 14C illustrates the field of view of the conventional x-ray source used to generate the x-ray spectrum illustrated in FIGS. 10A and 10B along with the field of view of the x-ray device used to generate the x-ray spectrum illustrated in FIGS. 14A and 14B. The full width at half maximum (FWHM) of the conventional x-ray apparatus is approximately 30 degrees, while the FWHM of the improved x-ray device is approximately 15 degrees. Accordingly, although the field of view is reduced via exemplary carrier 1340, the resulting field of view is more than sufficient to image an organ such as the breast in a single exposure at compact source detector distances (e.g., approximately 760 mm), but with increased uniformity and spatial resolution and decreased radiation dose, allowing for significantly improved and safer x-ray imaging. FIG. 15 illustrates the integrated power ratios for the low and high energy x-ray radiation ($P_k/P_{low}$ and $P_k/P_{high}$) as a function of the viewing angle θ and FIG. 16 illustrates the monochromaticity of the x-ray radiation for the conventional x-ray apparatus (1560a, 1560b and 1660) and the improved x-ray apparatus using exemplary carrier 1340 (1570a, 1570b and 1670). As shown by plots 1570a, 1570b and 1670, monochromaticity decreases as a function of viewing angle. Using carrier 1340, monochromatic x-ray radiation is emitted having a monochromaticity of at least 0.7 across a 15 degree field of view and a monochromaticity of at least 0.8 across a 10 degree field of view about the longitudinal axis. As shown by plots 1560a, 1560b and 1660, monochromaticity of the conventional x-ray apparatus is extremely poor across all viewing angles (i.e., less than 0.4 across the entire field of view).

The inventor has appreciated that further improvements to aspects of the monochromaticity of x-ray radiation emitted from an x-ray tube may be improved by modifying the geometry of the secondary target carrier. According to some embodiments, monochromaticity may be dramatically improved, in particular, for off-axis x-ray radiation. For example, the inventor recognized that by modifying the carrier so that a portion of the secondary target is within a blocking portion of the carrier, the monochromaticity of x-ray radiation emitted by an x-ray device may be improved, particularly with respect to off-axis x-ray radiation. FIGS. 17A and 17B illustrate a three-dimensional and a two-dimensional view of a carrier 1740, in accordance with some embodiments. Exemplary carrier 1740 may include similar parts to carrier 1340, including a transmissive portion 1742 to accommodate secondary target 1720, and a blocking portion 1744 (which may include a cylindrical portion 1744a and annular portion 1744b with an aperture 1744c through the center), as shown in FIG. 17A.

Figure 17C:
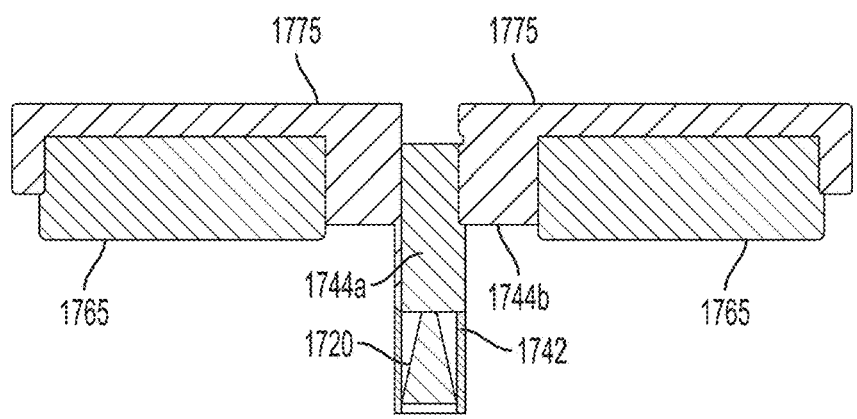

However, in the embodiment illustrated in FIGS. 17A-C, carrier 1740 is configured so that, when secondary target 1720 is positioned within transmissive portion 1742, a portion of secondary target 1720 extends into blocking portion 1744. In particular, blocking portion includes an overlap portion 1744d that overlaps part of secondary target 1720 so that at least some of the secondary target is contained within blocking portion 1744. According to some embodiments, overlap portion 1744d extends over between approximately 0.5 and 5 mm of the secondary target. According to some embodiments, overlap portion 1744d extends over between approximately 1 and 3 mm of the secondary target. According to some embodiments, overlap portion 1744d extends over approximately 2 mm of the secondary target. According to some embodiments, overlap portion 1744d extends over less than 0.5 mm, and in some embodiments, overlap portion 1744d extends over greater than 5 mm. The amount of overlap will depend in part on the size and geometry of the secondary target, the carrier and the x-ray device. FIG. 17C illustrates carrier 1740 positioned within an x-ray device (e.g., inserted in a receptacle formed at the interface of the vacuum tube), with a faceplate 1775 provided over front portion 1765 of a vacuum tube (e.g., vacuum tube 1150 illustrated in FIG. 11A).

Figure 7:
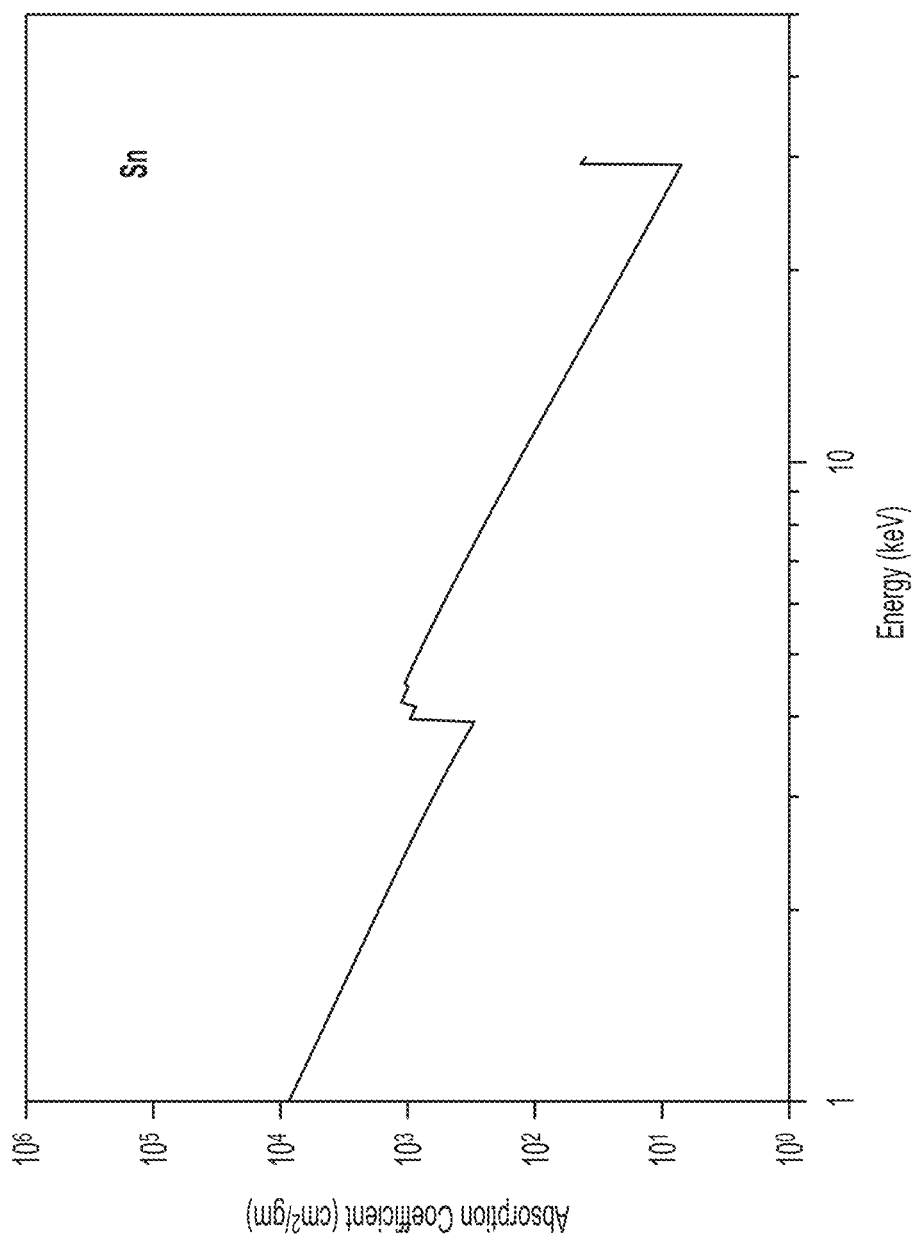
FIG. 7 illustrates the absorption coefficient as a function of x-ray energy for tin, wherein the discontinuous jumps or edges show how the absorption is enhanced just above the binding energies of the electrons in tin.
Figure 8:
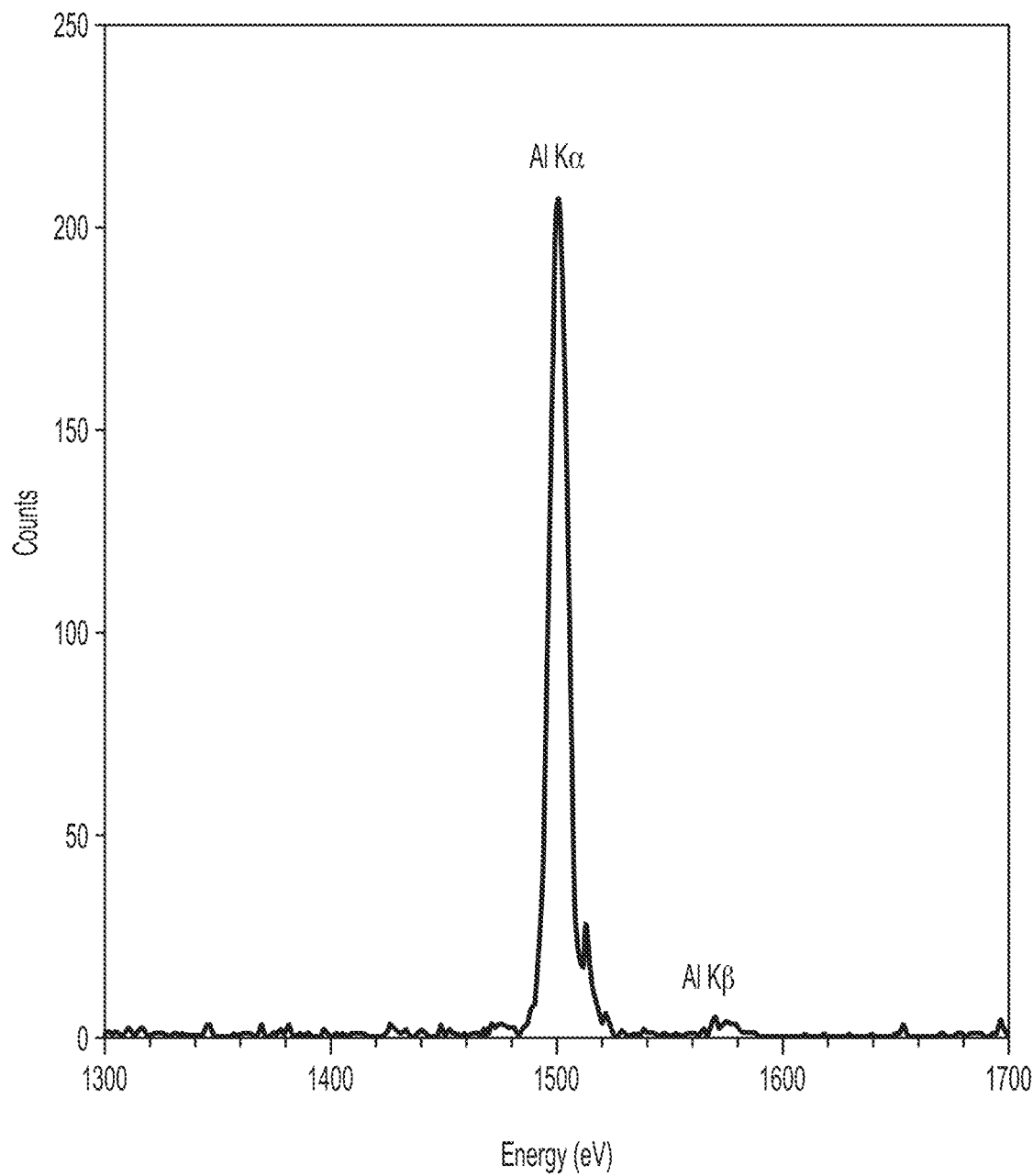
FIG. 8 illustrates an X-Ray fluorescence spectrum made by irradiating a target of aluminum (Al) with copper x-rays which were generated by an x-ray tube with an anode of copper.
Figure 18A:
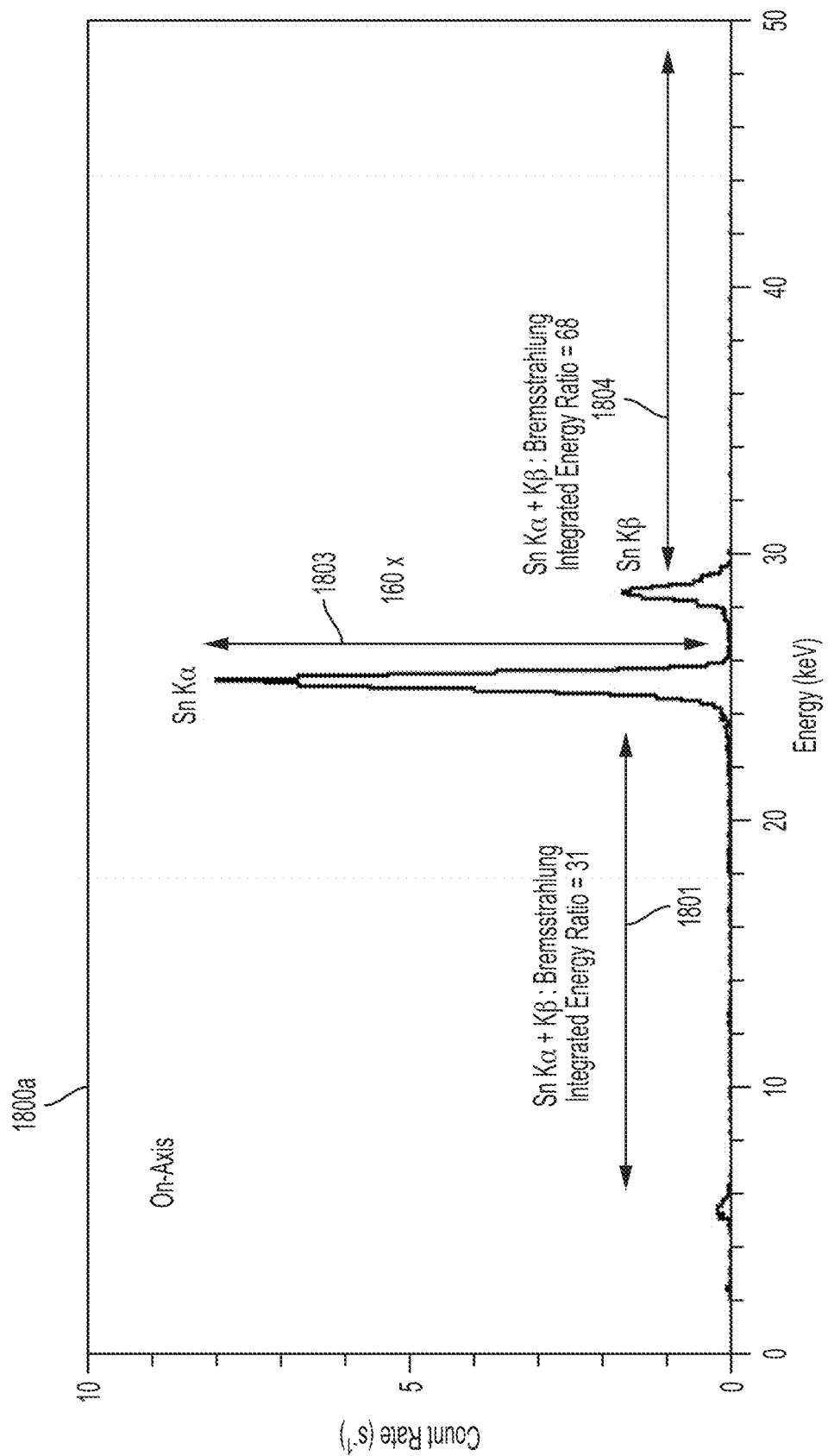
FIGS. 18A and 18B illustrate on-axis and off-axis x-ray spectra of x-ray radiation emitted from a monochromatic x-ray apparatus using the exemplary carrier illustrated in FIGS. 17A, 17B and 17C.
Figure 18B:
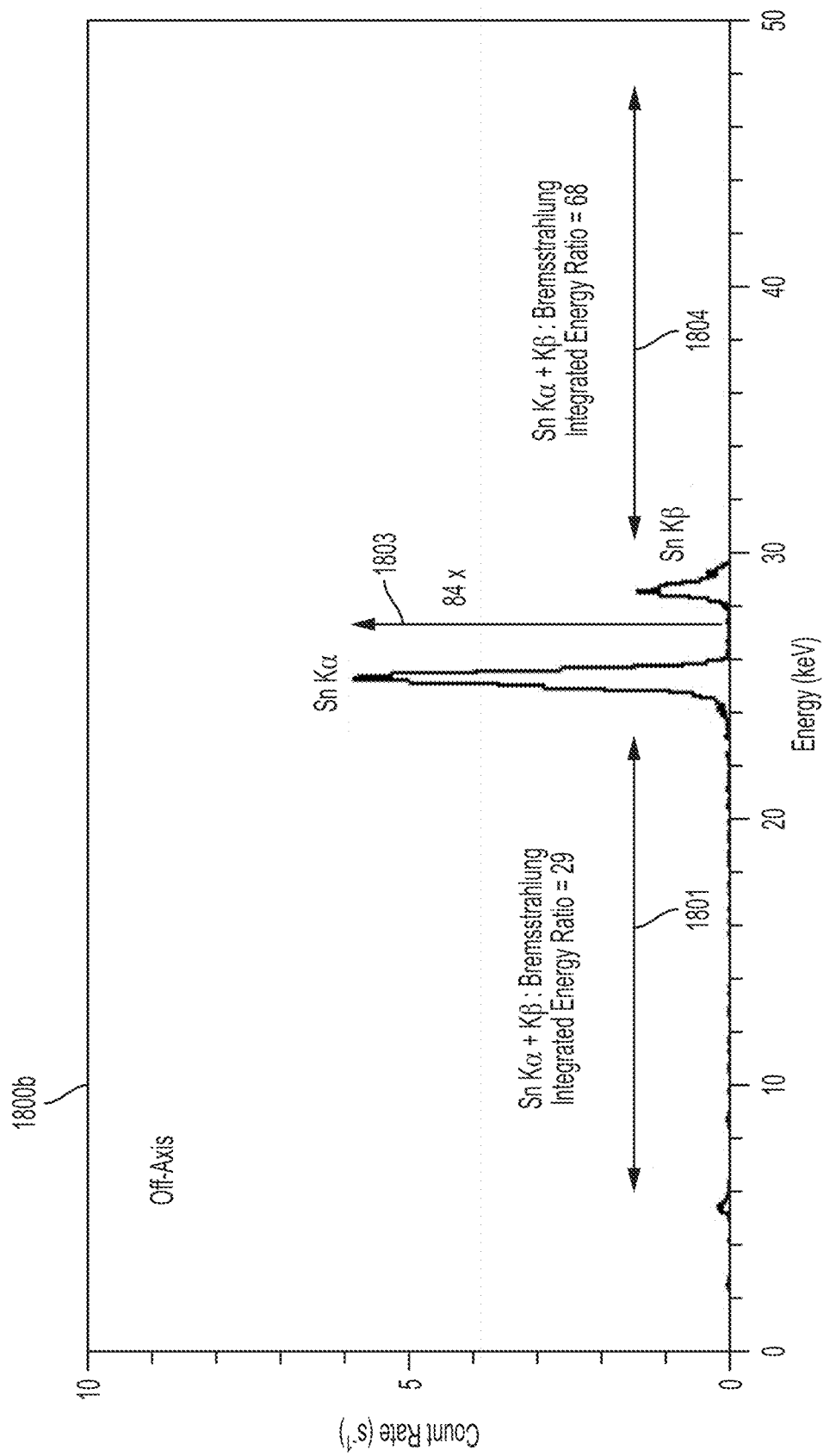

According to some embodiments, exemplary carrier 1740 may be used to further improve monochromatic x-ray emission characteristics. For example, FIGS. 18A and 18B illustrate the on-axis x-ray spectrum 1800a and off-axis x-ray spectrum 1800b resulting from the use of carrier 1740 illustrated in FIGS. 17A-C. As shown, the resulting x-ray spectrum are significantly improved relative to the on-axis and off-axis x-ray spectrum produced the conventional x-ray apparatus shown in FIGS. 10A and 10B, as well as exhibiting improved characteristics relative to the x-ray spectra produced using exemplary carrier 1340 illustrated in FIGS. 13A-C. As indicated by arrow 1803 in FIG. 18A, the on-axis Sn $K_\alpha$ peak is 160 times greater than the Bremsstrahlung background, compared to 145 for the on-axis spectrum in FIG. 14A and 8.7 for the on-axis spectrum illustrated in FIG. 10A. As indicated by arrow 1803 in FIG. 18B, the off-axis Sn $K_\alpha$ peak is 84 times greater than the Bremsstrahlung background, compared to 36 for the off-axis spectrum in FIG. 14B and 7.0 for the off-axis spectrum illustrated in FIG. 10B.

The ratios of $P_k$ (the integrated energy of the characteristic K-shell emission lines, labeled as Sn $K_\alpha$ and Sn $K_\beta$ in FIGS. 18A and 18B) to $P_{low}$ (the integrated energy of the low energy x-ray spectrum below the Sn $K_\alpha$ peak, indicated generally by arrows 1801 in FIGS. 18A and 18B) and $P_{high}$ (the integrated energy of the high energy spectrum above the Sn $K_\beta$ peak, indicated generally by arrows 1802) are 31 and 68, respectively, for the on-axis spectrum illustrated in FIG. 18A, compared to 21 and 62 for the on-axis spectrum of FIG. 14A and 0.69 and 1.7 for the on-axis spectrum of FIG. 10A. The ratios $P_k/P_{low}$ and $P_k/P_{high}$ are 29 and 68, respectively, for the off-axis spectrum of FIG. 18B, compared to 12.9 and 22, respectively, for the off-axis spectrum illustrated in FIG. 14B and 0.9 and 2.4 for the off-axis spectrum of FIG. 10B. These increased ratios translate to an on-axis monochromaticity of 0.96 (M=0.96) and an off-axis monochromaticity of 0.95 (M=0.95), compared to an on-axis monochromaticity of 0.94 (M=0.94) for x-ray spectrum of FIG. 14A and an off-axis monochromaticity of 0.89 (M=0.89) for the x-ray spectrum of FIG. 14B, and an on-axis monochromaticity of 0.33 and an off-axis monochromaticity of 0.4 for the x-ray spectra of FIGS. 10A and 10B, respectively.

Referring again to FIGS. 15 and 16, the stars indicate the on-axis and off-axis low energy ratio (1580a) and high energy ratio (1580b), as well as the on-axis and off-axis monochromaticity (1680), respectively, of the x-ray radiation emitted using exemplary carrier 1640. As shown, the x-ray radiation exhibits essentially the same characteristics on-axis and 5 degrees off-axis. Accordingly, while exemplary carrier 1740 improves both on-axis and off-axis monochromaticity, use of the exemplary carrier illustrate in FIGS. 17A-C exhibits a substantial increase in the off-axis monochromaticity, providing substantial benefits to x-ray imaging using monochromatic x-rays, for example, by improving uniformity, reducing dose and enabling the use of higher x-ray tube voltages to increase the monochromatic intensity to improve the spatial resolution and ability differentiate small density variations (e.g., small tissue anomalies such as micro-calcifications in breast material), as discussed in further detail below. Using carrier 1740, monochromatic x-ray radiation is emitted having a monochromaticity of at least 0.9 across a 15 degree field of view and a monochromaticity of at least 0.95 across a 10 degree field of view about the longitudinal axis.

It should be appreciated that the exemplary carrier described herein may be configured to be a removable housing or may be integrated into the x-ray device. For example, one or more aspects of the exemplary carriers described herein may integrated, built-in or otherwise made part an x-ray device, for example, as fixed components, as the aspects are not limited in this respect.

Figure 20:
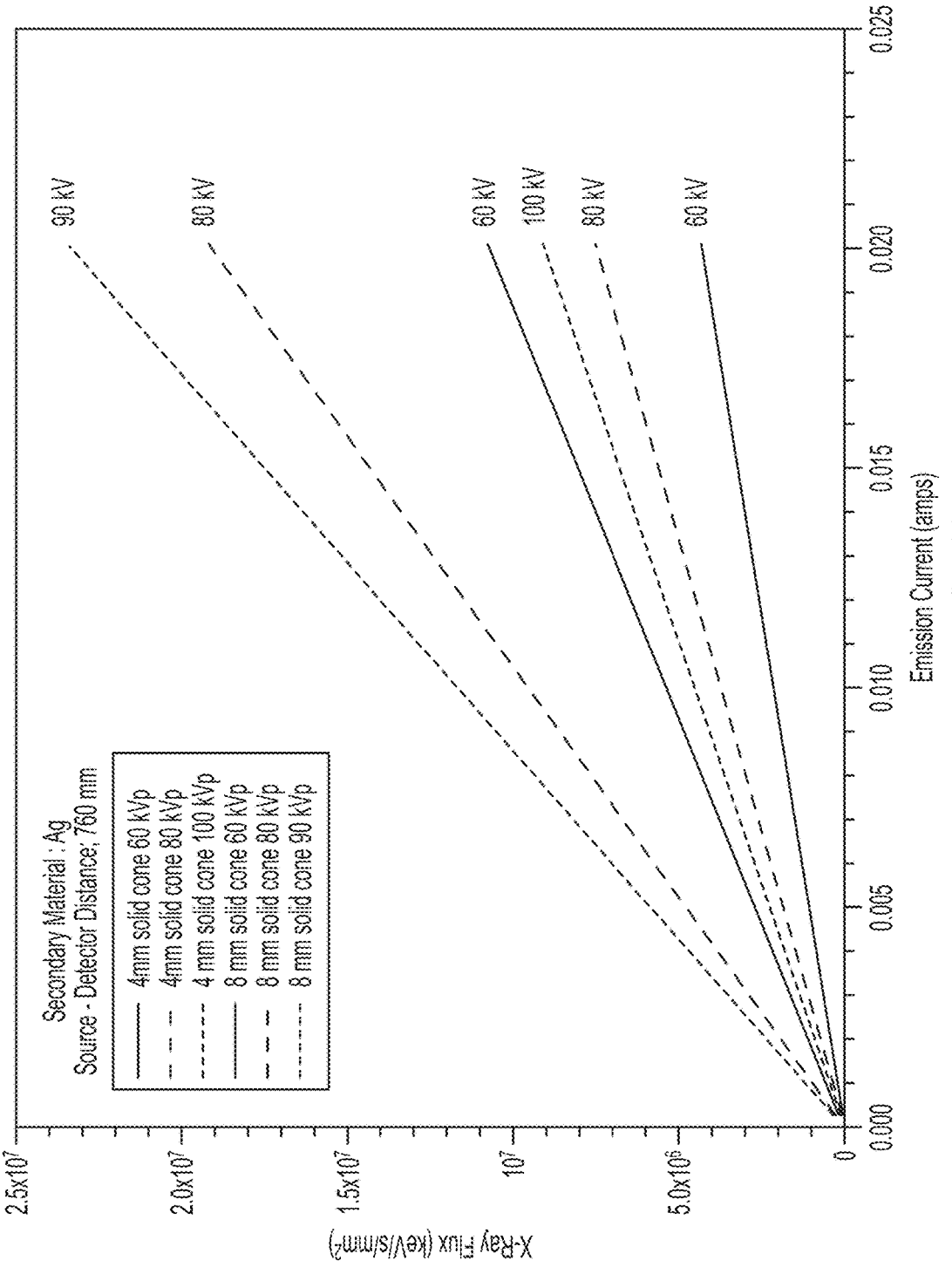
FIG. 20 illustrates x-ray intensity as a function of emission current for a number of primary voltages for secondary targets of two different geometries.

As is well known, the intensity of monochromatic x-ray emission may be increased by increasing the cathode-anode voltage (e.g., the voltage potential between filament 1106 and primary target 1100 illustrated in FIGS. 11A and 11B) and/or by increasing the filament current which, in turn, increases the emission current of electrons emitted by the filament, the latter technique of which provides limited control as it is highly dependent on the properties of the cathode. The relationship between x-ray radiation intensity, cathode-anode voltage and emission current is shown in FIG. 20, which plots x-ray intensity, produced using a silver (Ag) secondary target and a source-detector distance of 750 mm, against emission current at a number of different cathode-anode voltages using two different secondary target geometries (i.e., an Ag cone having a 4 mm diameter base and an Ag cone having a 8 mm diameter base).

Figure 21:
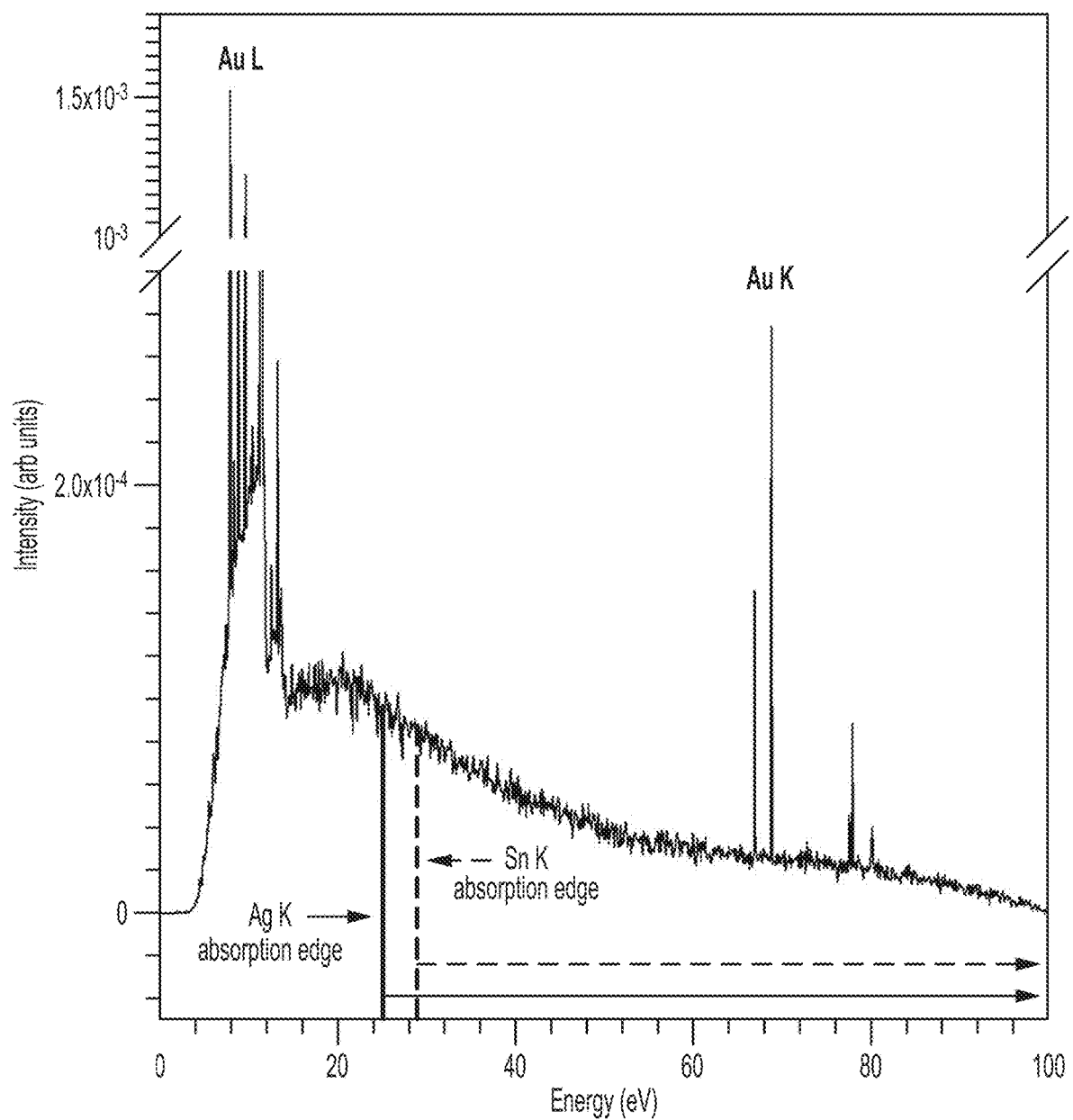
FIG. 21 illustrates the x-ray spectrum emitted from a gold primary target.

Conventionally, the cathode-anode voltage was selected to be approximately twice that of the energy of the characteristic emission line of the desired monochromatic x-ray radiation to be fluoresced by the secondary target as a balance between producing sufficient high energy broadband x-ray radiation above the absorption edge capable of inducing x-ray fluorescence in the secondary target to produce adequate monochromatic x-ray intensity, and producing excess high energy broadband x-ray radiation that contaminates the desired monochromatic x-ray radiation. For example, for an Ag secondary target, a cathode-anode potential of 45 kV (e.g., the electron optics would be set at −45 kV) would conventionally be selected to ensure sufficient high energy broadband x-rays are produced above the K-edge of silver (25 keV) as illustrated in FIG. 21 to produce the 22 keV Ag K monochromatic x-ray radiation shown in FIG. 19 (bottom left). Similarly, for a Sn secondary target, a cathode-anode potential of 50 kV would conventionally be selected to ensure sufficient high energy broadband x-rays are produced above the K-edge of tin (29 keV) as illustrated in FIG. 21 to produce the 25 keV Sn K monochromatic x-ray radiation shown in FIG. 19 (bottom right). This factor of two limit on the cathode-anode voltage was conventionally followed to limit the high energy contamination of the monochromatic x-rays emitted from the x-ray apparatus.

Figure 22:
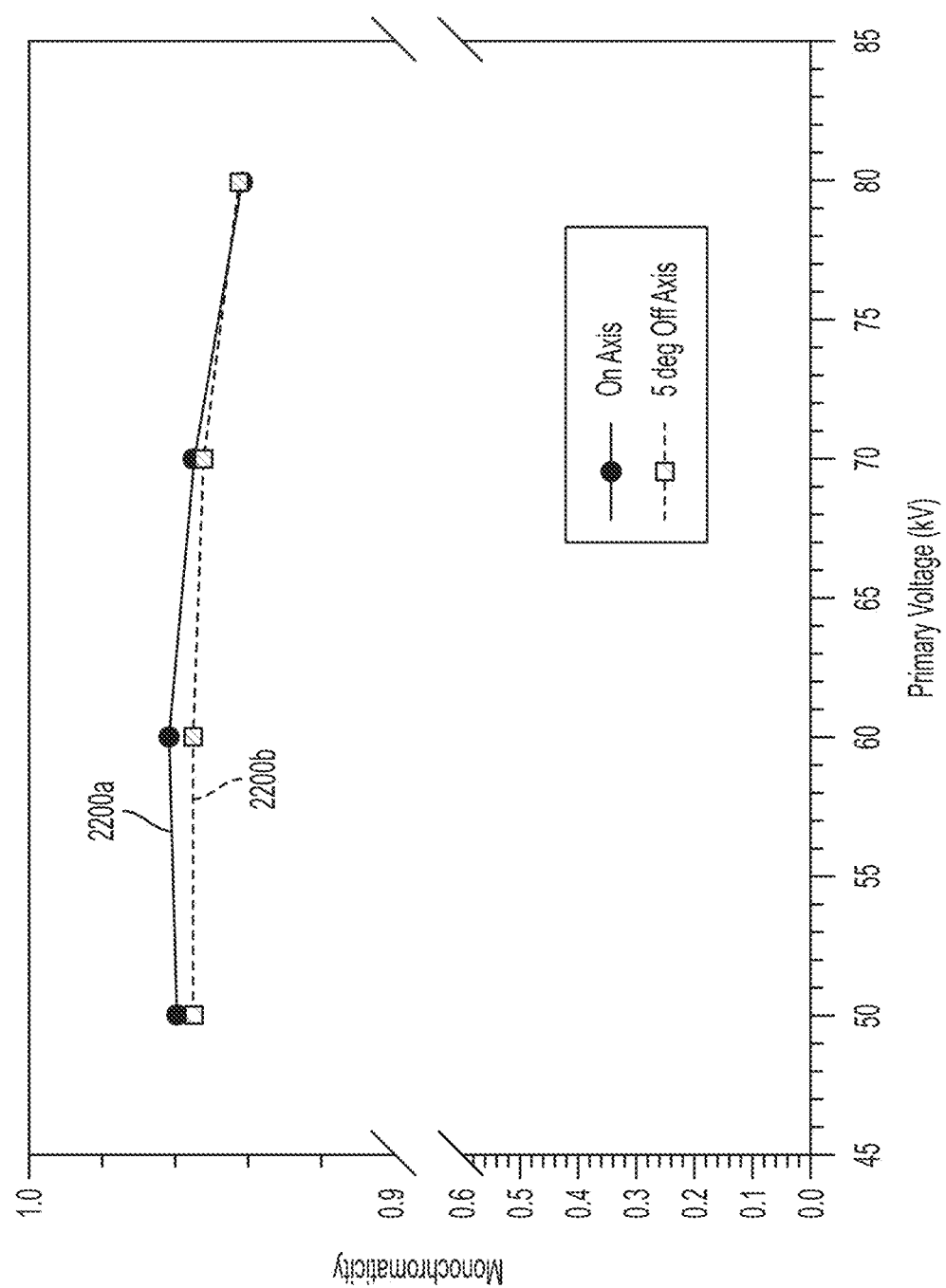
FIG. 22 illustrates on-axis and off-axis monochromaticity as a function of primary voltage for a tin secondary target using the carrier illustrated in FIGS. 17A, 17B and 17C.
Figure 23:
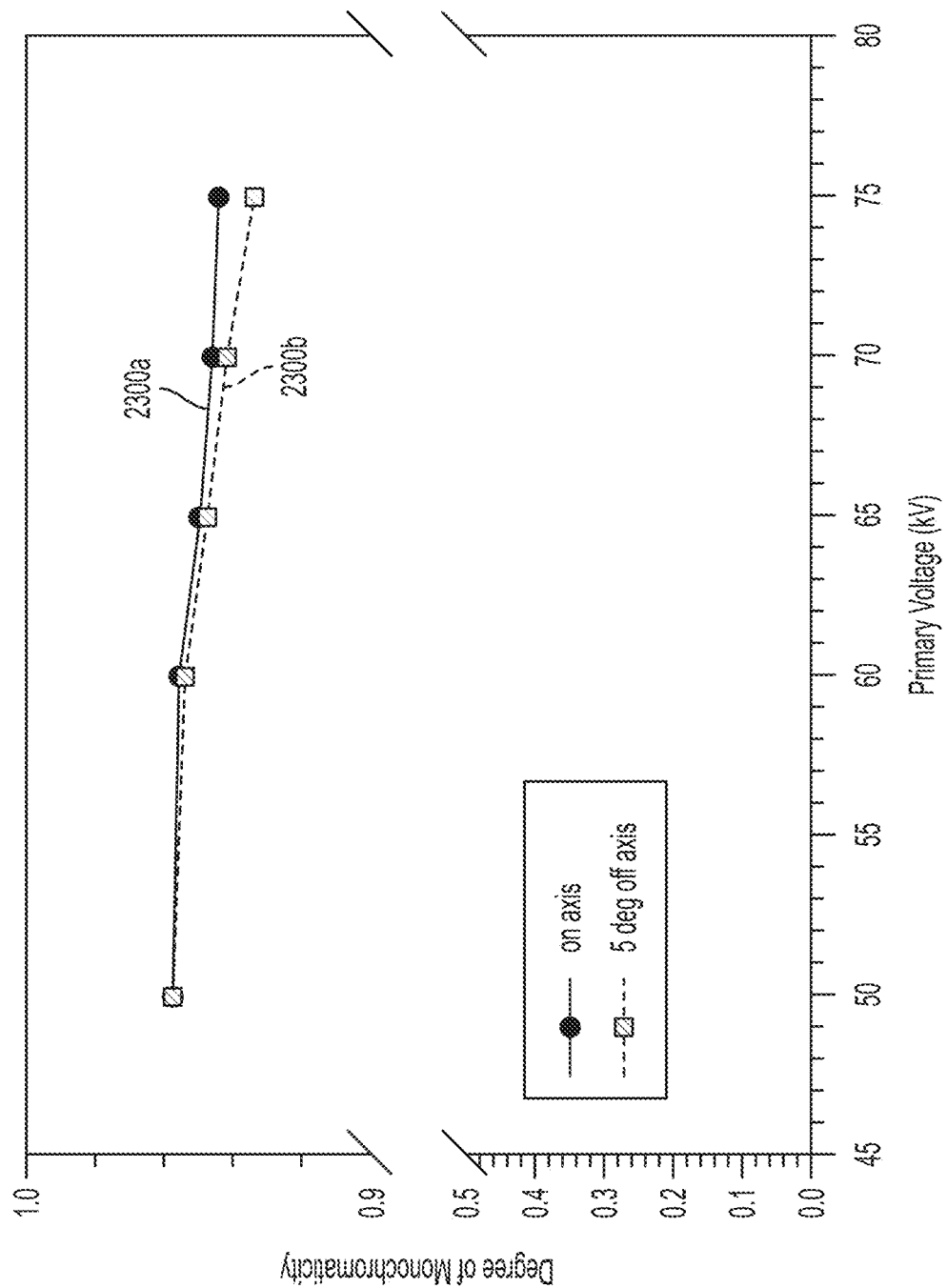
FIG. 23 illustrates on-axis and off-axis monochromaticity as a function of primary voltage for a silver secondary target using the carrier illustrated in FIGS. 17A, 17B and 17C.

The inventor has recognized that the techniques described herein permit the factor of two limit to be eliminated, allowing high cathode-anode voltages to be used to increase monochromatic x-ray intensity without significantly increasing broadband x-ray radiation contamination (i.e., without substantial decreases in monochromaticity). In particular, techniques for blocking broadband x-ray radiation, including the exemplary secondary target carriers developed by the inventors can be used to produce high intensity monochromatic radiation while maintaining excellent monochromaticity. For example, FIG. 22 illustrates the on-axis monochromaticity 2200a and the off-axis monochromaticity 2200b for a number of cathode-anode voltages (primary voltage) with a Sn secondary target using exemplary carrier 1740 developed by the inventor. Similarly, FIG. 23 illustrates the on-axis monochromaticity 2300a and the off-axis monochromaticity 2300b for a number of cathode-anode voltages (primary voltage) with an Ag secondary target using exemplary carrier 1740 developed by the inventor. As shown, a high degree of monochromaticity is maintained across the illustrated range of high voltages, varying by only 1.5% over the range illustrated. Thus, higher voltages can be used to increase the monochromatic x-ray intensity (e.g., along the lines shown in FIG. 20) without substantially impacting monochromaticity. For example, monochromatic x-ray radiation of over 90% purity (M>0.9) can be generated using a primary voltage up to and exceeding 100 KeV, significantly increasing the monochromatic x-ray intensity.

According to some embodiments, a primary voltage (e.g., a cathode-anode voltage potential, such as the voltage potential between filament 1106 and primary target 1110 of x-ray tube 1150 illustrated in FIGS. 11A and 11B) greater than two times the energy of the desired monochromatic x-ray radiation fluoresced from a given target is used to generate monochromatic x-ray radiation. According to some embodiments, a primary voltage greater than or equal to approximately two times and less than or equal to approximately three times the energy of the desired monochromatic x-ray radiation fluoresced from a given target is used to generate monochromatic x-ray radiation. According to some embodiments, a primary voltage greater than or equal to approximately three times and less than or equal to approximately four times the energy of the desired monochromatic x-ray radiation fluoresced from a given target is used to generate monochromatic x-ray radiation. According to some embodiments, a primary voltage greater than or equal to approximately four times and less than or equal to approximately five times the energy of the desired monochromatic x-ray radiation fluoresced from a given target is used to generate monochromatic x-ray radiation. According to some embodiments, a primary voltage greater than or equal to five times greater the energy of the desired monochromatic x-ray radiation fluoresced from a given target is used to generate monochromatic x-ray radiation. In each case, x-ray radiation having monochromaticity of greater than or equal to 0.9, on and off axis across the field of view may be achieved, though it should be appreciated that achieving those levels of monochromaticity is not a requirement.

The inventor has recognized the geometry of the x-ray tube may contribute to broadband x-ray radiation contamination. The inventor has appreciated that the electron optics of an x-ray tube may be improved to further reduce the amount of broadband x-ray radiation that is generated that could potentially contaminate the monochromatic x-rays emitted from an x-ray device. Referring again to FIGS. 11A and 11B, x-ray device 1100 includes electron optics 1105 configured to generate electrons that impinge on primary target 1110 to produce broadband x-ray radiation. The inventor has developed electron optics geometry configured to reduce and/or eliminate bombardment of surfaces other than the primary target within the vacuum enclosure. This geometry also reduces and/or eliminates parasitic heating of other surfaces that would have to be removed via additional cooling in conventional systems.

As an example, the geometry of electron optics 1105 is configured to reduce and/or eliminate bombardment of window portion 1130 and/or other surfaces within vacuum tube 1150 to prevent unwanted broadband x-ray radiation from being generated and potentially emitted from the x-ray tube to degrade the monochromaticity of the emitted x-ray radiation spectrum. In the embodiment illustrated in FIGS. 11A and 11B, electron optics 1105 comprises a filament 1106, which may be generally toroidal in shape, and guides 1107, 1108 and/or 1109 positioned on the inside and outside of the toroidal filament 1106. For example, guides 1107, 1108, 1109 may be positioned concentrically with the toroidal filament 1106 (e.g., an inner guide 1107 positioned within the filament torus and an outer guides 1108 and 1109 positioned around the filament torus) to provide walls on either side of filament 1106 to prevent at least some electrons from impinging on surfaces other than primary target 1110, as discussed in further detail below.

According to some embodiments, electronic optics 105 is configured to operate at a high negative voltage (e.g., 40 kV, 50 kV, 60 kV, 70 kV, 80 kV, 90 kV or more). That is, filament 1106, inner guide 1107 and outer guides 1108, 1109 may all be provided at a high negative potential during operation of the device. As such, in these embodiments, primary target 1110 may be provided at a ground potential so that electrons emitted from filament 1106 are accelerated toward primary target 1110. However, the other components and surfaces of x-ray tube within the vacuum enclosure are typically also at ground potential. As a result, electrons will also accelerate toward and strike other surfaces of x-ray tube 1150, for example, the transmissive interface between the inside and outside of the vacuum enclosure (e.g., window 1130 in FIGS. 11a and 11b). Using conventional electron optics, this bombardment of unintended surfaces produces broadband x-ray radiation that contributes to the unwanted broadband spectrum emitted from the x-ray device and causes undesirable heating of the x-ray tube. The inventor appreciated that this undesirable bombardment of surfaces other than primary target 1110 may be reduced and/or eliminated using inner guide 1107 and outer guides 1108 and/or 1109 that provide a more restricted path for electrons emitted by filament 1106.

According to some embodiments, guides 1107-1109 are cylindrical in shape and are arranged concentrically to provide a restricted path for electrons emitted by filament 1106 that guides the electrons towards primary target 1110 to prevent at least some unwanted bombardment of other surfaces within the vacuum enclosure (e.g., reducing and/or eliminating electron bombardment of window portion 1130). However, it should be appreciated that the guides used in any given implementation may be of any suitable shape, as the aspects are not limited in this respect. According to some embodiments, guides 1107, 1108 and/or 1109 comprise copper, however, any suitable material that is electrically conducting (and preferably non-magnetic) may be used such as stainless steel, titanium, etc. It should be appreciated that any number of guides may be used. For example, an inner guide may be used in conjunction with a single outer guide (e.g., either guide 1108 or 1109) to provide a pair guides, one on the inner side of the cathode and one on the outer side of the cathode. As another example, a single inner guide may be provided to prevent at least some unwanted electrons from bombarding the interface between the inside and outside of the vacuum tube (e.g., window portion 1130 in FIGS. 11A and 11B), or a single outer guide may be provide to prevent at least some unwanted electrons from bombarding other internal surface of the vacuum tube provides. Additionally, more than three guides may be used to restrict the path of electrons to the primary target to reduce and/or eliminate unwanted bombardment of surfaces within the vacuum enclosure, as the aspects are not limited in this respect.

Figure 24A:
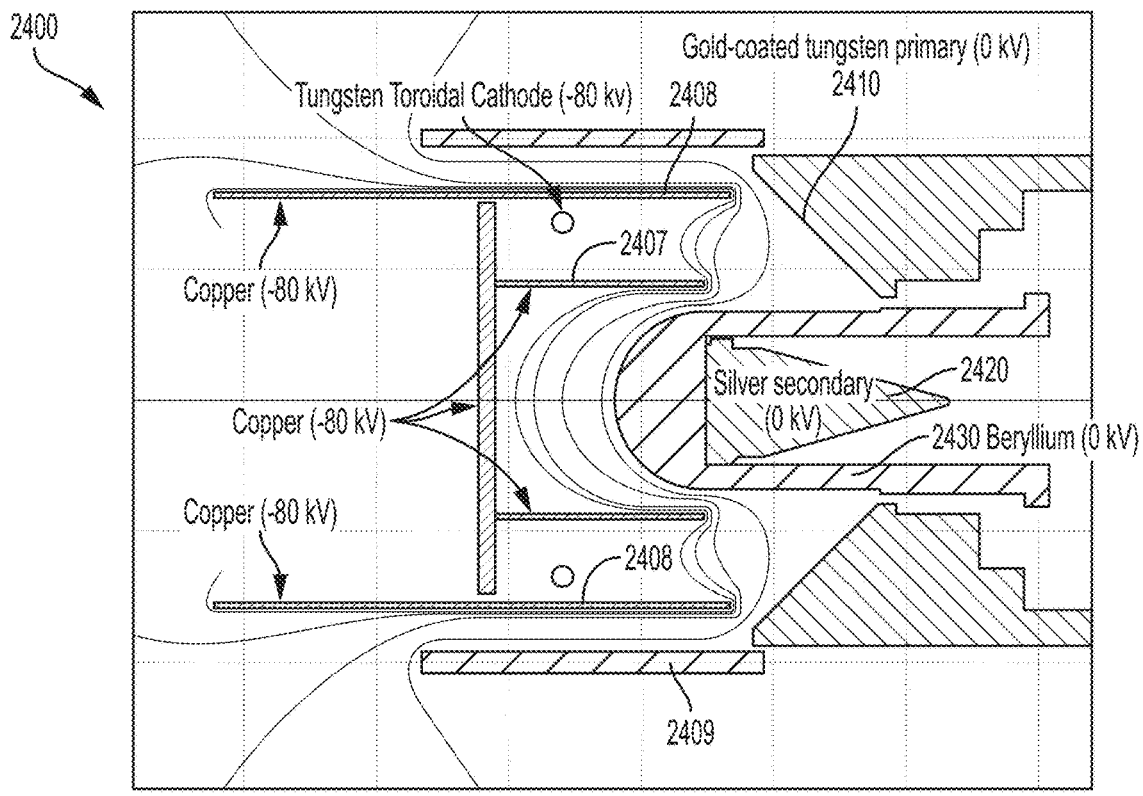
FIGS. 24A and 24B illustrate a cross-section of a monochromatic x-ray source 2400 with improved electron optics, in accordance with some embodiments.
Figure 24B:
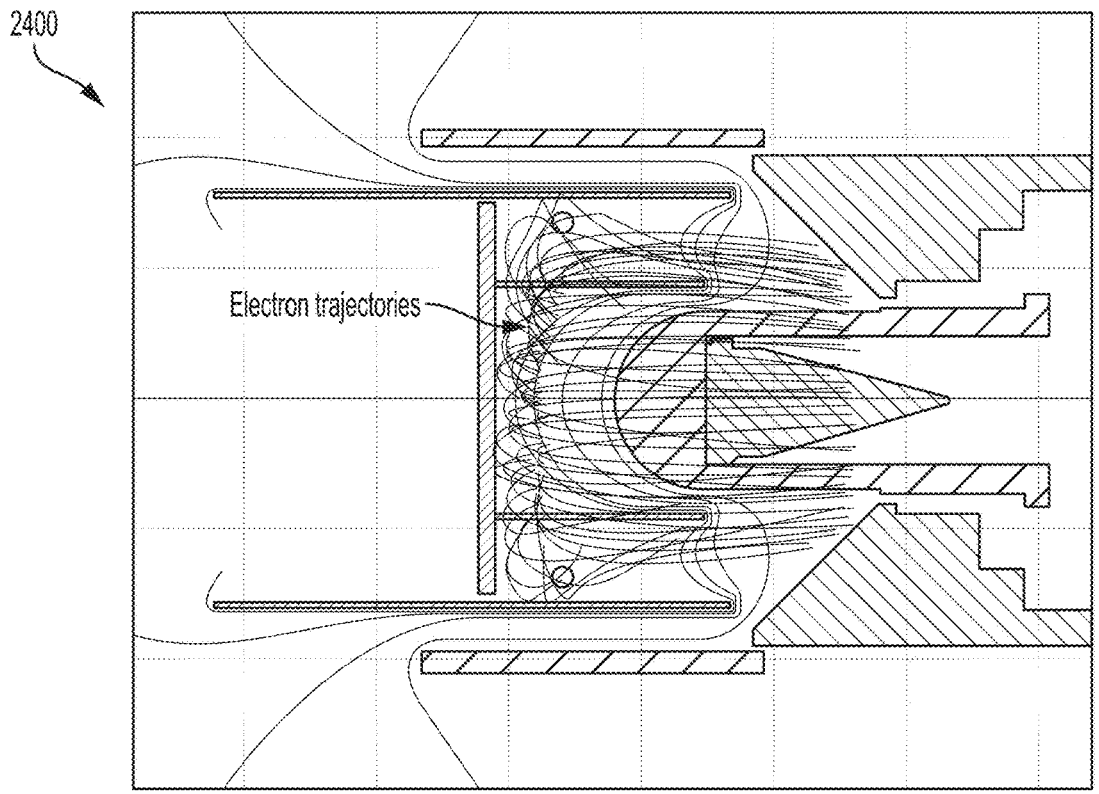
Figure 25:
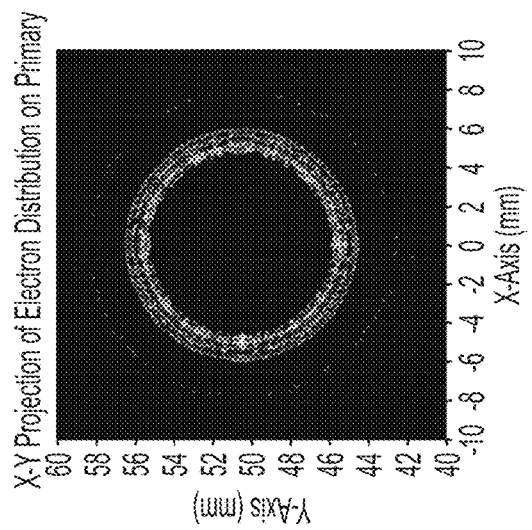
FIG. 25 illustrate the locus of points where the electrons strike the primary target in the monochromatic x-ray source illustrated in FIGS. 24A and 24B.
Figure 26:
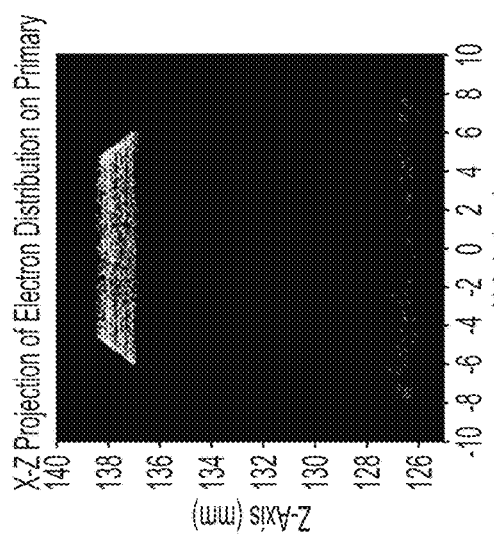
FIG. 26 illustrate the locus of points where the electrons strike the primary target in the monochromatic x-ray source illustrated in FIGS. 24A and 24B.
Figure 27:
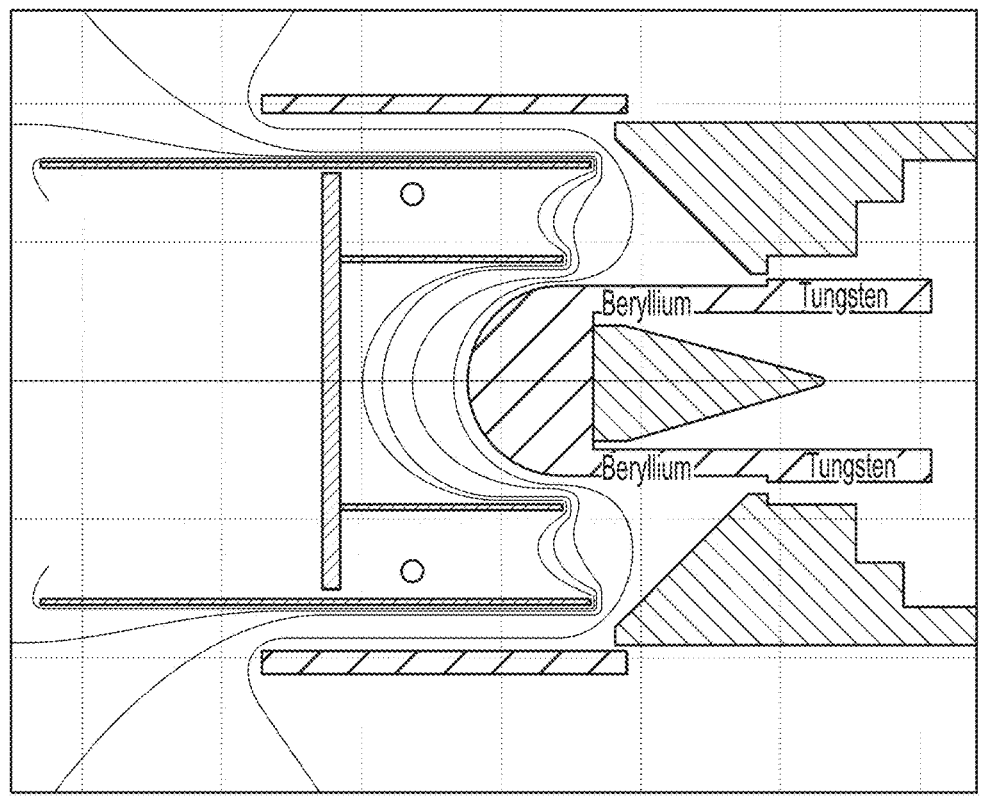
FIG. 27 illustrates a monochromatic x-ray source including a hybrid interface component.
Figure 28:
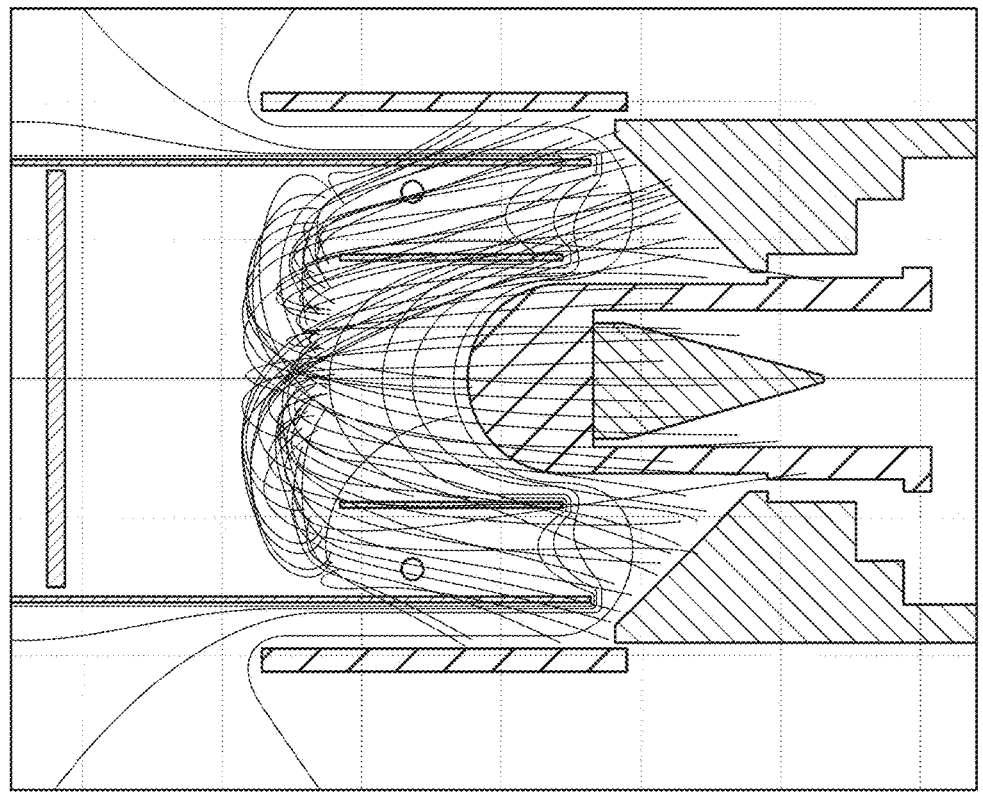
FIG. 28 illustrates an alternative configuration in which the cathode is moved further away from the primary target, resulting in divergent electron trajectories and reduced monochromaticity.

FIGS. 24A and 24B illustrate a cross-section of a monochromatic x-ray source 2400 with improved electron optics, in accordance with some embodiments. In the embodiment illustrated, there is a 80 kV is the potential between the cathode and the anode. Specifically, a tungsten toroidal cathode 2406 is bias at −80 kV and a gold-coated tungsten primary target 2410 is at a ground potential. A copper inner guide 2407 and an outer copper guides 2408 and 2409 are also provided at −80 kV to guide electrons emitted from the cathode to prevent at least some electrons from striking surfaces other than primary target 2410 to reduce the amount of spurious broadband x-ray radiation. Monochromatic x-ray source 2400 uses a silver secondary target 2420 and a beryllium interface component 2430. FIG. 24B illustrates the electron trajectories between the toroidal cathode and the primary target when the monochromatic x-ray source 2400 is operated. FIGS. 25 and 26 illustrate the locus of points where the electrons strike primary target 2410, demonstrating that the guides prevent electrons from striking the interface component 2430 in this configuration. FIG. 27 illustrates a monochromatic x-ray source including a hybrid interface component having transmissive portion of beryllium and a blocking portion of tungsten that produces monochromatic x-ray radiation of 97% purity (M=0.97) when combined with other techniques described herein (e.g., using the exemplary carriers described herein). FIG. 28 illustrates an alternative configuration in which the cathode is moved further away from the primary target, resulting in divergent electron trajectories and reduced monochromaticity.

The monochromatic x-ray sources described herein are capable of providing relatively high intensity monochromatic x-ray radiation having a high degree of monochromaticity, allowing for relatively short exposure times that reduce the radiation dose delivered to a patient undergoing imaging while obtaining images with high signal-to-noise ratio. Provided below are results obtained using techniques described herein in the context of mammography. These results are provided to illustrate the significant improvements that are obtainable using one or more techniques described herein, however, the results are provided as examples as the aspects are not limited for use in mammography, nor are the results obtained requirements on any of the embodiments described herein.

Figure 29:
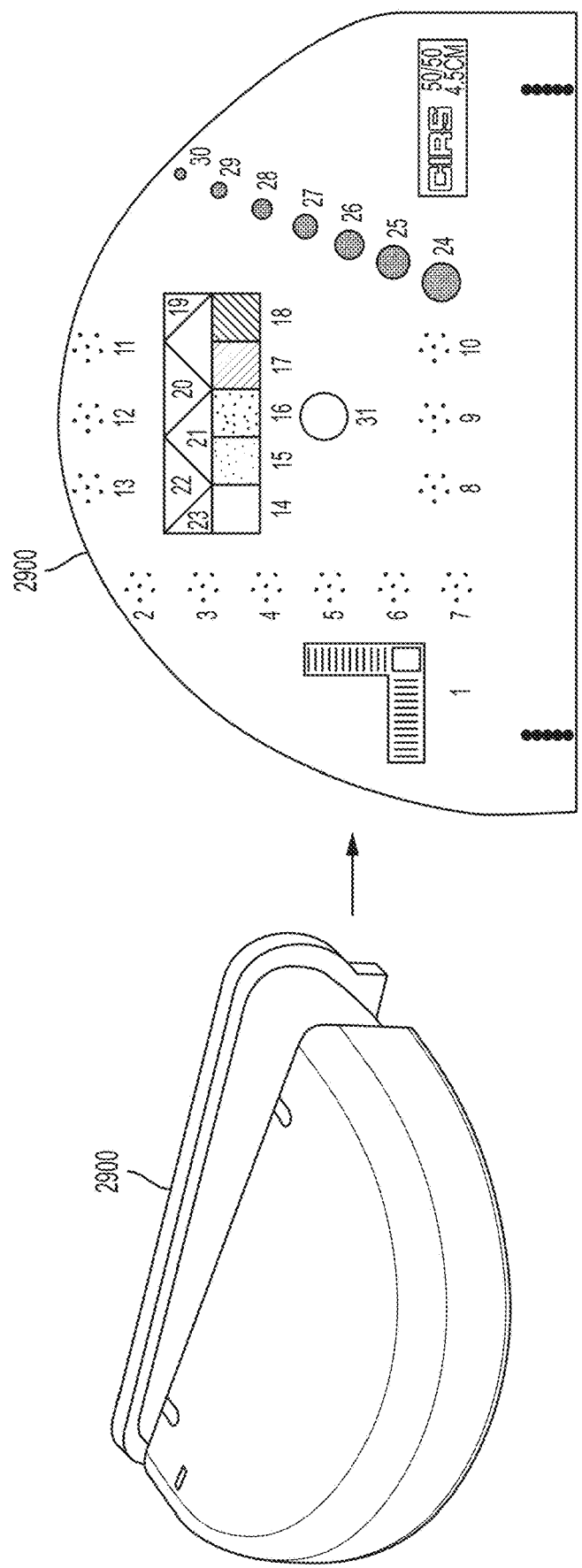
FIG. 29 illustrates a mammographic phantom used to perform imaging experiment using monochromatic x-ray sources described herein.
Figure 30:
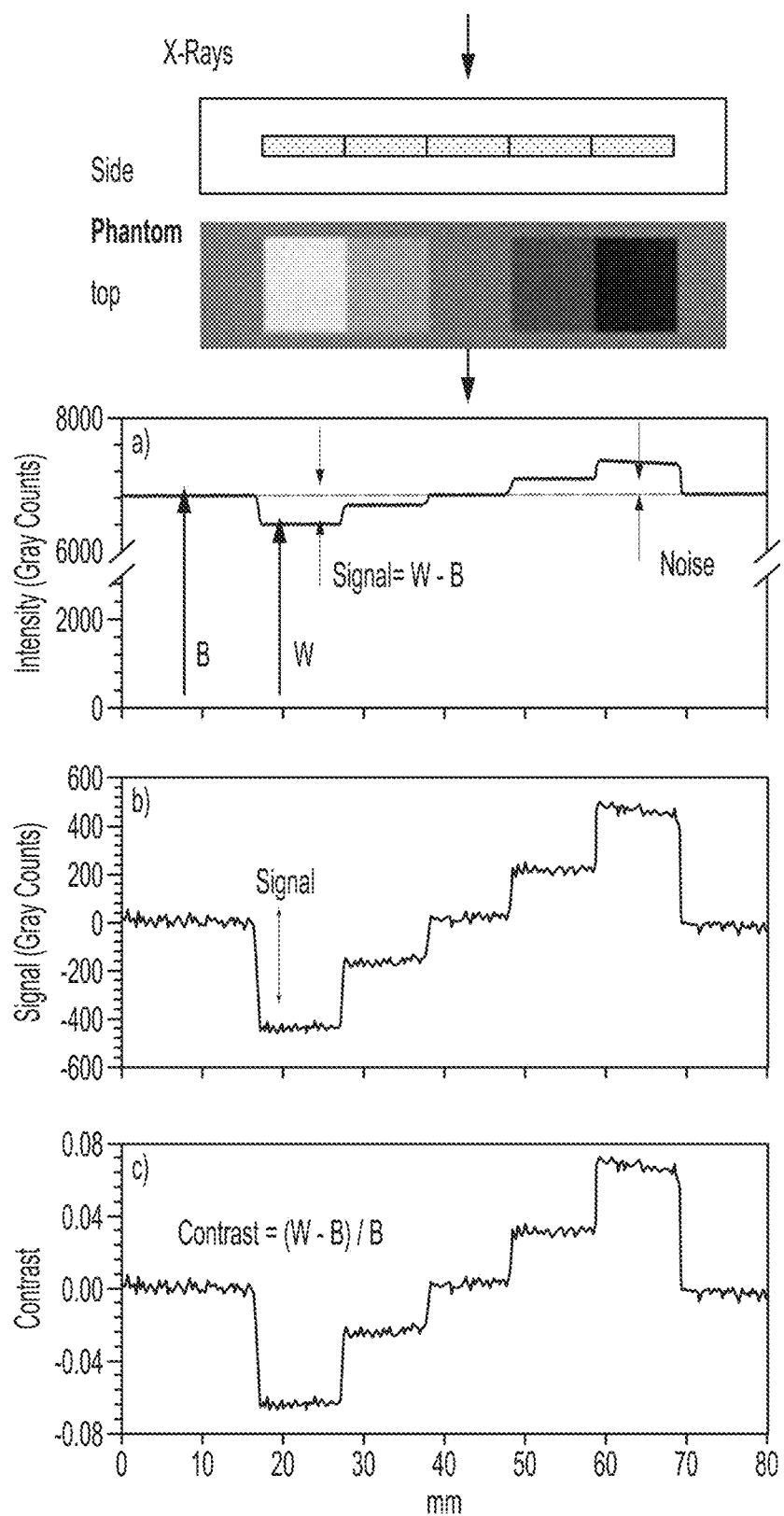
FIG. 30 illustrates histograms of the embedded linear array of blocks of the phantom illustrated in FIG. 29.

FIG. 29 illustrates a mammographic phantom (CIRS Model 011a) 2900 used to test aspects of the performance of the monochromatic x-ray device developed by the inventor incorporating techniques described herein. Phantom 2900 includes a number of individual features of varying size and having different absorption properties, as illustrated by the internal view of phantom 2900 illustrated in FIG. 29. FIG. 30 highlights some of the embedded features of phantom 2900, including the linear array of 5 blocks, each 1 cm thick and each having a composition simulating different densities of breast tissue. The left most block simulates 100% glandular breast tissue, the right most, 100% adipose (fat) tissue and the other three have a mix of glandular and adipose with ratios ranging from 70:30 (glandular:adipose) to 50:50 to 30:70. All 5 blocks are embedded in the phantom made from a 50:50 glandular to adipose mix. The total thickness of the phantom is 4.5 cm.

FIG. 30 also shows a schematic description of the imaging process in one dimension as the x-ray beam enters the phantom, passes through the blocks and the phantom on their way to the imaging detector where the transmitted x-ray intensity, is converted into an integrated value of Gray counts. (The intensity in this case is the sum of the x-ray energies reaching each detector pixel. The electronics in each pixel convert this energy sum into a number between 0 and 7000, where 7000 represents the maximum energy sum allowable before the electronics saturate. The number resulting from this digital conversion is termed a Gray count).

The data shown by the red horizontal line in a) of FIG. 30 is the x-ray intensity, B, measured through the background 50:50 glandular-adipose mixture. The data shown by the black curve is the x-ray intensity, W, transmitted through the 50:50 mix and the 1 cm blocks. The varying step sizes represent different amounts of x-ray absorption in the blocks due to their different compositions. Plot b) in FIG. 30 defines the signal, S, as W-B and plot c) of FIG. 30 defines the contrast as S/B. The figure of merit that is best used to determine the detectability of an imaging system is the Signal-to-Noise Ratio, SNR. For the discussion here, the SNR is defined as S/noise, where the noise is the standard deviation of the fluctuations in the background intensity shown in plot a) of FIG. 30. Images produced using techniques described herein and may with 22 keV x-rays and 25 keV x-rays and presented herein and compared to the SNR values with those from a commercial broad band x-ray mammography machine.

Radiation exposure in mammographic examinations is highly regulated by the Mammography Quality Standards Act (MQSA) enacted in 1994 by the U.S. Congress. The MQSA sets a limit of 3 milliGray (mGy) for the mean glandular dose (mgd) in a screening mammogram; a Gray is a joule/kilogram. This 3 mGy limit has important ramifications for the operation of commercial mammography machines, as discussed in further detail below. Breast tissue is composed of glandular and adipose (fatty) tissue. The density of glandular tissue ($\rho$=1.03 gm/cm$^{-3}$) is not very different from the density of adipose tissue ($\rho$=0.93 gm/cm$^{-3}$) which means that choosing the best monochromatic x-ray energy to optimize the SNR does not depend significantly on the type of breast tissue. Instead, the choice of monochromatic energy for optimal imaging depends primarily on breast thickness. A thin breast will attenuate fewer x-rays than a thick breast, thereby allowing a more significant fraction of the x-rays to reach the detector. This leads to a higher quality image and a higher SNR value. These considerations provide the major rationale for requiring breast compression during mammography examinations with a conventional, commercial mammography machine.

Figure 32:
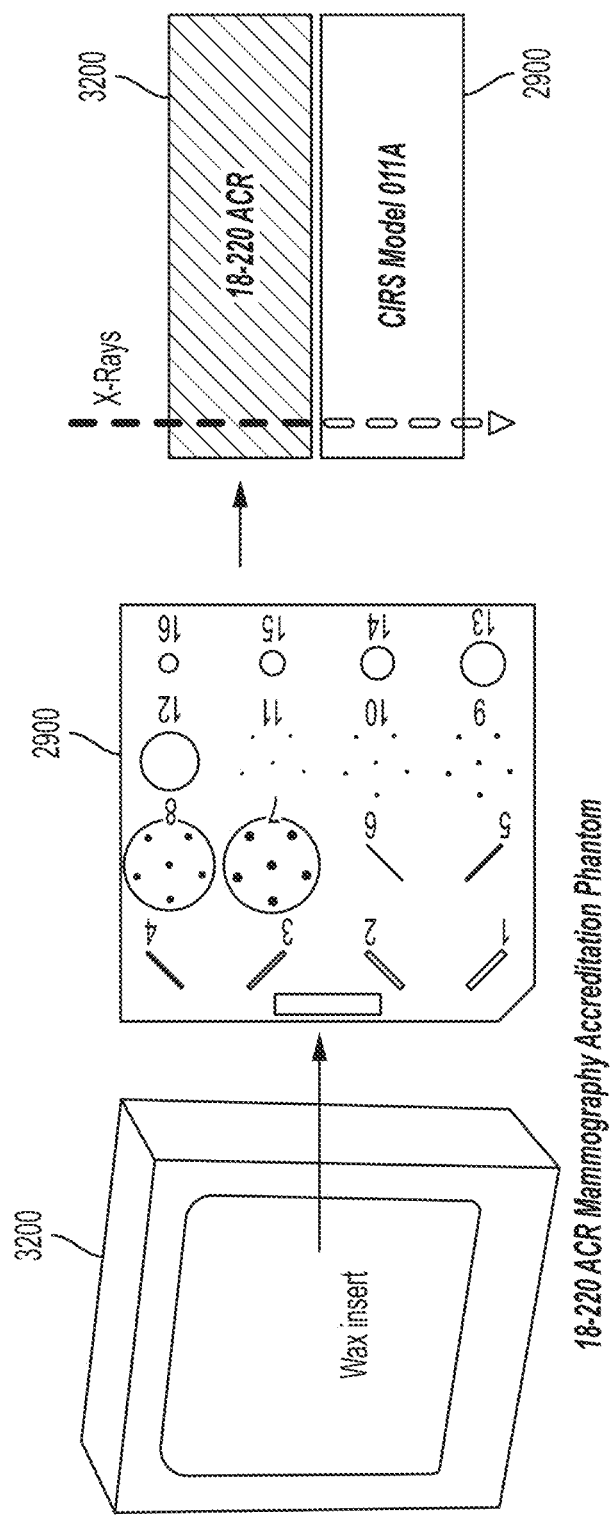
FIG. 32 illustrates stacked mammographic phantoms to model thick breast tissue.

Imaging experiments were conducted the industry-standard phantom illustrated in FIG. 29, which has a thickness of 4.5 cm and is representative of a typical breast under compression. Phantom 2900 has a uniform distribution of glandular-to-adipose tissue mixture of 50:50. The SNR and mean glandular dose are discussed in detail below for CIRS phantom images obtained with monochromatic energies of 22 keV and 25 keV. Experiments were also conducted with a double phantom, as illustrated in FIG. 32, to simulate a thick breast under compression with a thickness of 9 cm. The double phantom also has a uniform distribution of glandular-to-adipose tissue mixture of 50:50. The SNR and mean glandular dose are presented for the double phantom using a monochromatic energy of 25 keV. The high SNR obtained on this model of a thick breast demonstrates that monochromatic x-rays can be used to examine women with reduced compression or no compression at all, since, typically, a compressed breast of 4.5 cm thickness is equivalent to an uncompressed breast of 8-9 cm thickness, as discussed in further detail below.

The experiments demonstrate that the mean glandular dose for the monochromatic measurements is always lower than that of the commercial machine for the same SNR. Stated in another way, the SNR for the monochromatic measurements is significantly higher than that of the commercial machines for the same mean glandular dose. Thus, monochromatic X-ray mammography provides a major advance over conventional broadband X-ray mammographic methods and has significant implications for diagnosing breast lesions in all women, and especially in those with thick or dense breast tissue. Dense breasts are characterized by non-uniform distributions of glandular tissue; this non-uniformity or variability introduces artifacts in the image and makes it more difficult to discern lesions. The increased SNR that monochromatic imaging provides makes it easier to see lesions in the presence of the inherent tissue variability in dense breasts, as discussed in further detail below.

Figure 31:
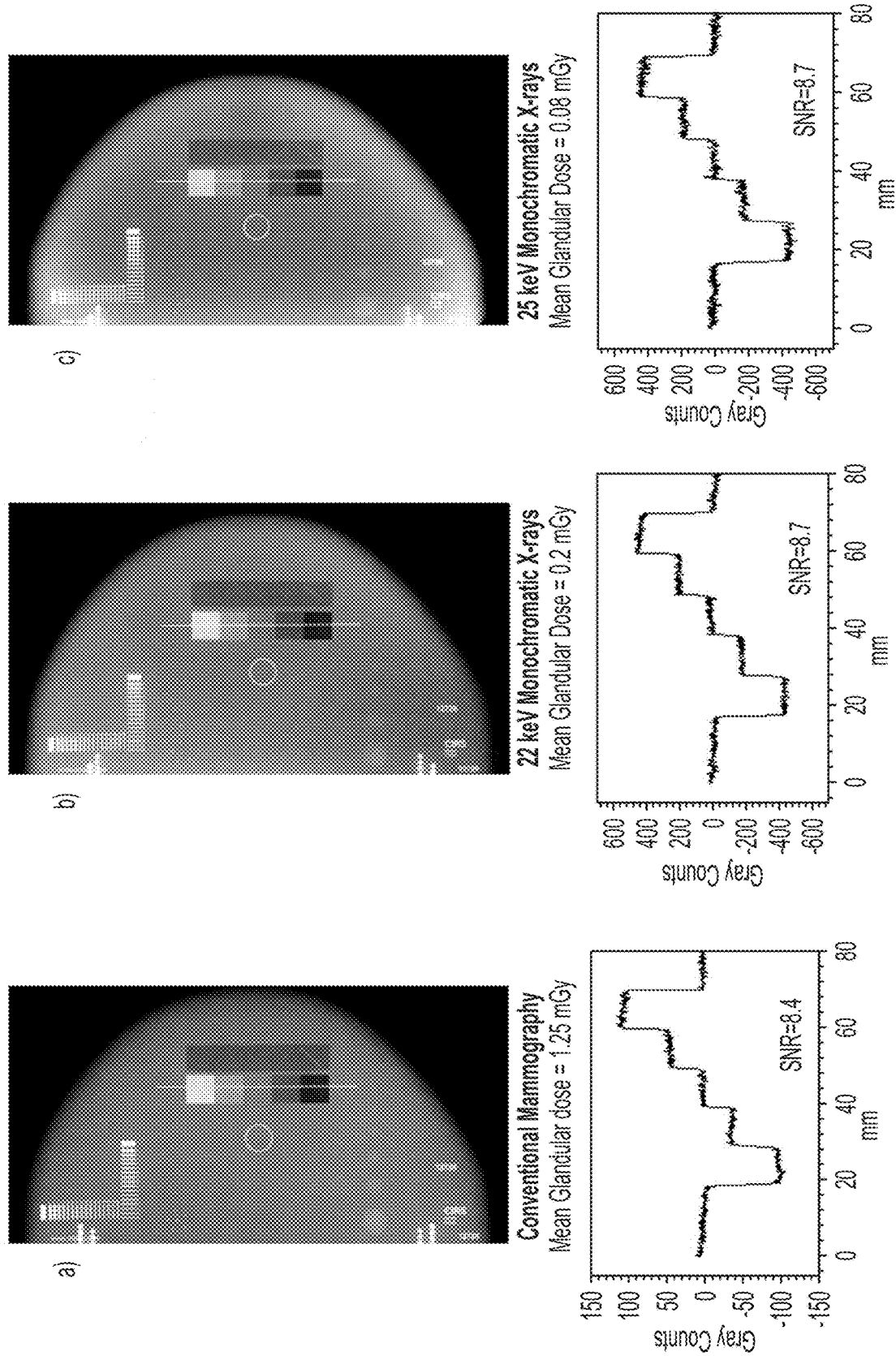
FIG. 31 illustrates images of the phantom in FIG. 29 using a commercial broadband x-ray system and a monochromatic x-ray system according to some embodiments, along with corresponding histograms.

FIG. 31 illustrates images of phantom 2900 obtained from a monochromatic x-ray source described herein using monochromatic Ag K (22 keV) and Sn K (25 keV) x-rays and an image from a conventional commercial mammography machine that uses broad band emission, along with respective histograms through the soft tissue blocks. The image from the commercial machine is shown in (a) of FIG. 31. The SNR for the 100% glandular block is 8.4 and the mean glandular dose (mgd) is 1.25 mGy (1 Gy=1 joule/kgm). Image (b) in FIG. 31 illustrates a monochromatic image using 22 keV x-rays and image (c) in FIG. 31 was obtained with 25 keV X-rays. The mean glandular doses for the 100% glandular block measured with 22 keV is 0.2 mGy and that measured with 25 keV is 0.08 mGy, and the SNR values are 8.7 for both energies. To achieve the same SNR as the commercial machine, the monochromatic system using 22 keV delivers a dose that is 6.7 times lower and using 25 keV delivers a dose that is 15 times lower.

The dose reduction provided by the monochromatic X-ray technology offers significantly better diagnostic detectability than the conventional broad band system because the SNR can be increased by factors of 3 to 6 times while remaining well below the regulatory dose limit of 3 mGy for screening. For example, the SNR value for the 22 keV images would be 21.8 at the same dose delivered by the commercial machine (1.25 mGy) and 32 for a dose of 2.75 mGy. Similarly, using the 25 keV energy, the SNR values would be 34 and 51 for mean glandular doses of 1.25 mGy and 2.75 mGy, respectively. This significantly enhanced range in SNR has enormous advantages for diagnosing women with dense breast tissue. As mentioned earlier, such tissue is very non-uniform and, unlike the uniform properties of the phantoms and women with normal density tissue, the variability in glandular distribution in dense breast introduces artifacts and image noise, thereby making it more difficult to discern lesions. The higher SNR provided by techniques describe herein can overcome these problems.

The monochromatic x-ray device incorporating the techniques described herein used to produce the images displayed here is comparable in size and footprint of a commercial broadband x-ray mammography system, producing for the first time low dose, high SNR, uniform images of a mammographic phantom using monochromatic x-rays with a degree of monochromaticity of 95%. In fact, conventional monochromatic x-ray apparatus do not even approach these levels of monochromaticity.

To simulate thick breast mammography, a model for thick breast tissue was created by placing two phantoms on top of each other (total thickness 9.0 cm), the 18-220 ACR Mammography Accreditation Phantom (3200) placed on top of the CIRS Model 011A phantom (2900), as shown in FIG. 32. For this series of experiments, 25 keV x-rays were selected to optimize the transmission while maintaining good contrast in the soft tissue represented by the 1 cm array of blocks embedded on the CIRS phantom. The images for the 25 keV monochromatic x-rays are compared to the images obtained from the same commercial broad band mammography machine used in the previous experiment. The resulting images are displayed in FIG. 33, along with the histograms of the contrast through the soft tissue blocks.

The image quality for the thick breast tissue is superior to anything obtainable with current commercial broad band systems. The dose delivered by the commercial machine is 2.75 mGy and only achieves a SNR of 3.8 in the 100% glandular block. The monochromatic image in FIG. 33 has a SNR=7.5 for a dose of 0.43 mGy. The dose required for the commercial broad band X-ray system to reach a SNR of 8.5, the accepted value of radiologists for successful detection in thinner 4.5 cm thick tissue would be 14 mGy, 11 times higher than the commercial dose used to image normal density breast tissue (1.25 mGy). This is prohibitively high and unsafe for screening and 4.7 times higher than the regulated MQSA screening limit. On the other hand, the required dose from the monochromatic system to achieve a SNR=8.5 is only 0.54 mGy, 26 times lower than that required by the commercial machine. The dose required using monochromatic x-rays is safe, more than 5 times lower than the regulatory limit, and still 2.5 times lower than the dose for normal thickness, 4.5 cm breasts using the commercial broad band x-ray mammography machine. Comparing the monochromatic X-ray and the commercial broad band X-ray machines at close to the maximum allowed exposure (2.75 mGy), the monochromatic technology provides 5 times higher SNR. The above discussion is summarized schematically in FIG. 34.

The measurements on the 9 cm thick breast phantom show that the monochromatic techniques described herein facilitate elimination of breast compression during mammography screening. A 4.5 cm compressed breast could be as thick at 9 cm when uncompressed. Whereas the commercial machine loses sensitivity as the breast thickness increases because it cannot increase the dose high enough to maintain the SNR and still remain below the regulated dose limit, the monochromatic x-ray system very easily provides the necessary SNR. As an example, of a monochromatic mammography procedure, a woman may lie prone on a clinic table designed to allow her breasts to extend through cutouts in the table. The monochromatic x-ray system may be designed to direct the x-rays parallel to the underside of the table. The table also facilitates improved radiation shielding for the patient by incorporating a layer of lead on the underside of the table's horizontal surface.

Figure 35:
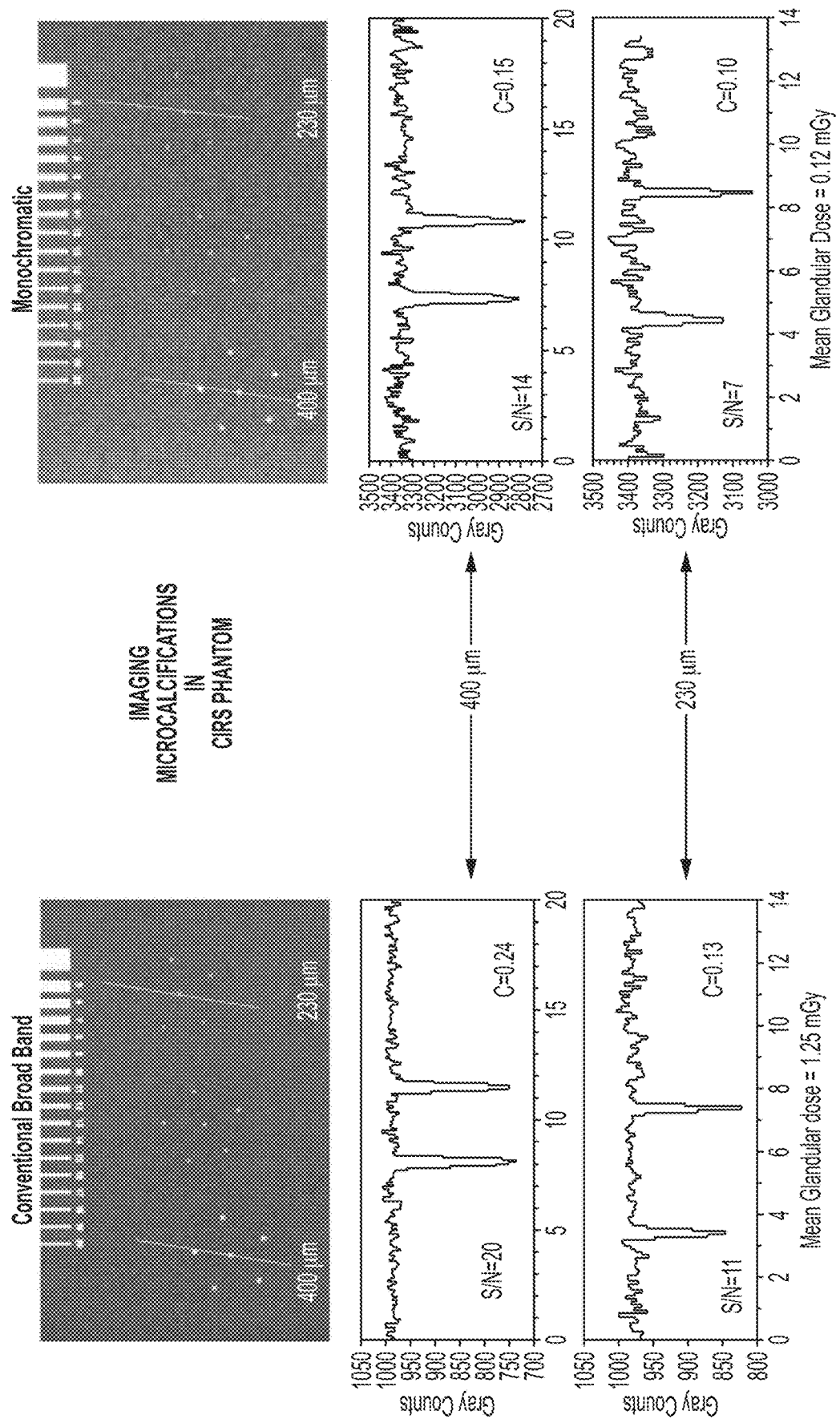
FIG. 35 illustrates images of micro-calcifications using a commercial broadband x-ray system and a monochromatic x-ray system according to some embodiments, along with corresponding histograms.
Figure 36:
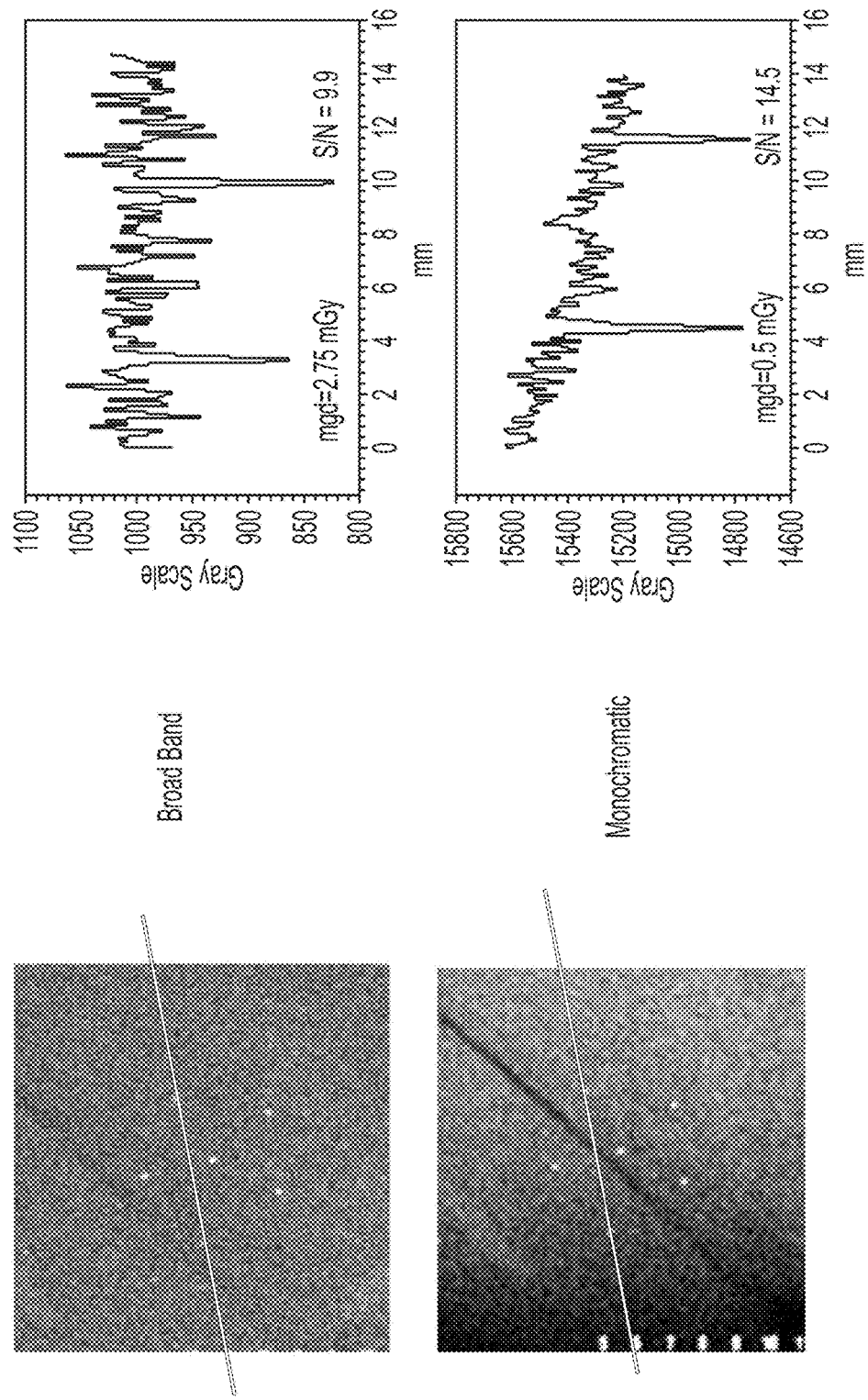
FIG. 36 illustrates images of micro-calcifications using a commercial broadband x-ray system and a monochromatic x-ray system according to some embodiments, along with corresponding histograms.

The inventor has recognized that the spatial resolution of the geometry of the monochromatic x-ray device described herein is excellent for mammographic applications. According to some embodiments, the monochromatic x-ray system has a source-to-detector distance of 760 mm, a secondary target cone with a 4 mm base diameter and 8 mm height, and an imaging detector of amorphous silicon with pixel sizes of 85 microns. This exemplary monochromatic x-ray device using the techniques described herein can easily resolve microcalcifications with diameters of 100-200 microns in the CIRS and ACR phantoms. FIGS. 35 and 36 illustrate images and associated histograms obtained using this exemplary monochromatic x-ray radiation device compared to images obtained using the same commercial device. The microcalcifications measured in the double ACR-CIRS phantom (stacked 2900 and 3200 phantoms) experiments described earlier using the monochromatic 25 keV x-ray lines have a SNR that is 50% higher than the SNR for the commercial machine and its mean glandular dose (mgd) is 6 times lower for these images. If one were to make the monochromatic SNR the same as that measured in the commercial machine, then the monochromatic mean glandular does (mgd) would be another factor of 2 times smaller for a total of 11 times lower.

Figure 37:
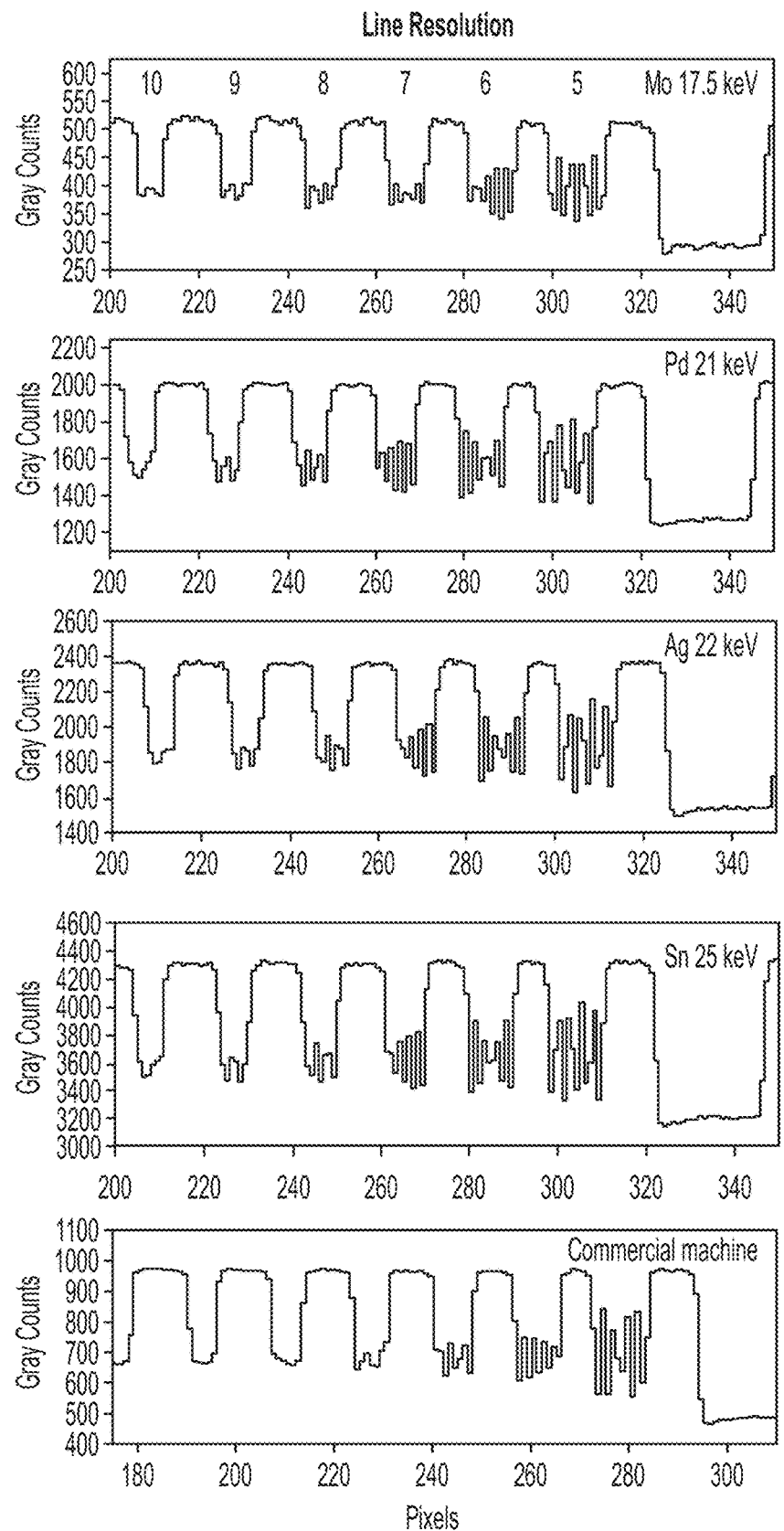
FIG. 37 illustrates line resolutions for different secondary targets and a commercial broadband x-ray system.
Figure 38:
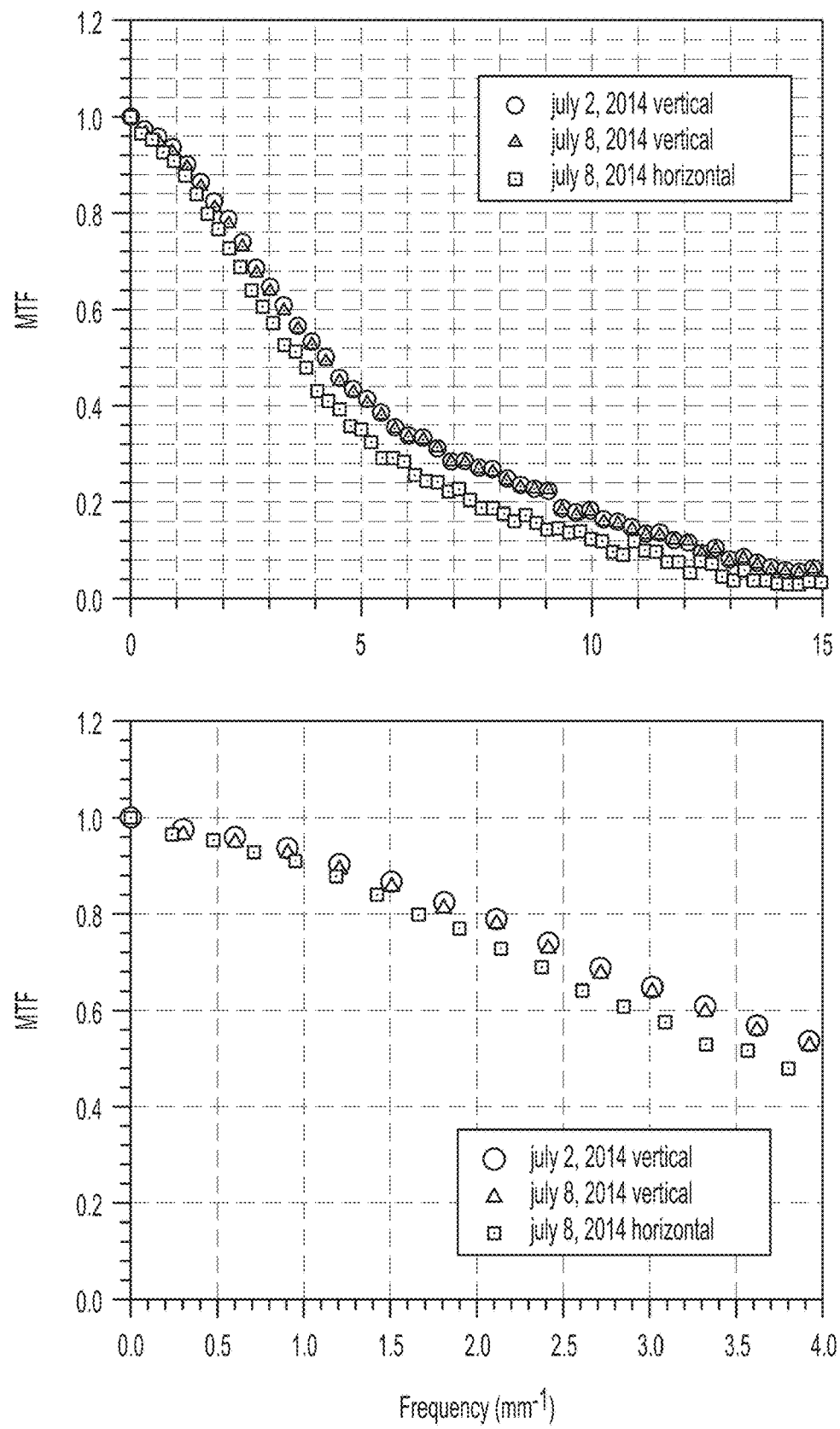
FIG. 38 illustrates the modulation transfer function (MTF) for the monochromatic instrument.

Simple geometric considerations indicate that the effective projected spot size of the secondary cone is 1-2 mm. FIG. 37 illustrates histograms of the measured intensity scans through line-pair targets that are embedded in the CIRS phantom. The spacing of the line-par targets ranges from 5 lines per mm up to 20 lines per mm. The top four histograms show that the scans for 18 keV, 21 keV, 22 keV and 25 keV energies using a 4 mm secondary cone described briefly above can discern alternating intensity structure up to 9 lines per mm which is consistent with a spatial resolution FWHM of 110 microns. The 18 keV energy can still discern structure at 10 lines per mm. The bottom histogram in FIG. 37 is an intensity scan through the same line-pair ensemble using a commonly used commercial broad band mammography system. The commercial system's ability to discern structure fails beyond 8 lines per mm. This performance is consistent with the system's modulation transfer function (MTF), a property commonly used to describe the spatial frequency response of an imaging system or a component. It is defined as the contrast at a given spatial frequency relative to low frequencies and is shown in FIG. 38. The value of 0.25 at 9 lines/mm is comparable to other systems with direct detector systems and better than flat panel detectors.

Figure 33:
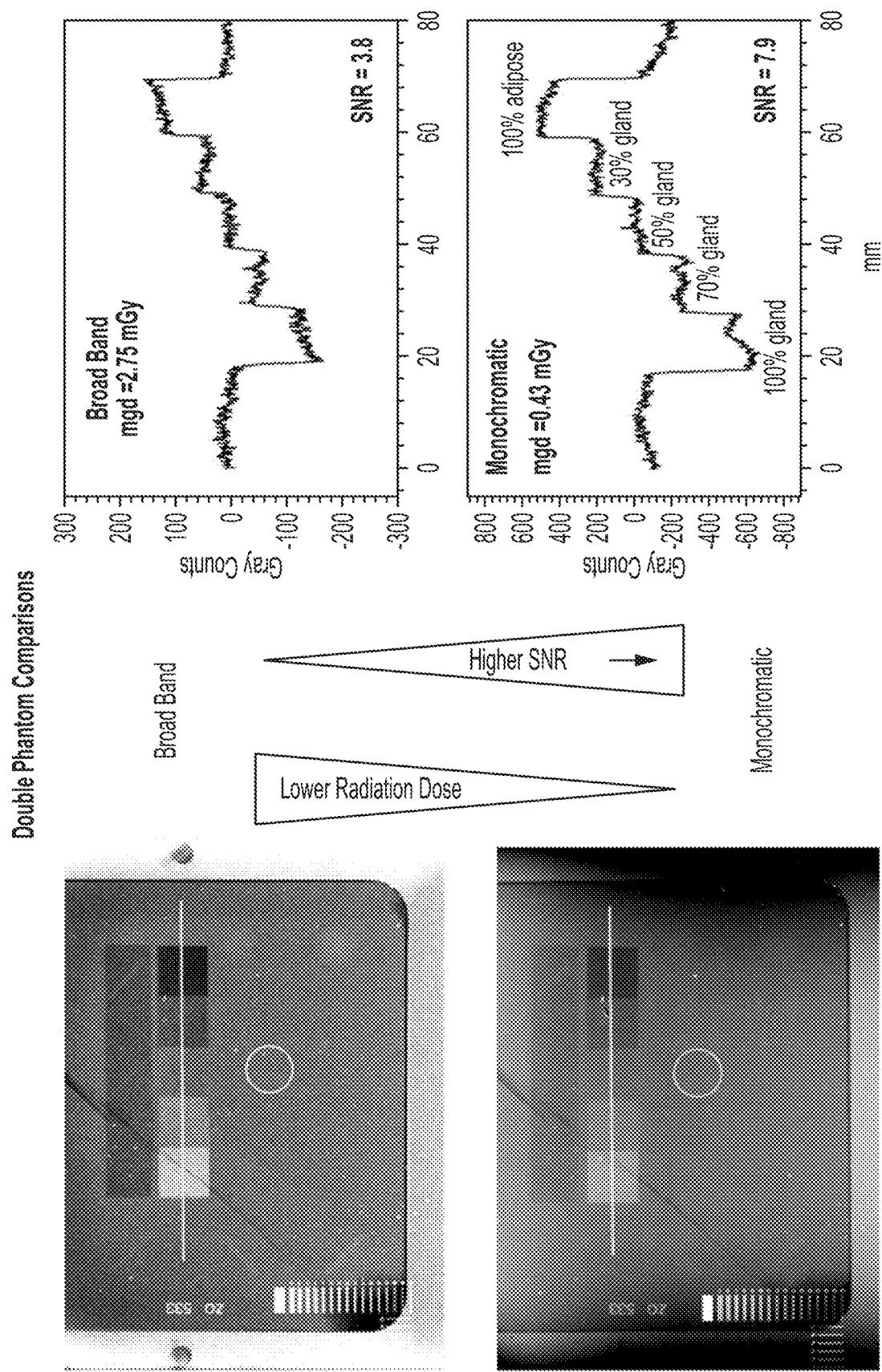
FIG. 33 illustrates images of the phantom in FIG. 32 using a commercial broadband x-ray system and a monochromatic x-ray system according to some embodiments, along with corresponding histograms.
Figure 34:
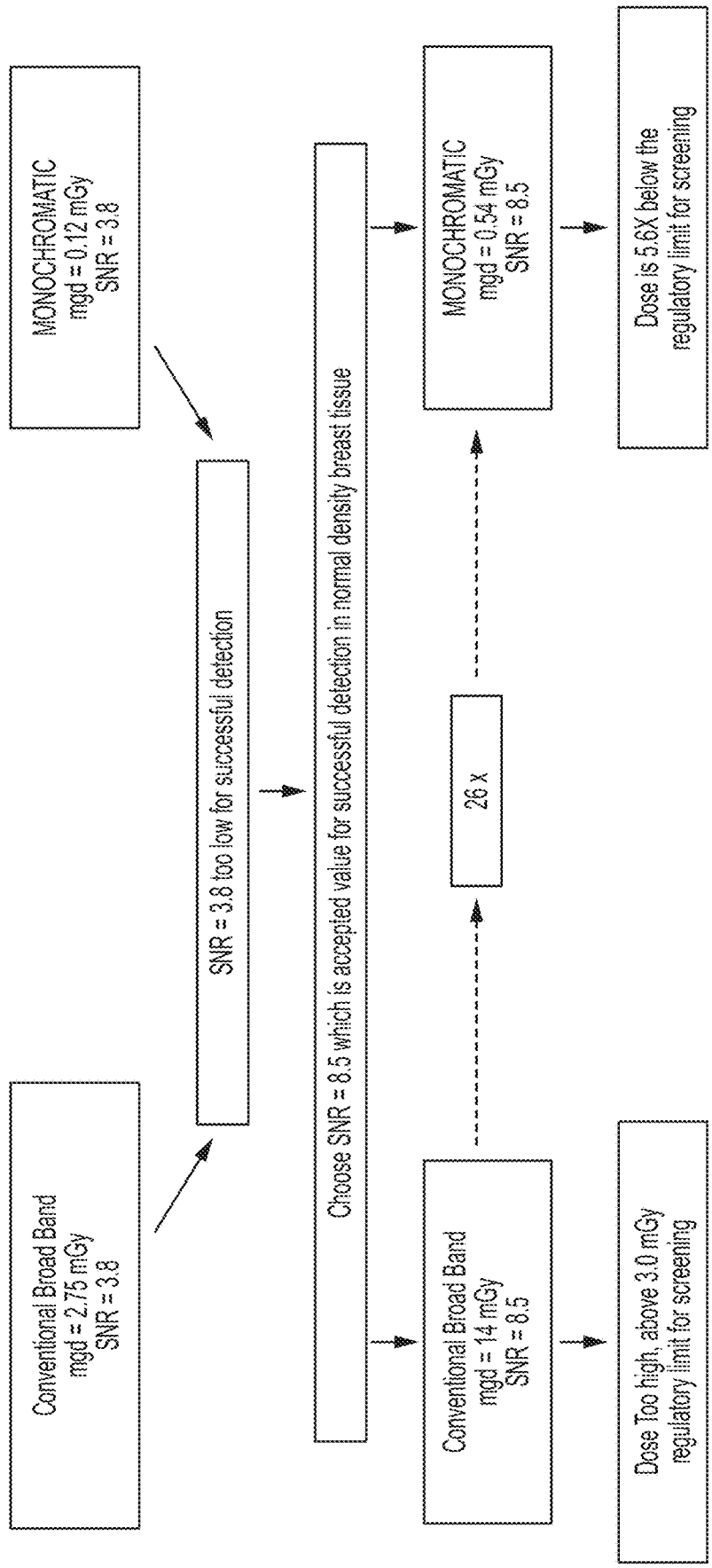
FIG. 34 illustrates conventional broadband mammography versus monochromatic mammography according to some embodiments.

According to some embodiments, the exemplary monochromatic system described herein was operated with up to 2000 watts in a continuous mode, i.e., the primary anode is water-cooled, the high voltage and filament current are on continuously and images are obtained using a timer-controlled, mechanical shutter. The x-ray flux data in FIG. 20 together with the phantom images shown in FIGS. 31 and 33 provide scaling guidelines for the power required to obtain a desired signal to noise for a specific exposure time in breast tissue of different compression thicknesses. Using a secondary material of Ag, 4 mm and 8 mm cone assemblies are compared for a compressed thickness of 4.5 cm and 50:50 glandular-adipose mix) in FIG. 39. The power requirements for a compressed thickness of 9 cm (50:50 glandular-adipose mix) as defined by experiments described above are compared in FIG. 40 for the 4 mm, 8 mm cones made from Sn.

The results indicate that a SNR of 8.5 obtained in a measurement of the 100% glandular block embedded in the CIRS phantom of normal breast density compressed to 4.5 cm can be achieved in a 5 second exposure expending 9.5 kW of power in the primary using the 4 mm cone (FIG. 39 top); 3.7 kW are needed if one uses the 8 mm cone (FIG. 39 bottom). In both of these cases, the source-to-detector (S-D) is 760 mm. If 2 sec are required, 9.2 kW are needed if an 8 mm cone is used or a 4 mm cone can be used at a source-to-detector (S-D) distance of 471 mm instead of 760 mm. Since the spatial resolution dependence is linear with S-D, then moving the 4 mm cone closer to the sample will only degrade the spatial resolution by 1.6 times, but it will still be better than the 8 mm cone at 760 mm. In general, there is a trade-off between spatial resolution and exposure time that will determine whether the 4 mm or 8 mm embodiments at the two source-to-detector distances best suit an application. This data serves as guides for designing monochromatic x-ray sources and do not exclude the possibilities for a variety of other target sizes and source-to-detector distances.

Figure 40:
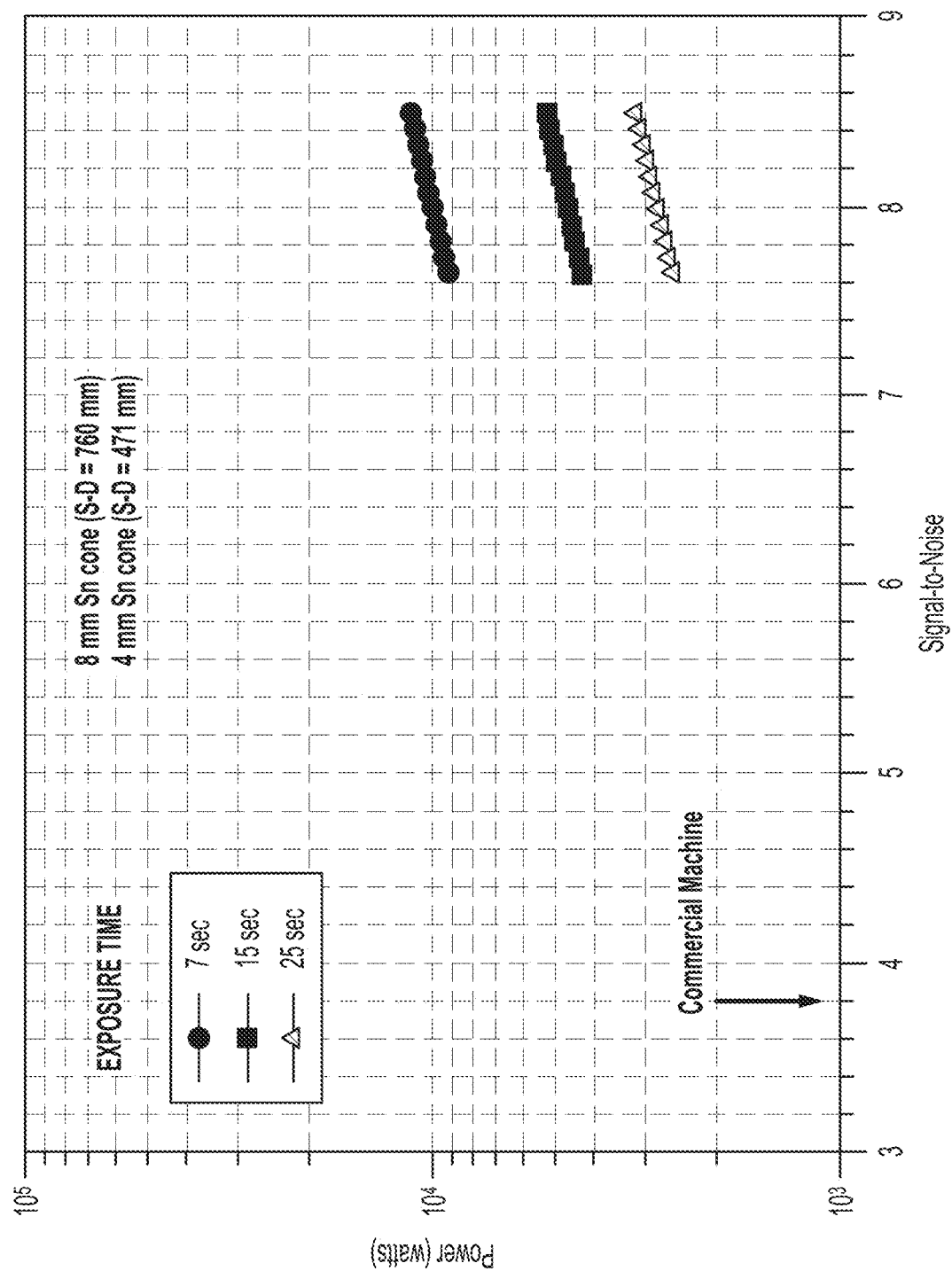
FIG. 40 illustrates power requirements needed for desired signal to noise ratios for different exposure times and cone geometries and with an indication of a commercial machine.

For thick breast tissue compressed to 9 cm, the dependency of the SNR on power is shown in FIG. 40. A 7 sec exposure can produce a SNR of 8.5 at 11 kW using a 4 mm Sn cone at a source-to-detector distance of 471 mm or with a 8 mm cone at 760 mm. Conventional broad band commercial mammography systems would have to deliver a 14 mGy dose to achieve this same SNR whereas the monochromatic system at 25 keV would only deliver 0.54 mGy, a factor of 26 times lower and still 2.3 times lower than the conventional dose of 1.25 mGy delivered by a commercial machine in screening women with normal density breast tissue compressed to 4.5 cm.

The inventor has recognized that maximizing the monochromatic X-ray intensity in a compact X-ray generator may be important for applications in medical imaging. Increased intensity allows shorter exposures which reduce motion artifacts and increase patient comfort. Alternatively, increased intensity can be used to provide increased SNR to enable the detection of less obvious features. There are three basic ways to increase the monochromatic flux: 1) maximizing fluorescence efficiency through the geometry of the target, 2) enhance the total power input on the primary in a steady state mode and 3) increase the total power input on the primary in a pulsed mode.

To increase the power and further decrease the exposure times, power levels of 10 kW-50 kW may be used. For example, an electron beam in high power commercial medical x-ray tubes (i.e., broadband x-ray tubes) has approximately a 1×7 mm fan shape as it strikes an anode that is rotating at 10,000 rpm. Since the anode is at a steep angle to the electron beam, the projected spot size in the long direction as seen by the viewer is reduced to about 1 mm. For an exposure of 1 sec, once can consider the entire annulus swept out by the fan beam as the incident surface for electron bombardment. For a 70 mm diameter anode, this track length is 210 mm, so the total incident anode surface area is about 1400 mm$^2$. For the monochromatic system using a conical anode with a 36 mm diameter and a truncated height of 6 mm, the total area of incidence for the electrons is 1000 mm$^2$. Therefore, it should be straightforward to make a 1 sec exposure at a power level that is 70% of the power of strong medical sources without damaging the anode material; 100 kW is a typical power of the highest power medical sources. Assuming a very conservative value that is 50% of the highest power, an anode made of a composite material operating at 50 kW should be achievable for short exposures. This is more power than is needed for thick and/or dense breast diagnostics but offers significant flexibility if reducing the effective size of the secondary cone becomes a priority.

A one second exposure at 50 kW generates 50 kJ of heat on the anode. If the anode is tungsten, the specific heat is 0.134 J/g/K. To keep the temperature below 1000° C. in order not to deform or melt the anode, the anode mass needs to be at least 370 gm. An anode of copper coated with a thick layer of gold would only have to be 130 gm. These parameters can be increased by at least 2-3 times without seriously changing the size or footprint of the source. For repeat exposures or for longer exposures, the anode in this system can be actively cooled whereas the rotating anode system has to rely on anode mass for heat storage and inefficient cooling through a slip-ring and slow radiative transfer of heat out of the vacuum vessel. The monochromatic x-ray systems described above can be actively cooled with water.

According to some embodiments, the primary anode material can be chosen to maximize the fluorescent intensity from the secondary. In the tests to date, the material of the primary has been either tungsten (W) or gold (Au). They emit characteristic K emission lines at 59 keV and 68 keV, respectively. These energies are relatively high compared to the absorption edges of silver (Ag; 25.6 keV) or tin (Sn; 29 keV) thereby making them somewhat less effective in inducing x-ray fluorescence in the Ag or Sn secondary targets. These lines may not even be excited if the primary voltage is lower than 59 keV. In this situation only the Bremsstrahlung induces the fluorescence. Primary material can be chosen with characteristic lines that are much closer in energy to the absorption edges of the secondary, thereby increasing the probability of x-ray fluorescence. For example, elements of barium, lanthanum, cerium, samarium or compounds containing these elements may be used as long as they can be formed into the appropriate shape. All have melting points above 1000° C. If one desires to enhance production of monochromatic lines above 50 keV in the most efficient way, higher Z elements are needed. For example, depleted uranium may be used (K line=98 keV) to effectively induce x-ray fluorescence in Au (absorption edge=80.7 keV). Operating the primary at 160 kV, the Bremsstrahlung plus characteristic uranium K lines could produce monochromatic Au lines for thorasic/chest imaging, cranial imaging or non-destructive industrial materials analysis.

For many x-ray imaging applications including mammography, the x-ray detector is an imaging array that integrates the energies of the absorbed photons. All spectroscopic information is lost. If a spectroscopic imager is available for a particular situation, the secondary target could be a composite of multiple materials. Simultaneous spectroscopic imaging could be performed at a minimum of two energies to determine material properties of the sample. Even if an imaging detector with spectral capability were available for use with a broad-band source used in a conventional x-ray mammography system for the purpose of determining the chemical composition of a suspicious lesion, the use of the spectroscopic imager would not reduce the dose to the tissue (or generically the sample) because the broad band source delivers a higher dose to the sample than the monochromatic spectrum.

Figure 41:
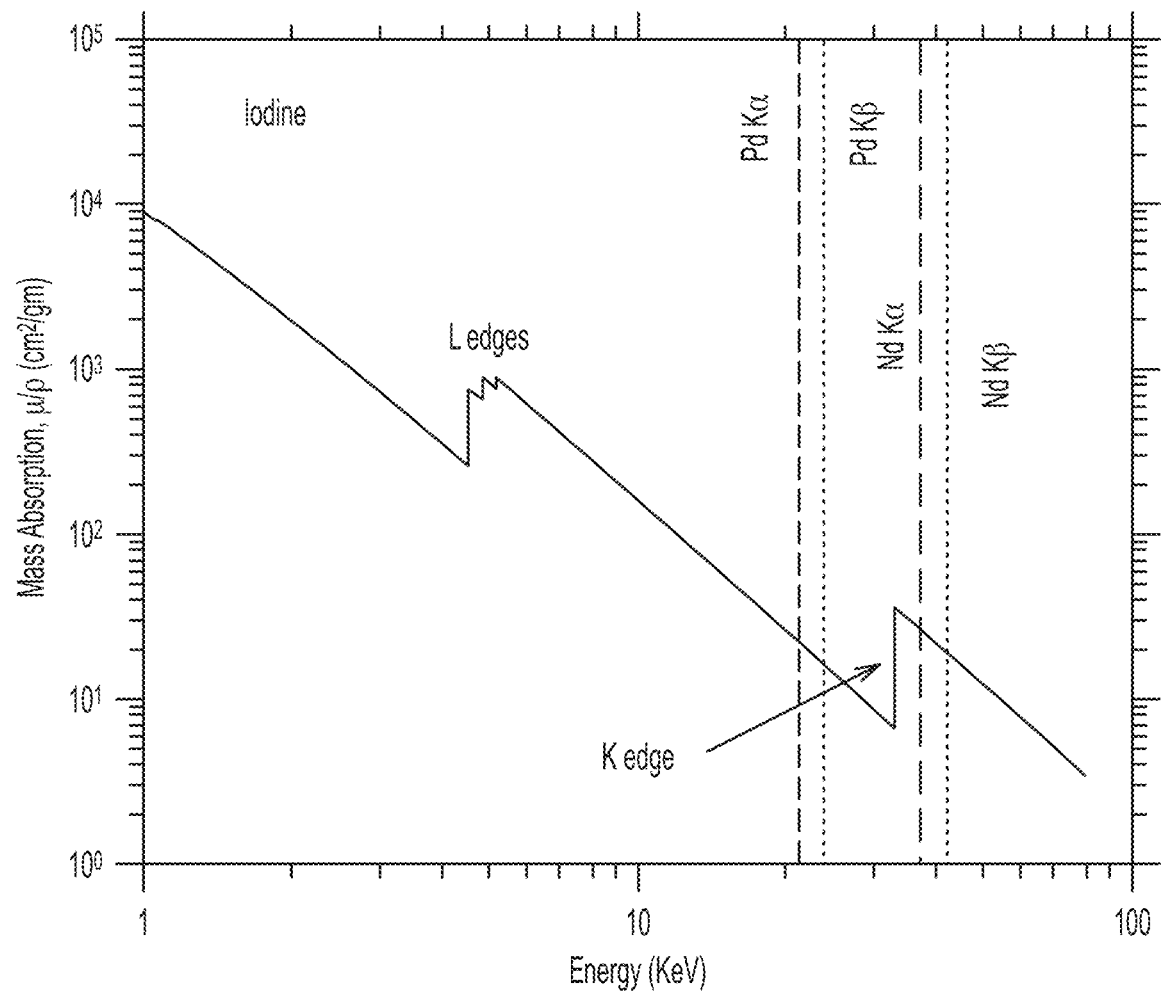
FIG. 41 illustrates the mass absorption coefficient curve for iodine.

Contrast-enhanced mammography using monochromatic x-ray radiation is superior to using the broad band x-ray emission. It can significantly increase the image detail by selectively absorbing the monochromatic X-rays at lower doses. The selective X-ray absorption of a targeted contrast agent would also facilitate highly targeted therapeutic X-ray treatment of breast tumors. In the contrast enhanced digital mammographic imaging conducted to date with broad band x-ray emission from conventional x-ray tubes, users try to take advantage of the increased absorption in the agent, such as iodine, by adjusting the filtering and increasing the electron accelerating voltage to produce sufficient x-ray fluence above the 33 keV K absorption edge of iodine. FIG. 41 shows the mass absorption curves for iodine as a function of x-ray energy. The discontinuous jumps are the L and K absorption edges. The contrast media will offer greater absorption properties if the broad band spectra from conventional sources span an energy range that incorporates these edges. As a result, detectability should improve.

Monochromatic radiation used in the mammographic system discussed here offers many more options for contrast-enhanced imaging. Ordinarily, one can select a fluorescent target to produce a monochromatic energy that just exceeds the iodine absorption edge. In this sense, the monochromatic x-ray emission from the tube is tuned to the absorption characteristics of the contrast agent. To further improve the sensitivity, two separate fluorescent secondary targets may be chosen that will emit monochromatic X-rays with energies that are below and above the absorption edge of the contrast agent. The difference in absorption obtained above and below the edge can further improve the image contrast by effectively removing effects from neighboring tissue where the contrast agent did not accumulate. Note that the majority of x-ray imaging detectors currently used in mammography do not have the energy resolution to discriminate between these two energies if they irradiate the detector simultaneously; these two measurements must be done separately with two different fluorescent targets in succession. This is surely a possibility and is incorporated in our system.

Figure 42:
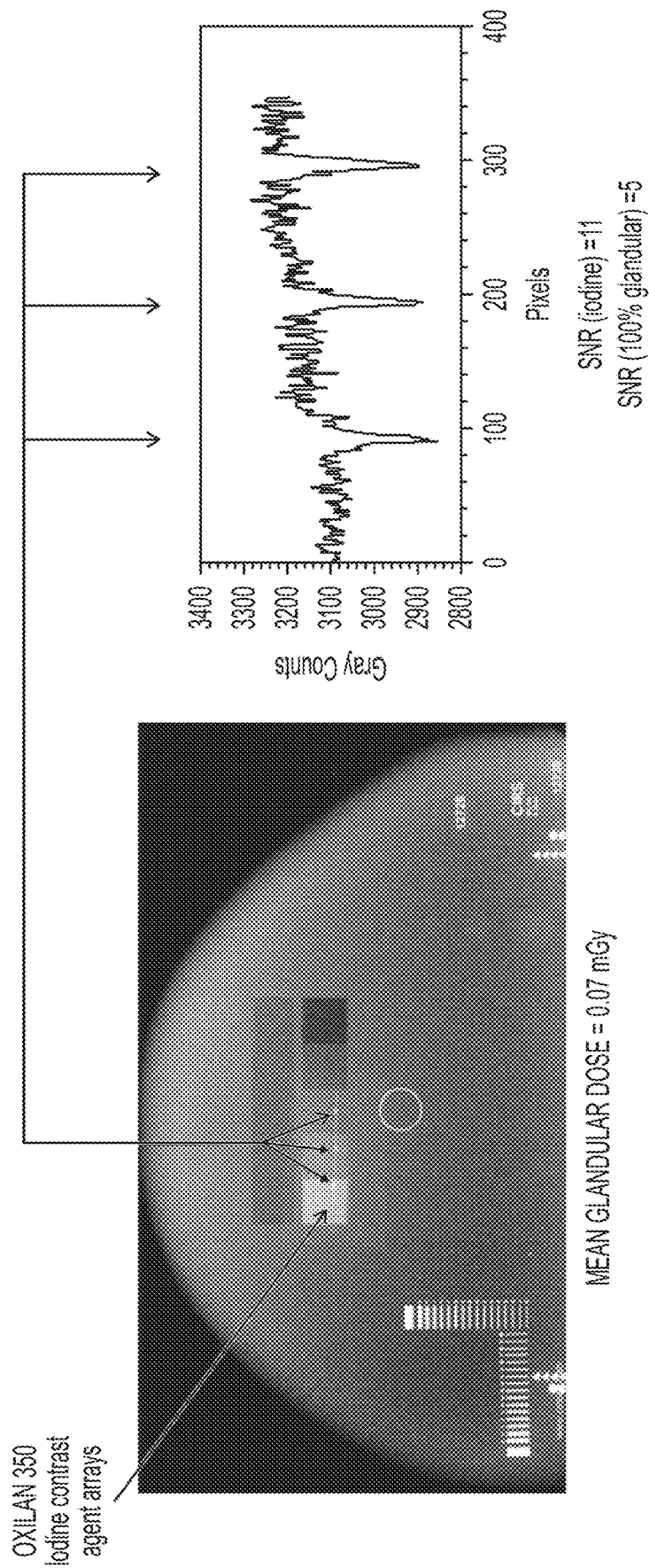
FIG. 42 illustrates an example of contrast enhanced imaging using Ag K x-rays at 22 keV and an iodine contrast agent called Oxilan 350.

Since the contrast agent enhances the x-ray absorption relative to the surrounding tissue, it is not necessary to select a monochromatic energy above the K edge to maximize absorption. For example, FIG. 41 shows that the absorption coefficient for the Pd K$\alpha$ 21.175 keV energy, which is below the K edge, is comparable to the absorption coefficient of the Nd K$\alpha$ 37.36 keV energy which is above the K edge. As long as the atoms of the contrast agent are sufficiently heavier (atomic number, Z>45) than the those in the surrounding tissue (C, O, N, P, S; Z<10 and trace amounts of Fe, Ni, Zn, etc., Z<30), the monochromatic x-ray technique increases the potential choices for contrast agents in the future. The secondary targets of Pd, Ag and Sn are perfect options for this application. Using monochromatic energies below the absorption edge of iodine, for example, takes better advantage of the quantum absorption efficiency of a typical mammographic imaging detector. The absorption at 37 keV (above the iodine edge) is about 2 times lower than at 22 keV (below the edge). The lower energy may also prove to have better detectability in the surrounding tissue simultaneously. FIG. 42 shows a linear set of 3 drops of Oxilan 350, an approved iodine contrast agent manufactured by Guerbet superimposed on the ACR phantom. The amount of iodine in each of the drops ~1 mg iodine.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A monochromatic x-ray device comprising:
    a broadband x-ray source comprising:
        an electron source configured to emit electrons;
        a primary target configured to produce broadband x-ray radiation in response to incident electrons from the electron source;
    a housing configured to be removeably coupled to the broadband x-ray source and configured to accommodate a secondary target configured to generate monochromatic x-ray radiation via fluorescence in response to incident broadband x-ray radiation, the housing for the secondary target comprising an aperture through which monochromatic x-ray radiation from the secondary target is emitted, the housing configured to position the secondary target so that at least some of the broadband x-ray radiation emitted by the primary target is incident on the secondary target so that, when the monochromatic x-ray device is operated, monochromatic x-ray radiation is emitted via the aperture having a monochromaticity of greater than or equal to 0.7 across a field of view of at least approximately 15 degrees.

2. The monochromatic x-ray device of claim 1, wherein, when the device is operated, monochromatic x-ray radiation is emitted via the aperture having a monochromaticity of greater than or equal to 0.8 across a field of view of at least approximately 15 degrees.

3. The monochromatic x-ray device of claim 1, wherein, when the device is operated, monochromatic x-ray radiation is emitted via the aperture having a monochromaticity of greater than or equal to 0.9 across a field of view of at least approximately 15 degrees.

4. The monochromatic x-ray device of claim 1, wherein, when the device is operated, monochromatic x-ray radiation is emitted via the aperture having a monochromaticity of greater than or equal to 0.95 across a field of view of at least approximately 15 degrees.

5. The monochromatic x-ray device of claim 1, wherein the housing comprises:
    a transmissive portion configured to allow broadband x-ray radiation to be transmitted to the secondary target when present; and
    a blocking portion configured to absorb broadband x-ray radiation.

6. The monochromatic x-ray device of claim 5, wherein the transmissive portion comprises at least a first transmissive material substantially transparent to the broadband x-ray radiation emitted by the broadband x-ray source.

7. The monochromatic x-ray device of claim 6, wherein the transmissive portion comprises at least one of aluminum, carbon, carbon fiber, boron, boron nitride, beryllium oxide, silicon and silicon nitride.

8. The monochromatic x-ray device of claim 5, wherein the blocking portion comprises at least a first blocking material substantially opaque to the broadband x-ray radiation emitted by the broadband x-ray source.

9. The monochromatic x-ray device of claim 5, wherein the housing is configured such that, when the secondary target is accommodated within the housing, at least a first portion of the secondary target is positioned within the transmissive portion of the housing and a second portion of the secondary target is positioned within the blocking portion of the housing.

10. The monochromatic x-ray device of claim 9, wherein the transmissive portion comprises a first cylindrical portion configured to accommodate the secondary target and the blocking portion comprises a second cylindrical portion configured to overlap the second portion of the secondary target when the first cylindrical portion accommodates the secondary target.

11. The monochromatic x-ray device of claim 10, wherein the secondary target is conical, wherein the first cylindrical portion is configured to accommodate at least a portion of a base of the conical secondary target, and wherein the second cylindrical portion is configured to overlap at least a portion of a tip of the conical secondary target.

12. The monochromatic x-ray device of claim 10, wherein the second cylindrical portion is configured to overlap at least 1 mm of the secondary target when the first cylindrical portion accommodates the secondary target.

13. The monochromatic x-ray device of claim 10, wherein the second cylindrical portion is configured to overlap at least 2 mm of the secondary target when the first cylindrical portion accommodates the secondary target.

14. The monochromatic x-ray device of claim 10, wherein the second cylindrical portion is configured to overlap at least 3 mm of the secondary target when the first cylindrical portion accommodates the secondary target.

15. The monochromatic x-ray device of claim 5, wherein the housing is configured such that, when the secondary target is accommodated within the housing, the secondary target is positioned exclusively within the transmissive portion.

16. A method of generating monochromatic x-rays comprising:
   placing a secondary target within a removeable housing, the secondary target configured to generate monochromatic x-ray radiation via fluorescence in response to incident broadband x-ray radiation;
   coupling the removeable housing to a broadband x-ray source comprising an electron source and a primary target configured to produce broadband x-ray radiation in response to incident electrons from the electron source;
   generating broadband x-ray radiation from the primary target;
   generating monochromatic x-ray radiation from the secondary target in response to incident broadband x-ray radiation from the primary target;
   emitting at least some of the monochromatic x-ray radiation via an aperture of the housing; and
   blocking at least some of the broadband x-ray radiation such that the monochromatic x-ray radiation emitted via the aperture has a monochromaticity of greater than or equal to 0.7 across a field of view of at least approximately 15 degrees.

17. The method of claim 16, wherein the monochromatic x-ray radiation emitted via the aperture has a monochromaticity of greater than or equal to 0.8 across a field of view of at least approximately 15 degrees.

18. The method of claim 16, wherein the monochromatic x-ray radiation emitted via the aperture has a monochromaticity of greater than or equal to 0.9 across a field of view of at least approximately 15 degrees.

19. The method of claim 16, wherein the monochromatic x-ray radiation emitted via the aperture has a monochromaticity of greater than or equal to 0.95 across a field of view of at least approximately 15 degrees.

\* \* \* \* \*